(12) United States Patent
Cooper et al.

(10) Patent No.: US 8,563,538 B2
(45) Date of Patent: *Oct. 22, 2013

(54) PREVENTING AND/OR TREATING CARDIOVASCULAR DISEASE AND/OR ASSOCIATED HEART FAILURE

(75) Inventors: Garth J. S. Cooper, Auckland (NZ); John R. Baker, Auckland (NZ)

(73) Assignee: Philera New Zealand Limited, Auckland (NZ)

(*) Notice: Subject to any disclaimer, the term of this patent is extended or adjusted under 35 U.S.C. 154(b) by 0 days.

This patent is subject to a terminal disclaimer.

(21) Appl. No.: 13/037,223

(22) Filed: Feb. 28, 2011

(65) Prior Publication Data

US 2011/0212188 A1    Sep. 1, 2011

Related U.S. Application Data

(63) Continuation of application No. 11/221,298, filed on Sep. 7, 2005, now Pat. No. 8,034,799, which is a continuation of application No. 10/388,213, filed on Mar. 12, 2003, now Pat. No. 6,951,890, and a continuation of application No. PCT/NZ03/00042, filed on Mar. 10, 2003.

(60) Provisional application No. 60/364,382, filed on Mar. 12, 2002.

(30) Foreign Application Priority Data

Mar. 8, 2002  (NZ) .......................... 517721
Mar. 11, 2002  (NZ) .......................... 517725

(51) Int. Cl.
| | | |
|---|---|---|
| *A61K 31/33* | (2006.01) | |
| *A61K 31/315* | (2006.01) | |
| *A61K 31/195* | (2006.01) | |
| *A61K 31/185* | (2006.01) | |
| *A61K 31/07* | (2006.01) | |
| *A61K 33/32* | (2006.01) | |

(52) U.S. Cl.
USPC ........... 514/183; 514/494; 514/561; 514/562; 514/578; 514/725; 424/641; 424/643

(58) Field of Classification Search
USPC ................. 514/183, 494, 561, 562, 578, 725; 424/641, 643
See application file for complete search history.

(56) References Cited

U.S. PATENT DOCUMENTS 6,951,890 B2 * 10/2005 Cooper et al. ................ 514/673
8,034,799 B2 * 10/2011 Cooper et al. ................ 514/183

* cited by examiner

*Primary Examiner* — Raymond Henley, III
(74) *Attorney, Agent, or Firm* — McDonnell Boehnen Hulbert & Berghoff LLP

(57) ABSTRACT

Methods are provided for reducing copper values for, by way of example, treating, preventing or ameliorating tissue damage such as, for example, tissue damage that may be caused by (i) disorders of the heart muscle (for example, cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy, (ii) atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries, (iii) toxic, drug-induced, and metabolic (including hypertensive and/or diabetic disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems, (iv) plaque rupture of atheromatous lesions of major blood vessels such as the aorta, the coronary arteries, the carotid arteries, the cerebrovascular arteries, the renal arteries, the iliac arteries, the fermoral arteries and the popliteal arteries, (v) diabetes or the complications of diabetes.

22 Claims, 27 Drawing Sheets

Hypothesis

1. **Glyco-oxidation product ion (AGE* formation)**

Lipid or Protein + glucose → {Protein - AGE
    {Lipid - AGE

Cu-AGE Protein or Cu-AGE Lipid → Protein + $O_2^-$

2. Superoxide dismutase

$2O_2^- + 2H^+ \rightarrow H_2O_2 + O_2$

3. Haber-Weiss Reaction (Copper salt catalyst)

$H_2O_2 + 2O_2^- \rightarrow O_2 + OH\cdot + OH^-$

*AGE = Advance Glycation Endproduct

FIGURE 2

Wilcoxon p<0.05 for STZ v STZ/D7

| Cu excretion | | Dose level | | | |
|---|---|---|---|---|---|
| Mixed Model Effects | Baseline | 0.1 mg.kg$^{-1}$ | 1.0 mg.kg$^{-1}$ | 10 mg.kg$^{-1}$ | 100 mg.kg$^{-1}$ |
| Diabetes (normal/diabetic rats) | $F_{1,24}=18.52$ $P=0.0002$ | $F_{1,24}=19.82$ $P=0.0002$ | $F_{1,24}=21.92$ $P<0.0001$ | $F_{1,24}=9.93$ $P<0.0001$ | $F_{1,24}=17.82$ $P<0.0003$ |
| Drug (drug/saline) | $F_{1,24}=1.73$ NS | $F_{1,24}=24.94$ $P<0.0001$ | $F_{1,24}=78.36$ $P<0.0001$ | $F_{1,24}=135.36$ $P<0.0001$ | $F_{1,24}=102.17$ $P<0.0001$ |
| Interaction | $F_{1,24}=0.16$ NS | $F_{1,24}=3.58$ NS | $F_{1,24}=7.16$ $P<0.0132$ | $F_{1,24}=6.02$ $P<0.0218$ | $F_{1,24}=12.43$ $P<0.0017$ |
| Sampling time (repeated measure) | $t_1, t_2$ | $t_1, t_2, t_3, t_4$ | $t_1, t_2, t_3, t_4$ | $t_1, t_2, t_3, t_4$ | $t_1, t_2, t_3, t_4$ |

| Fe excretion | | Dose level | | | |
|---|---|---|---|---|---|
| Mixed Model Effects | Baseline | 0.1 mg.kg$^{-1}$ | 1.0 mg.kg$^{-1}$ | 10 mg.kg$^{-1}$ | 100 mg.kg$^{-1}$ |
| Diabetes (normal/diabetic rats) | $F_{1,23}=12.87$ $P=0.0016$ | $F_{1,23}=15.82$ $P=0.0006$ | $F_{1,24}=22.68$ $P<0.0001$ | $F_{1,24}=14.93$ $P=0.0007$ | $F_{1,24}=7.35$ $P=0.0122$ |
| Drug (drug/saline) | $F_{1,24}=8.6$ $P=0.0075$ | $F_{1,23}=7.89$ $P=0.01$ | $F_{1,24}=12.23$ $P<0.0019$ | $F_{1,24}=10.91$ $P=0.003$ | $F_{1,24}=2.47$ $P=0.1292$ |
| Interaction | $F_{1,23}=12.10$ $P=0.002$ | $F_{1,23}=15.06$ $P=0.0008$ | $F_{1,24}=14.07$ $P=0.001$ | $F_{1,24}=17.72$ $P=0.0303$ | $F_{1,24}=16.76$ $P=0.0004$ |
| Sampling time (repeated measure) | 2 | $t_1, t_2, t_3, t_4$ | $t_1, t_2, t_3, t_4$ | $t_1, t_2, t_3, t_4$ | $t_1, t_2, t_3, t_4$ |

FIGURE 27

PREVENTING AND/OR TREATING CARDIOVASCULAR DISEASE AND/OR ASSOCIATED HEART FAILURE

RELATED APPLICATIONS

This application is a continuation of U.S. Ser. No. 11/221,298, filed Sep. 7, 2005; which is a continuation of, and claims priority to, U.S. Ser. No. 10/388,213, filed Mar. 12, 2003; which in turn is a US 371 National Stage application of, and claims priority to, International PCT Application No. NZ/03/00042, filed Mar. 10, 2003, which claims the benefit of New Zealand Provisional Patent Application Serial No. 517721, filed Mar. 8, 2002, New Zealand Provisional Patent Application Serial No. 517725, file Mar. 11, 2002; and U.S. Provisional Patent Application Ser. No. 60/364,382, filed Mar. 12, 2002. The contents of each of which are hereby incorporated by reference in their entireties.

FIELD OF THE INVENTION

This invention concerns methods of treatment, prevention or amelioration of a disease, disorder or condition in a mammal (hereafter "treating"), including, for example, a human being, having undesired copper levels that cause or lead to tissue damage. Treating of mammals includes those, for example, predisposed to copper-involved or -mediated free radical damage of tissue and/or to copper-involved or -mediated impairment of normal tissue stem cell responses. The invention has application inter alia to diabetes-related and non-diabetes-related heart failure, macrovascular disease or damage, microvascular disease or damage, and/or toxic (e.g., hypertensive) tissue and/or organ disease or damage (including such ailments as may, for example, be characterized by heart failure, cardiomyopathy, myocardial infarction, and related arterial and organ diseases) and to related compounds, compositions, formulations, uses, and procedures.

BACKGROUND OF THE INVENTION

The following description includes information that may be useful in understanding the present invention. It is not an admission that any of the information provided herein is prior art, or relevant, to the presently described or claimed inventions, or that any publication or document that is specifically or implicitly referenced is prior art.

Glucose is the primary source of energy for the human body. Absorbed from the intestine it is metabolized by energy production (by conversion to water and carbon dioxide), conversion to amino acids and proteins or keto-acids, and storage as glycogen. Glucose metabolism is regulated by complex orchestration of hormone activities. While all dietary sugars are broken down into various carbohydrates, the most important is glucose, which is metabolized in nearly all cells of the body. Glucose enters the cell by facilitated diffusion (glucose transport proteins). This facilitated transport is stimulated very rapidly and effectively by an insulin signal, pursuant to which glucose transport into muscle and adipose cells is increased up to twenty fold. After glucose is transported into the cytoplasm, insulin then directs the disposition of it by conversion of glucose to glycogen, to pyruvate and lactate, and to fatty acids.

Diabetes mellitus is heterogeneous group of metabolic disorders, connected by raised plasma glucose concentration and disturbance of glucose metabolism with resulting hyperglycemia. The hyperglycemia in diabetes mellitus generally results from defects in insulin secretion, insulin action, or both. Although its etiology has been clouded, the World Health Organization (WHO) has set forth a classification scheme for diabetes mellitus that includes type 1 diabetes mellitus, type 2 diabetes mellitus, gestational diabetes, and other specific types of diabetes mellitus. Former terms like IDDM (insulin-dependent diabetes mellitus), NIDDM (non-insulin dependent diabetes mellitus), and juvenile-onset diabetes mellitus or adult-onset diabetes mellitus are no longer primarily used to describe those conditions.

The terms "insulin-dependent diabetes" (IDDM) or "juvenile-onset diabetes" previously encompassed what is now referred to as type 1 diabetes. Type I diabetes results from an autoimmune destruction of the insulin-secreting β-cells of the pancreas. There are several markers of this autoimmune destruction, detectable in body fluids and tissues, including islet cell autoantibodies, autoantibodies to insulin, autoantibodies to glutamic acid decarboxylase (GAD65), and autoantibodies to the tyrosine phosphatases IA-2 and IA-2β. While genetic factors are strongly implicated, the concordance rate in twin studies is under 50% and supports a role for environmental factors, which are said to include viral infections. The autoimmune process typically begins many years before clinical detection and presentation. The rate of β-cell destruction is quite variable, being rapid in some individuals (mainly infants and children) and usually slow in adults.

The terms "non-insulin-dependent diabetes mellitus" (NIDDM) or "adult-onset diabetes" previously encompassed what is now referred to as type 2 diabetes mellitus. The disease usually develops after 40 years of age. It is much more common that type 1 diabetes and comprises approximately 90% of all individuals with diabetes. Type 2 patients are usually older at the onset of disease, and are characterized by various symptoms. Insulin concentrations are mostly increased but they can be normal or decreased. Obesity is common. Diet and exercise regimens leading to weight reduction can ameliorate hyperglycemia. Oral hypoglycaemic drugs are also used in an effort to lower blood sugar. Nevertheless, insulin is sometimes required to correct hyperglycemia, particularly as patients grow older or as their β-cells fail.

Two groups of disorders may be said to typify type 2 diabetes mellitus. The first one is a decreased ability of insulin to act on peripheral tissues, usually referred to as "insulin resistance." Insulin resistance is defined as a decreased biological response to normal concentrations of circulating insulin and represents the primary underlying pathological process. The second is the dysfunction of pancreatic β-cells, represented by the inability to produce sufficient amounts of insulin to overcome insulin resistance in the peripheral tissues. Eventually, insulin production can be insufficient to compensate for the insulin resistance due to β-cell dysfunction. The common result is a relative deficiency of insulin. Data support the concept that insulin resistance is the primary defect, preceding the derangement of insulin secretion. As with type 1 diabetes, the basis of the insulin resistance and insulin secretion defects is believed to be a combination of environmental and genetic factors.

Gestational diabetes mellitus is usually asymptomatic and not necessarily life threatening to the mother. The condition is associated with an increased incidence of neonatal morbidity, neonatal hypoglycaemia, macrosomia and jaundice. Even normal pregnancies are associated with increasing insulin resistance, mostly in the second and third trimesters. Euglycaemia is maintained by increasing insulin secretion. In those women who are not able to increase the secretion of insulin, gestational diabetes develops. The pathophysiology of gestational diabetes mellitus is not well known but is said to include family history of diabetes mellitus, obesity, complications in previous pregnancies and advanced maternal age.

Other specific types of diabetes mellitus are heterogeneous, with the following representing the largest groups: genetic defects of β-cell function; genetic defects in insulin action; diseases of the exocrine pancreas (e.g., pancreatitis, trauma/pancreatectomy, neoplasia, cystic fibrosis, hemochromatosis, and others); other endocrinopathies (e.g., acromegaly, Cushing's syndrome, glucagonoma, pheochromocytoma, hyperthyroidism, somatostatinoma, aldosteronoma, and others); drug- or chemical-induced diabetes mellitus (e.g., from vacor (an acute rodenticide released in 1975 but withdrawn as a general-use pesticide in 1979 because of severe toxicity, exposure to vacor causing destruction of the beta cells of the pancreas and diabetes mellitus in survivors), pentamidine, nicotinic acid, glucocorticoids, thyroid hormone, diazoxide, beta-adrenergic agonists, thiazides, phenyloin, alfa-interferon, and others); infection-induced diabetes mellitus (e.g., from congenital rubella, cytomegalovirus, and others); rare forms of immune-mediated diabetes; and, other genetic syndromes sometimes associated with diabetes (e.g., Down syndrome, Klinefelter's syndrome, Turner's syndrome, Wolfram syndrome, Friedreich's ataxia, Huntington's chorea, Lawrence-Moon Beidel syndrome, Myotonic dystrophy, Porphyria Prader-Willi syndrome, and others). The etiology and pathophysiology are very different, mostly complicated or connected to insulin secretion and action derangement, as well as signal transduction inside the cells disarrangement. See "The Expert Committee on the Diagnosis and Classification of Diabetes Mellitus: Committee Report 2001," American Diabetes Association, *Diabetes Care* 1997; 20:1183-97 (revised 1999; republished January 2002); Lernmark A., "Type I Diabetes," *Clin. Chem.* 45 (8B): 1331-8 (1999); Lebowitz H. E., "Type 2 Diabetes: An Overview," *Clin. Chem.* 45 (8B): 1339-45 (1999). The vast majority of cases of diabetes fall into two broad etiopathogenetic categories, type 1 diabetes (characterized by an absolute deficiency of insulin secretion) and the much more prevalent type 2 diabetes (characterized by a combination of resistance to insulin action and an inadequate compensatory insulin secretory response), Sixteen million people in the United States are estimated to have diabetes, and more than 90% of these patients have type 2 diabetes. National Center for Health Statistics. *Health United Stats*. Washington, D.C.: Government Printing Office, 1998. The World Health Organization estimates that the number of diabetic adults will more than double globally, from 143 million in 1997 to 300 million in 2025, largely because of dietary and other lifestyle factors.

Diabetes mellitus is a chronic condition characterized by the presence of fasting hyperglycemia and the development of widespread premature atherosclerosis. Patients with diabetes have increased morbidity and mortality due to cardiovascular diseases, especially coronary artery disease. Vascular complications in diabetes may be classified as microvascular, affecting the retina, kidney and nerves and macrovascular, predominantly affecting coronary, cerebrovascular and peripheral arterial circulation. Thus, the chronic hyperglycemia of diabetes is associated with long-term damage, dysfunction, and failure of various organs, especially the eyes, kidneys, nerves, heart, and blood vessels and long-term complications of diabetes include retinopathy with potential loss of vision; nephropathy leading to renal failure; peripheral neuropathy with risk of foot ulcers, amputation, and Charcot joints; and autonomic neuropathy causing gastrointestinal, genitourinary, and cardiovascular symptoms and sexual dysfunction. Glycation of tissue proteins and other macromolecules and excess production of polyol compounds from glucose are among the mechanisms thought to produce tissue damage from chronic hyperglycemia. Patients with diabetes have an increased incidence of atherosclerotic cardiovascular, peripheral vascular, and cerebrovascular disease. Hypertension, abnormalities of lipoprotein metabolism, and periodontal disease are often found in people with diabetes.

Chronic hyperglycemia results in hyperglycosylation of multiple proteins and is the hallmark of diabetes. Hyperglycosylated proteins have altered function resulting in a spectrum of effects. Epidemiological studies have confirmed that hyperglycemia is the most important factor in the onset and progress of diabetes complications, both in insulin-dependent and non-insulin-dependent diabetes mellitus. Mechanisms connecting hyperglycemia with complications of long-term diabetes have been investigated indicating the involvement of non-enzymatic glycation processes. The nonenzymatic glycation process in one in which glucose is chemically bound to amino groups of proteins, but without the help of enzymes. It is a covalent reaction where, by means of N-glycoside bonding, sugar-protein complex is formed through a series of chemical reactions described by Maillard. In Maillard reactions, sugar-protein complexes are formed (Amadori rearrangement) and represent an early product of nonenzymatic glycation and an intermediary that is a precursor of later compounds. Numerous intermediary products are then formed, followed by complex product polymerization reactions resulting in heterogeneous structures called advanced glycation endproducts (AGE). It was believed that the primary role in Maillard reactions was exclusively played by high glucose concentration. However, recent data show that, in spite of the fact that sugars are the main precursors of AGE compounds, numerous intermediary metabolites including α-oxoaldehydes also participate in nonenzymatic glycation reactions. Such intermediary products are generated during glycolysis (methylglyoxal) or in the polyolic pathway, and they can also be formed by autooxidation of carbohydrates (glyoxal). Alpha-oxoaldehydes modify AGEs surprisingly fast, in contrast to classical Maillard reactions which are slower.

Glycation has both physiological and pathophysiological significance. In physiological conditions glycation can be detected in the aging process, and the reactions are significantly faster and more intensive with frequently increased glucose concentrations. In diabetology the importance of these processes is manifest in two essential issues, the effect of protein glycation on the change of protein structure and function, and the use of glycated proteins level as a parameter of integrated glycemia. A classical example of nonenzymatic glycation is the formation of glycated hemoglobin (HbA1c). The degree of nonenzymatic glycation being directly associated with blood glucose levels, the percentage of HbA1c in diabetes can be very increased. HbA1c was the first studied glycated protein, but it was soon discovered that other, various structural and regulatory proteins, are also subject to nonenzymatic glycation forming glycation end-products.

Protein modification with AGE is irreversible, there being no enzymes in the organism able to hydrolyze AGE compounds, which consequently accumulate during the life span of a protein on which they had were formed. Examples include all types of collagen, albumin, basic myelin protein, eye lens proteins, lipoproteins and nucleic acid. AGEs change the function of many proteins and contribute to various late complications of diabetes mellitus. The major biological effect of excessive glycation include the inhibition of regulatory molecule binding, crosslinking of glycated proteins, trapping of soluble proteins by glycated extracellular matrix, decreased susceptibility to proteolysis, inactivation of enzymes, abnormalities of nucleic acid function, and increased immunogenicity in relation to immune complexes formation.

It has also been reported that AGEs progressively accumulate on the tissues and organs that develop chronic complications of diabetes mellitus like retinopathy, nephropathy, neuropathy and progressive atherosclerosis. Immunohistochemical methods have demonstrated the presence of different AGE compounds in glomeruli and tubuli cells in both experimental and human diabetic nephropathy. The AGE role in atherosclerosis may also be significant. For instance, reticulated and irreversible low-density lipoprotein (LDL) from the circulation binds to AGE-modified collagen of blood vessel walls. In the majority of blood vessels such reticular binding delays normal outflow of LDL particles which penetrate vessel walls and thus enhance the deposit of cholesterol in the intima. This is followed by an accelerated development of atherosclerosis.

The level of AGE proteins reflects kinetic balance of two opposite processes, the rate of AGE compound formation and the rate of their degradation by means of receptors. AGE receptors participate in the elimination and change of aged, reticular and denaturated molecules of extracellular matrix as well as all other AGE molecules. However, in diabetes mellitus AGE protein accumulation may exceed the ability of their elimination due to chronic hyperglycemia and excessive glycation. AGE receptors were first detected on macrophage cells, and AGE protein binding to macrophage cell receptors is believed to cause a cascade of events in the homeostasis of blood vessel walls and their milieu by mediation of cytokines and tissue growth factors. At least four different AGE receptors have been described, among which two belong to the group of receptor scavengers. One of them is very similar, if not identical, to the receptor that internalizes altered LDL particles. Receptors on endothelium cells differ and these cell membrane sites bind AGE-ligands (denoted "RAGE" receptors). They belong to immunoglobulin receptor family and are prevalent in tissues. Binding of AGE compounds to RAGEs leads to cellular stress. It is not currently known whether variations in AGE level explain differences in susceptibility to develop complications, but it has been theorized that gene diversity in AGE receptors could offer an explanation.

Hyperglycemia induces a large number of alterations in vascular tissue that potentially promote accelerated atherosclerosis. Currently, in addition to the nonenzymatic glycosylation of proteins and lipids, two other major mechanisms have emerged that encompass most of the pathologic alterations observed in the vasculature of diabetic animals and humans: oxidative stress, protein kinase C (PKC) activation. Importantly, these mechanisms are not independent. For example, hyperglycemia-induced oxidative stress promotes the formation of AGEs and PKC activation, and both type 1 and type 2 diabetes are independent risk factors for coronary artery disease (CAD), stroke, and peripheral arterial disease. Schwartz C J, et al., "Pathogenesis of the atherosclerotic lesion. Implications for diabetes mellitus," *Diabetes Care* 15:1156-1167 (1992); Stamler 3, et al., "Diabetes, other risk factors, and 12-yr cardiovascular mortality for men screened in the Multiple Risk Factor Intervention Trial." *Diabetes Care* 16:434-444 (1993). Atherosclerosis accounts for virtually 80% of all deaths among North American diabetic patients, compared with one-third of all deaths in the general North American population, and more than 75% of all hospitalizations for diabetic complications are attributable to cardiovascular disease. American Diabetes Association, "Consensus statement: role of cardiovascular risk factors in prevention and treatment of macrovascular disease in diabetes," *Diabetes Care* 16:72-78 (1993).

The decline in heart disease mortality in the general U.S. population has been attributed to the reduction in cardiovascular risk factors and improvement in treatment of heart disease. However, patients with diabetes have not experienced the reduction in age-adjusted heart disease mortality that has been observed in nondiabetics, and an increase in age-adjusted heart disease mortality has been reported in diabetic women. Gu K, et al., "Diabetes and decline in heart disease mortality in U.S. adults," *JAMA* 281:1291-1297 (1999). Studies have also shown that diabetic subjects have more extensive atherosclerosis of both coronary and cerebral vessels than age- and sex-matched nondiabetic controls. Robertson W B, Strong J P, "Atherosclerosis in persons with hypertension and diabetes mellitus," *Lab Invest* 18:538-551 (1968). It has also been reported that diabetics have a greater number of involved coronary vessels and more diffuse distribution of atherosclerotic lesions. Waller B F, et al., "Status of the coronary arteries at necropsy in diabetes mellitus with onset after age 30 years. Analysis of 229 diabetic patients with and without clinical evidence of coronary heart disease and comparison to 183 control subjects," *Am J Med* 69:498-506 (1980). Large studies comparing diabetics with matched controls have also shown that diabetic patients with established CAD undergoing cardiac catheterization for acute myocardial infarction, angioplasty, or coronary bypass have significantly more severe proximal and distal CAD. Granger C B, et al., "Outcome of patients with diabetes mellitus and acute myocardial infarction treated with thrombolytic agents. The Thrombolysis and Angioplasty in Myocardial Infarction (TAMI) Study Group," *J Am Coll Cardiol* 21:920-925 (1993); Stein B, et al., "Influence of diabetes mellitus on early and late outcome after percutaneous transluminal coronary angioplasty," *Circulation* 91:979-989 (1995); Barzilay J I, et al., "Coronary artery disease and coronary artery bypass grafting in diabetic patients aged > or =65 years [report from the Coronary Artery Surgery Study (CASS) Registry]," *Am J Cardiol* 74:334-339 (1994)). Postmortem and angioscopic evidence also shows a significant increase in plaque ulceration and thrombosis in diabetic patients. Davies M J, et al., "Factors influencing the presence or absence of acute coronary artery thrombi in sudden ischaemic death," *Eur Heart J* 10:203-208 (1989); Silva J A, et al. "Unstable angina. A comparison of angioscopic findings between diabetic and nondiabetic patients," *Circulation* 92:1731-1736 (1995).

CAD is not confined to particular forms of diabetes, and is prevalent in both type 1 and type 2 diabetes. In type 1 diabetes, an excess of cardiovascular mortality is generally observed after the age of 30. Krolewski A S, et al., "Magnitude and determinants of coronary artery disease in juvenile-onset, insulin-dependent diabetes mellitus," *Am J Cardiol* 59:750-755 (1987). CAD risk was reported in this study to increase rapidly after age 40, and by age 55, 35% of men and women with type 1 diabetes die of CAD, a rate of CAD mortality that far exceeded that observed in an age-matched nondiabetic cohort. Id. Diabetic nephropathy in type 1 diabetics also increases the prevalence of CAD. Nephropathy leads to accelerated accumulation of AGEs in the circulation and tissue and parallels the severity of renal functional impairment. Makita Z, et al., "Advanced glycosylation end products in patients with diabetic nephropathy," *N Engl J Med* 325:836-842 (1991). In diabetic patients reaching end-stage renal disease, overall mortality has been reported to be greater than in nondiabetic patients with end-stage renal disease. The relative risk for age-specific death rate from myocardial infarction among all diabetic patients during the first year of dialysis is reportedly 89-fold higher than that of the general population. Geerlings W, et al., "Combined report on regular dialysis and transplantation in Europe, XXI," *Nephrol Dial Transplant* 6[Suppl 4]:5-29 (1991). It has also been reported that the most common cause of death in diabetic patients who have undergone renal transplantation is CAD, accounting for 40% of deaths in these patients. Lemmers M J, Barry J M, "Major role for arterial disease in morbidity and mortality after kidney transplantation in diabetic recipients," *Diabetes Care* 14:295-301 (1991).

With regard to people with type 2 diabetes, CAD is the leading cause of death, regardless of duration of diabetes. Stamler J, et al., "Diabetes, other risk factors, and 12-yr cardiovascular mortality for men screened in the Multiple Risk Factor Intervention Trial," *Diabetes Care* 16:434-444 (1993); Donahue R P, Orchard T J, "Diabetes mellitus and macrovascular complications. An epidemiological perspective," *Diabetes Care* 15:1141-1155 (1992). The increased cardiovascular risk is said to be particularly striking in women. Barrett-Connor E L, et al., "Why is diabetes mellitus a stronger risk factor for fatal ischemic heart disease in women than in men? The Rancho Bernardo Study," *JAMA* 265:627-631 (1991).

The degree and duration of hyperglycemia are the principal risk factors for microvascular complications in type 2 diabetes. The Diabetes Control and Complications Trial Research Group, "The effect of intensive treatment of diabetes on the development and progression of long-term complications in insulin-dependent diabetes mellitus," *N Engl J Med* 329:977-986 (1993). However, it has also been said that there is no clear association between the extent or severity of macrovascular complications and the duration or severity of the diabetes, and an increased prevalence of CAD is apparent in newly diagnosed type 2 diabetes subjects has been reported. Uusitupa M, et al., "Prevalence of coronary heart disease, left ventricular failure and hypertension in middle-aged, newly diagnosed type 2 (non-insulin-dependent) diabetic subjects," *Diabetologia* 28:22-27 (1985). It has also been reported that even impaired glucose tolerance carries an increased cardiovascular risk despite minimal hyperglycemia. Fuller J H, et al., "Coronary-heart-disease risk and impaired glucose tolerance. The Whitehall study," *Lancet* 1:1373-1376 (1980).

Insulin resistance is a common condition and, associated with genetic predisposition, sedentary lifestyle, and aging, it is exacerbated and produced by obesity. Thus, even in the absence of diabetes, insulin resistance is reportedly a major risk factor for CAD. Lempiainen P, et al., "Insulin resistance syndrome predicts coronary heart disease events in elderly nondiabetic men," *Circulation* 100:123-128 (1999). Impaired insulin action coupled with compensatory hyperinsulinemia leads to a number of proatherogenic abnormalities referred to as insulin resistance syndrome, and the association of insulin resistance with several established atherogenic risk factors apparently promotes atherosclerosis many years before overt hyperglycemia ensues. Ferrannini E, et al., "Insulin resistance in essential hypertension," *N Engl J Med* 317:350-357 (1987); Zavaroni I, et al., "Risk factors for coronary artery disease in healthy persons with hyperinsulinemia and normal glucose tolerance," *N Engl J Med* 320:702-706 (1989); Peiris A N, et al., "Adiposity, fat distribution, and cardiovascular risk," *Ann Intern Med* 110:867-872 (1989); Reaven G M, "Role of insulin resistance in human disease (syndrome X): an expanded definition," *Annu Rev Med* 44:121-131 (1993).

Dyslipidemia associated with insulin resistance entails elevated very-low-density lipoprotein (VLDL)-triglyceride levels, low high-density lipoprotein (HDL) levels, delayed postprandial clearance of triglyceride-rich lipoprotein remnants, and the presence of the very atherogenic, small, dense LDL particles. Grundy S M, "Hypertriglyceridemia, atherogenic dyslipidemia, and the metabolic syndrome," *Am J Cardiol* 81:18B-25B (1998). This atherogenic lipoprotein phenotype is the most common lipoprotein abnormality seen in patients with CAD and is said to impart a risk for CAD at least equal to that of isolated moderate to severe hypercholesterolemia. Austin M A, et al., "Atherogenic lipoprotein phenotype. A proposed genetic marker for coronary heart disease risk," *Circulation* 82:495-506 (1990). Insulin-resistant subjects also exhibit endothelial dysfunction and a hypercoagulable state, and chronic subclinical inflammation has emerged as part of the insulin-resistance syndrome. C-reactive protein, a marker of inflammation associated with cardiovascular events, is independently related to insulin sensitivity. Festa A, et al., "Chronic subclinical inflammation as part of the insulin resistance syndrome: the Insulin Resistance Atherosclerosis Study (IRAS)," *Circulation* 102:42-47 (2000). The proatherogenic metabolic risk factors in insulin-resistance subjects worsen continuously across the spectrum of glucose tolerance. Meigs J B, et al., "Metabolic risk factors worsen continuously across the spectrum of nondiabetic glucose tolerance. The Framingham Offspring Study," *Ann Intern Med* 128:524-533 (1998). Whether compensatory hyperinsulinemia promotes atherosclerosis in insulin-resistant subjects is not clear.

The atherogenic risk factor profile observed in insulin-resistance patients accounts for only a portion of the excess risk for CAD in patients with type 2 diabetes, indicating that hyperglycemia itself plays a central role in accelerating atherosclerosis in these patients. Thus, insulin-resistant individuals who go on to develop type 2 diabetes become exposed also to the atherogenic effects of hyperglycemia. Furthermore, while the threshold above which hyperglycemia becomes atherogenic is unknown, it may be in the range defined as impaired glucose tolerance. Gerstein H C, Yusuf S, "Dysglycaemia and risk of cardiovascular disease," *Lancet* 347:949-950 (1996). Various population-based studies in patients with type 2 diabetes are reported to have shown a positive association between the degree of glycemic control and CAD morbidity and mortality in middle-aged and elderly type 2 diabetic subjects. Turner R C, et al., "Risk factors for coronary artery disease in non-insulin dependent diabetes mellitus: United Kingdom Prospective Diabetes Study (UKPDS: 23)," *BMJ* 316:823-828 (1998); Kuusisto J, et al., "NIDDM and its metabolic control predict coronary heart disease in elderly subjects," *Diabetes* 43:960-967 (1994); Laakso M, "Hyperglycemia and cardiovascular disease in type 2 diabetes," *Diabetes* 48:937-942 (1999).

The metabolic abnormalities associated with types 1 and 2 diabetes also result in profound changes in the transport, composition, and metabolism of lipoproteins. Lipoprotein metabolism is said to be influenced by several factors including type of diabetes, glycemic control, obesity, insulin resistance, the presence of diabetic nephropathy, and genetic background. Ginsberg H N, "Lipoprotein physiology in nondiabetic and diabetic states. Relationship to atherogenesis," *Diabetes Care* 14:839-855 (1991). Abnormalities in plasma lipoprotein concentrations are commonly observed in diabetic individuals and reportedly contribute to the atherosclerotic process. The level of glycemic control is the major determinant of lipoprotein levels in type 1 diabetic patients. Garg A, "Management of dyslipidemia in IDDM patients," *Diabetes Care* 17:224-234 (1994). In well- to moderately-controlled diabetes, lipoprotein levels are usually within the normal range, while in poorly controlled type 1 diabetic patients, triglycerides are markedly elevated, LDL is modesty increased (usually when $HbA_{1c}$ is greater than 11%), and HDL levels are decreased.

In contrast to type 1 diabetes, the pathophysiology of dyslipidemia in type 2 diabetes results from a complex relationship between hyperglycemia and the insulin-resistance state. The typical lipoprotein profile associated with type 2 diabetes includes high triglycerides, low HDL levels, and normal LDL levels, the most consistent change reportedly being an increase in VLDL-triglyceride levels. Syvanne M, Taskinen M R, "Lipids and lipoproteins as coronary risk factors in non-insulin-dependent diabetes mellitus," *Lancet* 350:SI20-SI23 (1997); Ginsberg H N, "Diabetic dyslipidemia: basic mechanisms underlying the common hypertriglyceridemia and low HDL cholesterol levels," *Diabetes* 45[Suppl 3]:S27-S30 (1996). HDL levels are typically approximately 25% to 30% lower than in nondiabetic subjects and are commonly associated with other lipid and lipoprotein abnormalities, particularly high triglyceride levels.

Hypertriglyceridemia in type 2 diabetes results from high fasting and postprandial triglyceride-rich lipoproteins, especially VLDL. Type 2 diabetic subjects with hypertriglyceridemia have both overproduction and impaired catabolism of VLDL. Increased VLDL production is almost uniformly present in patients with type 2 diabetes and hypertriglyceridemia. Increased VLDL production in diabetes is a consequence of an increase in free fatty acid mobilization (because maintenance of stored fat in adipose tissue depends on the suppression of hormone-sensitive lipase by insulin) and high glucose levels. Because free fatty acid availability is a major determinant of VLDL production by the liver, VLDL overproduction and hypertriglyceridemia occur.

The rest of the dyslipidemic phenotype that characterizes insulin resistance and type 2 diabetes (low HDL and small, dense LDL)—which has been termed atherogenic lipoprotein phenotype (Austin M A, et al, "Atherogenic lipoprotein phenotype. A proposed genetic marker for coronary heart disease risk," *Circulation* 82:495-506 (1990))—follows once VLDL secretion increases, mainly through the action of cholesteryl ester transfer protein and lipoprotein compositional changes that occur in plasma. Ginsberg H N, "Insulin resistance and cardiovascular disease," *J Clin Invest* 106:453-458 (2000). Increased fatty acid flux to the liver also results in the production of large triglyceride-rich VLDL particles because the size of VLDL is also mainly determined by the amount of triglyceride available. VLDL size is an important determinant of its metabolic fate and large triglyceride-rich VLDL particles may be less efficiently converted to LDL, thereby increasing direct removal from the circulation by non-LDL pathways. In addition, overproduction of large triglyceride-rich VLDL is said to be associated with the atherogenic small, dense LDL subclass.

In type 2 diabetic subjects with more severe hypertriglyceridemia, VLDL clearance by lipoprotein lipase (LPL)—the rate-limiting enzyme responsible for the removal of plasma triglyceride-rich lipoproteins—is also reported to be impaired. Syvanne M, Taskinen M R, "Lipids and lipoproteins as coronary risk factors in non-insulin-dependent diabetes mellitus," *Lancet* 350:SI20-SI23 (1997). LPL requires insulin for maintenance of normal tissue levels, and its activity is low in patients with poorly controlled type 2 diabetes. The result is enzymatic activity insufficient to match the overproduction rate, with further accumulation of VLDL triglyceride.

Triglyceride concentrations are associated with premature CAD, and studies have shown that triglyceride-rich lipoproteins play an important role in the progression of atherosclerosis. Hodis H N, "Myocardial ischemia and lipoprotein lipase activity," *Circulation* 102:1600-1601 (2000). Furthermore, in contrast to the controversy regarding hypertriglyceridemia as a risk factor for coronary heart disease (CHD) in the nondiabetic population, several studies indicate that elevated triglyceride levels are independently associated with increased CHD risk in diabetic patients. Hypertriglyceridemia in diabetic patients often correlates with LDL density and subclass (i.e., small, dense LDL) and decreased levels of $HDL_2$, which appear to increase overall risk synergistically. Havel R J, Rapaport E, "Management of primary hyperlipidemia," *N Engl J Med* 332:1491-1498 (1995).

Characterized by increased VLDL production and impaired removal, it has been reported that patients with type 2 diabetes exhibit excessive postprandial lipemia and impaired remnant clearance. Exaggerated postprandial lipemia resulting from impaired remnant clearance is a factor in atherogenesis, involving endothelial dysfunction and enhanced oxidative stress. Karpe F, "Postprandial lipoprotein metabolism and atherosclerosis," *J Intern Med* 246:341-355 (1999); Zilversmit D B, "Atherogenesis: a postprandial phenomenon," *Circulation* 60:473-485 (1979); Patsch J R, et al., "Relation of triglyceride metabolism and coronary artery disease. Studies in the postprandial state," *Arterioscler Thromb* 12:1336-1345 (1992); Plotnick G D, et al., "Effect of antioxidant vitamins on the transient impairment of endothelium-dependent brachial artery vasoactivity following a single high-fat meal," *JAMA* 278:1682-1686 (1997). Postprandial lipemia consists of a heterogeneous group of triglyceride-rich particles of different composition and origin. Although 80% of the increase in postprandial triglyceride levels is accounted for by chylomicrons (which carry a large number of triglyceride molecules), the number of endogenous (liver-derived) VLDL constitutes over 90% of the triglyceride-rich particles in the postprandial state. Delayed VLDL clearance results in the accumulation of partially catabolized VLDL remnants that are reduced in size and enriched in cholesteryl ester, and evidence is said to indicate that these small, cholesteryl ester-enriched VLDL particles are atherogenic.

As in nondiabetic subjects, low high-density lipoprotein (HDL) levels are said to be powerful indicators of CHD in diabetic patients. Decreased HDL levels in diabetes result from decreased production and increased catabolism of HDL and are closely related to the abnormal metabolism of triglyceride-rich lipoproteins. In insulin-resistant patients with or without overt type 2 diabetes, the composition of LDL particles is altered, resulting in a preponderance of small, triglyceride-enriched and cholesterol-depleted particles (phenotype B). A preponderance of small, dense LDL particles is related to many characteristics of insulin-resistance syndrome, and in nondiabetic subjects, LDL subclass phenotype B is associated with other components of insulin-resistance syndrome, including central obesity, hypertension, glucose intolerance, and hyperinsulinemia. Selby J V, et al., "LDL subclass phenotypes and the insulin resistance syndrome in women," *Circulation* 88:381-387 (1993); Reaven G M, et al., "Insulin resistance and hyperinsulinemia in individuals with small, dense low density lipoprotein particles," *Clin Invest* 92:141-146 (1993); Haffner S M, et al., "LDL size in African Americans, Hispanics, and non-Hispanic whites: the insulin resistance atherosclerosis study," *Arterioscler Thromb Vasc Biol* 19:2234-2240 (1999).

The formation of small, dense LDL in diabetes occurs in a similar fashion to the increased formation of small and dense $HDL_3$. Cholesteryl ester transfer protein mediates the exchange of triglyceride from VLDL for cholesteryl ester in LDL. If sufficient LDL cholesteryl ester is replaced by triglyceride from VLDL, then when the particle comes into contact with hepatic lipase hydrolysis of newly acquired triglyceride in LDL and HDL by HTGL in turn decreases the size of LDL particles. Packard C J, Shepherd J, "Lipoprotein heterogeneity and apolipoprotein B metabolism," *Arterioscler Thromb Vasc Biol* 17:3542-3556 (1997). Small, dense LDL has also been said to be associated with CAD risk independently of the absolute concentrations of LDL cholesterol or other CAD risk factors, small, dense LDL particles being more susceptible to oxidative modification. Tribble D L, et al., "Oxidative susceptibility of low density lipoprotein subfractions is related to their ubiquinol-10 and alpha-tocopherol content," *Proc Natl Acad Sci USA* 91:1183-1187 (1994). They are also particularly prone to induce endothelial dysfunction. Anderson T J, et al., "Endothelium-dependent coronary vasomotion relates to the susceptibility of LDL to oxidation in humans," *Circulation* 93:1647-1650 (1996). In addition, there is enhanced arterial wall penetration by small LDL particles. Nielsen L B, "Transfer of low density lipoprotein into the arterial wall and risk of atherosclerosis," *Atherosclerosis* 123:1-15 (1996).

Glycosylation occurs both on the apoB and phospholipid components of LDL, and is said to result in profound functional alternations in LDL clearance and susceptibility to oxidative modification, Bucala R, et al., "Identification of the major site of apolipoprotein B modification by advanced glycosylation end products blocking uptake by the low density lipoprotein receptor," *J Biol Chem* 270:10828-10832 (1995); Bucala R, et al., "Lipid advanced glycosylation: pathway for lipid oxidation in vivo," *Proc Natl Acad Sci USA* 90:6434-6438 (1993). Clinical studies have reportedly shown an increased level of AGEs on LDL obtained from diabetics compared with healthy individuals. Bucala R, et al., "Modification of low density lipoprotein by advanced glycation end products contributes to the dyslipidemia of diabetes and renal insufficiency," *Proc Natl Acad Sci USA* 91:9441-9445 (1994). Glycosylation of LDL apoB occurs mainly on a positively charged lysine residue within the putative LDL receptor binding domain, which is essential for the recognition of LDL by the LDL receptor. Id. LDL glycosylation increases with glucose levels and impairs LDL receptor-mediated LDL clearance.

Another atherogenic effect of glycation is to increase LDL susceptibility to oxidative modification. Advanced glycosylation of an amine-containing phospholipid component of LDL is accompanied by progressive oxidative modification of unsaturated fatty acid residues. Thus, glycation is said to also confer increased susceptibility of LDL to oxidative modification, which has been considered a critical step in its atherogenicity. Lyons T J, "Glycation and oxidation: a role in the pathogenesis of atherosclerosis," *Am J Cardiol* 71:26B-31B (1993); Bowie A, et al., "Glycosylated low density lipoprotein is more sensitive to oxidation: implications for the diabetic patient?," *Atherosclerosis* 102:63-67 (1993).

Cholesterol lowering using agents such as pravastatin have been reported to reduce the absolute risk of coronary events for diabetic patients. Goldberg R B, et al., "Cardiovascular events and their reduction with pravastatin in diabetic and glucose-intolerant myocardial infarction survivors with average cholesterol levels: subgroup analyses in the Cholesterol and Recurrent Events (CARE) trial," *Circulation* 98:2513-2519 (1998). However, the absolute clinical benefit achieved by cholesterol lowering may be greater in diabetic than in nondiabetic patients with CAD because diabetic patients have a higher absolute risk of recurrent CAD and higher case fatality rates, or because LDL cholesterol in diabetic patients is more atherogenic. Aronson D, et al., "Mechanisms determining course and outcome of diabetic patients who have had acute myocardial infarction," *Ann Intern Med* 126:296-306 (1997).

The American Diabetes Association recommendations for the management of hyperlipidemia in patients with diabetes generally follow the guidelines of the National Cholesterol Education Program with several differences. American Diabetes Association. Position statement. "Management of dyslipidemia in adults with diabetes," *Diabetes Care* 21:179-182 (1998). Non-pharmacologic strategies to treat dyslipidemia in diabetics include dietary modification (similar to those recommended by the National Cholesterol Education Program), weight loss, physical exercise, and improved glycemic control. Id. In patients with type 1 diabetes, optimal glycemic control should result in normal or below normal lipoprotein levels and prevent the atherogenic state associated with lipoprotein glycosylation. Improved diabetic control in type 2 diabetes is beneficial but not always associated with reversal of lipoprotein abnormalities.

Improved glycemic control using pharmacologic agents such as sulfonylureas, insulin, metformin (N,N-dimethylimidodicarbonimidic diamide hydrochloride), or thiazolidinediones can also help. The magnitude of improvement in triglycerides generally correlates with the change in glucose levels rather than the mode of therapy. However, agents that improve insulin sensitivity such as metformin and thiazolidinediones can also lead to lower triglycerides. In addition, "perfect" glycemic control is not attained in many type 2 diabetic patients, and relatively recent publications have argued against the relevance of the traditional classification to primary and secondary CHD prevention in the setting of diabetes. Haffner S M, "Management of dyslipidemia in adults with diabetes," *Diabetes Care* 21:160-178 (1998); Haffner S M, et al. "Mortality from coronary heart disease in subjects with type 2 diabetes and in nondiabetic subjects with and without prior myocardial infarction," *N Engl J Med* 339:229-234 (1998). The rationale stems from both the high event rates in diabetic patients without clinical evidence of CAD (presumably because of the high rates of subclinical atherosclerosis), as well as the worse prognosis in diabetic patients who have had a clinical event compared with nondiabetic subjects, leading to the suggestion that LDL cholesterol should be lowered to less than 100 mg per dL in diabetic subjects without prior CAD. Id.

Endothelial cells situated at the vessel wall-blood interface participate in a number of important homeostatic and cellular functions that protect from atherosclerosis and intraluminal thrombosis. Endothelial dysfunction can promote both the formation of atherosclerotic plaques and the occurrence of acute events and, in diabetes, is said to entail profound perturbations in several critical functions of the endothelium that contribute to the initiation and progression of the atherosclerotic process, as well as to the occurrence of clinical events. It is believed that diabetes results in weakened intercellular junctions, and that AGEs diminish endothelial barrier function. The endothelial lining of the large arteries is of the continuous type characterized by tight junctions in the lateral borders, which restrict the movement of macromolecules from reaching the subendothelial space.

Leukocyte adhesion to the vascular endothelium also contributes to diabetic complications. Among the earliest events in atherogenesis is the binding of mononuclear leukocytes to the endothelium with subsequent entry into the vessel wall. This is mediated through the expression of inducible adhesion molecules on the endothelial cell surface. Hyperglycemia stimulates the expression of vascular cell adhesion molecule-1 (VCAM-1) and E selectin. In addition, AGE interaction with the AGE receptor has been reported to result in the induction of oxidative stress and, consequently, of the transcription factor NF-kappaB and VCAM-1. Thus, early events in the atherosclerosis process in diabetes may be mediated through enhanced adhesive interactions of monocytes with the endothelial surface.

Impaired endothelium-dependent relaxation, which is mediated through the release of endothelium-derived relaxing factor (EDRF), is also reportedly a consistent finding in animal models and in human diabetes and occurs in a variety of vascular beds, including the coronary arteries. Impaired endothelium-dependent relaxation has been demonstrated in both type 1 and type 2 diabetes in the absence of clinical complications, while endothelium-independent vasodilation is preserved, and impaired endothelium-dependent relaxation can be demonstrated in insulin-resistant subjects with normal glucose tolerance. De Vriese A S, et al., "Endothelial dysfunction in diabetes," *Br J Pharmacol* 130:963-974 (2000). Thus, hyperglycemia is recognized as the primary mediator of diabetic endothelial dysfunction. Williams S B, et al., "Acute hyperglycemia attenuates endothelium-dependent vasodilation in humans in vivo," *Circulation* 97:1695-1701 (1998). Similar to the mechanism of endothelial dysfunction observed in hypercholesterolemia, hyperglycemia-induced endothelial dysfunction is thought to result primarily from increased generation of oxygen free radicals that inactivate EDRF. Insulin resistance is also said to contribute to endothelial dysfunction in diabetic patients. Steinberg H O, et al., "Obesity/insulin resistance is associated with endothelial dysfunction. Implications for the syndrome of insulin resistance," *J Clin Invest* 97:2601-2610 (1996).

Diabetes is also said to be characterized by a variety of individual alterations in the coagulation and fibrinolytic systems that combine to produce a prothrombotic state. These alterations include increased platelet functional behavior, increased levels of several coagulation components, and impaired fibrinolysis. The coagulation and fibrinolytic systems are said to be especially important in atherosclerosis because of the substantial contribution that mural thrombosis may make to the later stages of plaque progression, and because thrombotic occlusion plays a vital role in the development of clinical events. In the vast majority of cases, the fundamental mechanism in the development of potentially life-threatening events such as unstable angina or myocardial infarction is thrombosis arising at sites of plaque disruption.

Platelet hyperaggregability, including the presence of spontaneous platelet aggregation and increased platelet aggregability induced by conventional stimuli, also increases the risk for cardiovascular events. Platelets from diabetic subjects exhibit enhanced adhesiveness and hyperaggregability, and shear-induced platelet adhesion and aggregation are also increased in diabetic patients. Knobler H, et al., "Shear-induced platelet adhesion and aggregation on subendothelium are increased in diabetic patients," *Thromb Res* 90:181-190 (1998). von Willebrand factor (vWF) is involved in the initial adhesion of platelets to the subendothelium of injured vessel wall and is among the most important adhesive molecules mediating hemostatic interactions between platelets and vessel wall components. Synthesized and secreted by endothelial cells, high circulating levels of vWF are considered markers of endothelial dysfunction. In diabetic patients plasma concentrations of vWF are elevated and are closely associated with the presence of vascular complications and endothelial dysfunction. Stehouwer C D, et al., "Urinary albumin excretion, cardiovascular disease, and endothelial dysfunction in non-insulin-dependent diabetes mellitus," *Lancet* 340:319-323 (1992). Epidemiologic data have also demonstrated a relation between plasma vWF and insulin-resistance syndrome. Conlan M G, et al., "Associations of factor VIII and von Willebrand factor with age, race, sex, and risk factors for atherosclerosis. The Atherosclerosis Risk in Communities (ARIC) Study," *Thromb Haemost* 70:380-385 (1993). Increased plasma concentration of vWF has been shown to be predictive of re-infarction and mortality in survivors of myocardial infarction, of cardiac events in healthy people and in patients with angina pectoris. The European Concerted Action on Thrombosis study showed that vWF predictability was not affected by the adjustment with other classical coronary risk factors such as body mass index, lipid disorders or smoking. As vWF levels are dependent on the acute phase reaction like fibrinogen, and vWF correlates positively with fibrinogen or C-reactive protein levels, it has to be evaluated if vWF is a risk factor irrespective of fibrinogen level. In type 2 diabetic patients vWF levels are higher in microalbuminuric patients. vWF is reportedly poorly or not at all related to insulin resistance.

Hyperactive platelets may form microaggregates leading to capillary microembolization. In patients with diabetes the resulting relative tissue hypoxia may in the long-term precede clinically detectable microangiopathy. It has been speculated that microembolization of the vasa vasorum of the large vessels by hyperactive platelets may also be the initial event in the development of atherosclerosis. Secretion of mitogenic, oxidative or vasoconstrictive substances by platelets activated in response to endothelial injury amplifies and accelerates the progression of atherosclerosis. Acute thrombotic events in the arterial circulation are also triggered by platelets.

The fibrinolytic system is natural defense against thrombosis. A balance exists between plasminogen activators and inhibitors, and impairment of this balance can be caused either by diminished release of tissue plasminogen activator (t-PA) or increased levels of plasminogen activator inhibitor 1 (PAI-1). PAI-1 is a serine protease inhibitor and evidence suggests that it is the major regulator of the fibrinolytic system. It binds and rapidly inhibits both single- and two-chain t-PA and urokinase. t-PA and PAI-1 rapidly form an inactive irreversible complex. Abnormalities of the fibrinolytic system have been described in both type 1 and type 2 diabetes. Impaired fibrinolysis, as described in diabetes type 2, is commonly accompanied by an increased plasma levels of PAI-1 and by increased concentration of t-PA antigen, which reflects predominantly t-PA/PAI-1 complexes. In type 1 diabetes results are mixed, and diminished, normal and enhanced fibrinolysis have all been reported. In subjects with type 2 diabetes a variety of risk factors are independently associated with impaired fibrinolysis: obesity, hypertension, dyslipidaemia, glucose intolerance, hyperinsulinaemia and insulin resistance. These factors often tend to converge and numerous studies have attempted to dissect out the independent contribution of the above risk factors in determining fibrinolytic activity in diabetes, but this task has been hampered by the complex relationship between them. In non-diabetic subjects, insulin resistance is paralleled by increased insulin and both correlate with triglyceride levels. Thus any one or more of these variables may explain interrelationship with PAI-1. By contrast in type 2 diabetes, insulin resistance, insulin concentration and triglyceride levels are less tightly interdependent in explaining increased PAI-1. Impaired fibrinolysis not only predisposes to thrombotic events but also plays a role in the formation and progression of atherosclerotic lesions. Increased synthesis of PAI-1 has been demonstrated in atherosclerotic lesions. This may lead to fibrin deposition during lesion rupture, contributing to the progression of the lesion. PAI-1 within the lesion inhibits plasmin formation, which plays an important role in cleaving extracellular matrix proteins, directly or via activation of metalloproteinases. This may lead to stabilization and further growth of atherosclerotic lesion. Changes in the fibrinolytic system also play an important role in microangiopathy. Urokinase and plasmin are activators of latent metalloproteinases, such as collagenases, that are responsible for proteolysis of extracellular matrix proteins. Increased PAI-1 may lead to basement membrane thickening observed in microangiopathy.

A large body of evidence also indicates strong independent direct correlation between high fibrinogen plasma levels and an increased risk of CAD. Fibrinogen levels are often increased in diabetes, and this elevation is associated with poor glycemic control. Kannel W B, et al., "Diabetes, fibrinogen, and risk of cardiovascular disease: the Framingham Experience," *Am Heart J* 120:672-676 (1990). The intensity of endogenous fibrinolysis depends on a dynamic equilibrium involving plasminogen activators, primarily tissue-type plasminogen activator, and inhibitors. The principal physiologic inhibitor of tissue-type plasminogen activator is plasminogen activator inhibitor-1 (PAI-1). Attenuated fibrinolysis caused by an increase of PAI-1 activity has been associated with increased risk for myocardial infarction in patients with established CAD. Kohler H P, Grant P J, "Plasminogen-activator inhibitor type 1 and coronary artery disease," *N Engl J Med* 342:1792-1801 (2000). Reduced plasma fibrinolytic activity caused by increased PAI-1 levels is a characteristic feature of insulin resistance and hyperinsulinemia. Elevated concentrations of PAI-1 have been recognized consistently in the plasma of hyperinsulinemic type 2 diabetics but occur also in normoglycemic insulin-resistant subjects. Juhan-Vague I, Alessi M C, "PAI-1, obesity, insulin resistance and risk of cardiovascular events," *Thromb Haemost* 78:656-660 (1997). The production of PAI-1 by adipose tissue has been demonstrated and could be an important contributor to the elevated plasma PAI-1 levels observed in insulin-resistant patients. Alessi M C, et al., "Production of plasminogen activator inhibitor 1 by human adipose tissue: possible link between visceral fat accumulation and vascular disease," *Diabetes* 46:860-867 (1997). Hyperglycemia can also increase PAI-1 levels because it stimulates transcription of the PAI-1 gene through an effect on its promoter region. Chen Y Q, et al., "Sp1 sites mediate activation of the plasminogen activator inhibitor-1 promoter by glucose in vascular smooth muscle cells," *J Biol Chem* 273:8225-8231 (1998). Although it is possible that some of the hemostatic abnormalities in diabetes are partly markers of underlying vascular disease rather than the primary abnormalities, the clotting and fibrinolytic profile of diabetic patients is said to bear a striking similarity to that of patients at high risk for future cardiovascular events. The prothrombotic state in diabetes is said to help explain the observation that intracoronary thrombus formation is more frequently found by angioscopic examination in diabetic patients with unstable angina, and its clinical correlate, the higher risk of adverse outcome, namely death, nonfatal infarction, or recurrent unstable angina. Silva J A, et al., "Unstable angina. A comparison of angioscopic findings between diabetic and nondiabetic patients," *Circulation* 92:1731-1736 (1995); Aronson D, et al., "Mechanisms determining course and outcome of diabetic patients who have had acute myocardial infarction," *Ann Intern Med* 126:296-306 (1997); Malmberg K, et al., "Impact of diabetes on long-term prognosis in patients with unstable angina and non-Q-wave myocardial infarction: results of the OASIS (Organization to Assess Strategies for Ischemic Syndromes) Registry," *Circulation* 102:1014-1019 (2000); Calvin J E, et al., "Risk stratification in unstable angina. Prospective validation of the Braunwald classification," *JAMA* 273:136-141 (1995). Thus, hyperglycemia induces a large number of alterations in vascular tissue that potentially promote accelerated atherosclerosis. Acosta J, et al., "Molecular basis for a link between complement and the vascular complications of diabetes," *Proc Natl Acad Sci USA* 97:5450-5455 (2000).

Protein kinase C is also involved and the metabolic consequences of hyperglycemia are said to be seen in cells in which glucose transport is largely independent of insulin. The resulting intracellular hyperglycemia has been implicated in the pathogenesis of diabetic complications through the activation of the PKC system. Ishii H, et al., "Amelioration of vascular dysfunctions in diabetic rats by an oral PKC beta inhibitor," *Science* 272:728-731 (1996); Koya D, King G L, "Protein kinase C activation and the development of diabetic complications," *Diabetes* 47:859-866 (1998). High ambient glucose concentrations activate PKC by increasing the formation of diacylglycerol (DAG), the major endogenous cellular cofactor for PKC activation, from glycolytic intermediates such as dihydroxy-acetone phosphate and glyceraldehyde-3-phosphate. The elevation of DAG and subsequent activation of PKC in the vasculature can be maintained chronically. Xia P, et al., "Characterization of the mechanism for the chronic activation of diacylglycerol-protein kinase C pathway in diabetes and hypergalactosemia," *Diabetes* 43:1122-1129 (1994).

PKC is a family of at least 12 isoforms of serine and threonine kinases. Although several PKC isoforms are reportedly expressed in vascular tissue, in the rat model of diabetes there is a preferential activation of PKC b2 in the aorta, heart, and retina, and PKC b1 in the glomeruli. Inoguchi T, et al., "Preferential elevation of protein kinase C isoform beta II and diacylglycerol levels in the aorta and heart of diabetic rats: differential reversibility to glycemic control by islet cell transplantation," *Proc Natl Acad Sci USA* 89:11059-11063 (1992); Koya D, et al., "Characterization of protein kinase C beta isoform activation on the gene expression of transforming growth factor-beta, extracellular matrix components, and prostanoids in the glomeruli of diabetic rats," *J Clin Invest* 100:115-126 (1997). The PKC system is ubiquitously distributed in cells and is involved in the transcription of several growth factors and in signal transduction in response to growth factors. In vascular smooth muscle cells, PKC activation has been reported to modulate growth rate, DNA synthesis, and growth factor receptor turnover. PKC activation increases the expression of transforming growth factor-b (TGF-b), which is one of the most important growth factors, regulating extracellular matrix production by activating gene expression of proteoglycans and collagen and decreasing the synthesis of proteolytic enzymes that degrade matrix proteins. Increased expression of TGF-b is thought to lead to thickening of capillary basement membrane, one of the early structural abnormalities observed in almost all tissues in diabetes. PKC b selective inhibitor (LY333531) attenuates glomerular expression of TGF-b and extracellular matrix proteins such as fibronectin and type IV collagen. Koya, supra; Koya D, et al., "Amelioration of accelerated diabetic mesangial expansion by treatment with a PKC beta inhibitor in diabetic db/db mice, a rodent model for type 2 diabetes," *FASEB J* 14:439-447 (2000). Hyperglycemia-induced PKC activation also results in increased platelet-derived growth factor-b receptor expression on smooth muscle cells and other vascular wall cells (e.g., endothelial cells, monocyte-macrophages). Inaba T, et al., "Enhanced expression of platelet-derived growth factor-beta receptor by high glucose. Involvement of platelet-derived growth factor in diabetic angiopathy," *Diabetes* 45:507-512 (1996).

Oxidative stress is widely invoked as a pathogenic mechanism for atherosclerosis. Among the sequelae of hyperglycemia, oxidative stress has been suggested as a potential mechanism for accelerated atherosclerosis. Baynes J W, Thorpe S R, "Role of oxidative stress in diabetic complications: a new perspective on an old paradigm," *Diabetes* 48:1-9 (1999). Importantly, there appears to be a strong pathogenic link between hyperglycemia-induced oxidant stress and other hyperglycemia-dependent mechanisms of vascular damage, namely AGEs formation and PKC activation), and hyperglycemia can increase oxidative stress through several pathways. A major mechanism appears to be the hyperglycemia-induced intracellular reactive oxygen species, produced by the proton electromechanical gradient generated by the mitochondrial electron transport chain and resulting in increased production of superoxide. Nishikawa T, et al., "Normalizing mitochondrial superoxide production blocks three pathways of hyperglycaemic damage," *Nature* 404:787-790 (2000). Two other mechanisms have been proposed that may explain how hyperglycemia causes increased reactive oxygen species formation. One mechanism involves the transition metal-catalyzed autoxidation of free glucose, as described in cell-free systems. Through this mechanism, glucose itself initiates an autoxidative reaction and free radical production yielding superoxide anion ($O_2^-$) and hydrogen peroxide ($H_2O_2$). Wolff S P, "Diabetes mellitus and free radicals. Free radicals, transition metals and oxidative stress in the aetiology of diabetes mellitus and complications," *Br Med Bull* 49:642-652 (1993). The other mechanism involves the transition metal-catalyzed autoxidation of protein-bound Amadori products, which yields superoxide and hydroxyl radicals and highly reactive dicarbonyl compounds. Baynes J W, Thorpe S R, "Role of oxidative stress in diabetic complications: a new perspective on an old paradigm," *Diabetes* 48:1-9 (1999).

There is also evidence that hyperglycemia may compromise natural antioxidant defenses. Under normal circumstances, free radicals are rapidly eliminated by antioxidants such as reduced glutathione, vitamin C, and vitamin E. Reduced glutathione content, as well as reduced vitamin E, have been reported in diabetic patients. Yoshida K, et al., "Weakened cellular scavenging activity against oxidative stress in diabetes mellitus: regulation of glutathione synthesis and efflux," *Diabetologia* 38:201-210 (1995); Karpen C W, et al., "Production of 12-hydroxyeicosatetraenoic acid and vitamin E status in platelets from type I human diabetic subjects," *Diabetes* 34:526-531 (1985).

The interaction between AGE epitopes and the cell surface AGE receptor up-regulate oxidative stress response genes and release oxygen radicals. Thus, hyperglycemia simultaneously enhances both AGEs formation and oxidative stress, and the mutual facilitatory interactions between glycation and oxidation chemistry can contribute synergistically to the formation of AGEs, oxidative stress, and diabetic complications. Indeed, there are reportedly strong correlations between levels of glycoxidation products in skin collagen and the severity of diabetic retinal, renal, and vascular disease. Beisswenger P J, et al., "Increased collagen-linked pentosidine levels and advanced glycosylation end products in early diabetic nephropathy," *J Clin Invest* 92:212-217 (1993). Oxidative stress may also be involved in the activation of DAG-PKC in vascular tissue. Nishikawa T, et al., "Normalizing mitochondrial superoxide production blocks three pathways of hyperglycaemic damage," *Nature* 404:787-790 (2000). Oxidants produced in the setting of hyperglycemia can activate PKC. Konishi H, et al., "Activation of protein kinase C by tyrosine phosphorylation in response to H2O2," *Proc Natl Acad Sci USA* 94:11233-11237 (1997).

The risk for congestive heart failure (CHF) and idiopathic cardiomyopathy is also said to be strongly increased in diabetes. Kannel W B, et al., "Role of diabetes in congestive heart failure: the Framingham study," *Am J Cardiol* 34:29-34 (1974); Shindler D M, et al., "Diabetes mellitus, a predictor of morbidity and mortality in the Studies of Left Ventricular Dysfunction (SOLVD) Trials and Registry," *Am J Cardiol* 77:1017-1020 (1996); Ho K K, et al., "The epidemiology of heart failure: the Framingham Study," *J Am Coll Cardiol* 22:6A-13A (1993). Although data on the effect of diabetes on the prognosis of patients with CHF are limited, several studies implicate diabetes as an independent predictor of poor prognosis in this setting. In the Studies of Left Ventricular Dysfunction study, diabetes was an independent predictor of morbidity and mortality in patients with symptomatic heart failure, asymptomatic patients with an ejection fraction less than or equal to 35%, and in the registry population. Shindler, supra. One reason for the poor prognosis in patients with both diabetes and ischemic heart disease seems to be an enhanced myocardial dysfunction leading to accelerated heart failure. Grundy S M, et al., "Diabetes and cardiovascular disease: a statement for healthcare professionals from the American Heart Association," *Circulation* 100:1134-1146 (1999).

The cardiomyopathic process associated with diabetes mellitus manifests initially as diminished left ventricular compliance in the presence of normal left ventricular systolic function. Zarich S W, et al., "Diastolic abnormalities in young asymptomatic diabetic patients assessed by pulsed Doppler echocardiography," *J Am Coll Cardiol* 12:114-120 (1988); Paillole C, et al., "Prevalence and significance of left ventricular filling abnormalities determined by Doppler echocardiography in young type I (insulin-dependent) diabetic patients," *Am J Cardiol* 64:1010-1016 (1989); Mildenberger R R, et al., "Clinically unrecognized ventricular dysfunction in young diabetic patients," *J Am Coll Cardiol* 4:234-238 (1984). Diastolic abnormalities occur in 27% to 69% of asymptomatic diabetic patients. A lower ejection fraction in response to dynamic exercise in the presence of a normal resting ejection fraction has been demonstrated in several studies, indicating that contractile reserve is decreased in many asymptomatic patients with diabetes. Mildenberger, supra; Shapiro L M, et al., "Left ventricular function in diabetes mellitus. II: Relation between clinical features and left ventricular function," *Br Heart J* 45:129-132 (1981); Mustonen J N, et al., "Left ventricular systolic function in middle-aged patients with diabetes mellitus," *Am J Cardiol* 73:1202-1208 (1994). Systolic dysfunction may appear, usually in patients with long-standing disease who suffer from advanced microvascular complications. Racy D C, "Which left ventricular function is impaired earlier in the evolution of diabetic cardiomyopathy? An echocardiographic study of young type I diabetic patients," *Diabetes Care* 17:633-639 (1994). However, even subclinical cardiomyopathy with reduced myocardial reserve may become clinically important in the presence of myocardial ischemia or with coexistent uncontrolled hypertension. Stone P H, et al., "The effect of diabetes mellitus on prognosis and serial left ventricular function after acute myocardial infarction: contribution of both coronary disease and diastolic left ventricular dysfunction to the adverse prognosis. The MILTS Study Group," *J Am Coll Cordial* 14:49-57 (1989).

It is also understood that the coexistence of hypertension and diabetes exerts a particularly deleterious effect on the heart. The coexistence of hypertension has been considered a major factor in the expression of diastolic dysfunction in diabetic patients. Grossman E, Messerli F H, "Diabetic and hypertensive heart disease," *Ann Intern Med* 125:304-310

(1996). In hypertensive subjects, diabetes is an important precursor of CHF, with a greater relative risk in women than in men. Levy D, et al., "The progression from hypertension to congestive heart failure," *JAMA* 275:1557-1562 (1996). The mechanisms responsible for the increased risk for the development of CHF are not fully understood, but may be related in part to an exaggerated increase in left ventricular mass. Grossman E, et al., "Left ventricular mass in diabetes-hypertension," *Arch Intern Med* 152:1001-1004 (1992).

Obesity, which is characterized by insulin resistance and hyperinsulinemia, is also strongly correlated with increased left ventricular mass independent of age and blood pressure. Lauer M S, et al., "The impact of obesity on left ventricular mass and geometry. The Framingham Heart Study," *JAMA* 266:231-236 (1991). Furthermore, left ventricular mass in normotensive obese subjects is related more to the severity of insulin resistance than to the obesity itself as expressed by the body mass index. Sasson Z, et al., "Insulin resistance is an important determinant of left ventricular mass in the obese," *Circulation* 88:1431-1436 (1993).

In hypertensive patients with normal glucose tolerance, who commonly exhibit insulin resistance and hyperinsulinemia, left ventricular mass has been shown to correlate with the degree of insulin resistance. Ohya Y, et al., "Hyperinsulinemia and left ventricular geometry in a work-site population in Japan," *Hypertension* 27:729-734 (1996); Verdecchia P, et al., "Circulating insulin and insulin growth factor-1 are independent determinants of left ventricular mass and geometry in essential hypertension," *Circulation* 100:1802-1807 (1999). A similar association is also observed in nonhypertensive insulin-resistant subjects. Marcus R, et al., "Sex-specific determinants of increased left ventricular mass in the Tecumseh Blood Pressure Study," *Circulation* 90:928-936 (1994).

Thus, hypertension, insulin resistance, hyperinsulinemia, and type 2 diabetes are all reported to be commonly associated and result in a high risk for cardiovascular complications. Reaven G M, Laws A, "Insulin resistance, compensatory hyperinsulinaemia, and coronary heart disease," *Diabetologia* 37:948-952 (1994); Agewall S, et al., "Carotid artery wall intima-media thickness is associated with insulin-mediated glucose disposal in men at high and low coronary risk," *Stroke* 26:956-960 (1995). Left ventricular mass is a strong predictor of cardiac and cerebrovascular morbidity independent of blood pressure or other risk factors, as well as a powerful risk factor for the development of symptomatic CHF, and it is believed that the association between insulin resistance and left ventricular hypertrophy may contribute to the increase risk of symptomatic CAD in insulin-resistant subjects.

Several reports have also focussed on metabolic abnormalities including abnormal intracellular $Ca^{2+}$ handling, defects in myocardial glucose use, and activation of PKC as possible explanations for the pathogenesis of diabetic cardiomyopathy. Additionally, there may also be a role for AGEs, discussed above, in the pathogenesis of diabetic cardiomyopathy. Diabetic patients have increased arterial stiffness compared with nondiabetic individuals and manifest diminished left ventricular compliance at a young age. Several investigators have reported that diabetes has several features of accelerated aging at the tissue level and at the level of collagen itself. Aging and diabetes mellitus are associated with cross-linking and nonenzymatic glycosylation of collagen. This led to the concept that glycosylation could help to explain the progressive cross-linking of collagen during normal aging and at an accelerated rate in diabetes, leading to changes in vascular tissue mechanical properties. Thus, disturbances of vascular and cardiac mechanical properties in diabetes may be caused by a common mechanism. Among the structural alterations associated with AGEs formation is collagen-to-collagen cross-linking, which alters the structure and function of this protein, leading to tissue rigidity. Increased arterial stiffness in patients with diabetes is said to be strongly correlated with increased aorta and myocardial collagen advanced glycation. Airaksinen K E, et al., "Diminished arterial elasticity in diabetes: association with fluorescent advanced glycosylation end products in collagen," *Cardiovasc Res* 27:942-945 (1993). Further evidence supporting the AGE hypothesis is the observation that agents that specifically inhibit AGE formation reportedly are useful to prevent the pathologic stiffening process of diabetes and aging. Norton G R, et al., "Aminoguanidine prevents the decreased myocardial compliance produced by streptozotocin-induced diabetes mellitus in rats," *Circulation* 93:1905-1912 (1996); Huijberts M S, et al., "Aminoguanidine treatment increases elasticity and decreases fluid filtration of large arteries from diabetic rats," *J Clin Invest* 92:1407-1411 (1993). For example, treatment of diabetic rats with aminoguanidine, an inhibitor of AGE formation, reportedly increased carotid artery compliance, decreases aortic impedance, and prevented the decreased myocardial compliance. Id.

It has been attempted with greater or lesser efficacy to pharmacologically influence the process of nonenzymatic glycation and AGE products formation using, in general, two approaches. The first is inhibition of the rearrangement from early to advanced glycation endproducts by means of hydrasine:aminoguanidine hydrochloride or analogue. The second is the breaking of already existing AGE products with substituted thiazolium salts. Pharmacologic activity of aminoguanidine may render impossible or retard some of microvascular complications in animal model. Although the mechanism of aminoguanidine action has not been completely understood, it may inhibit some stages in a series of chemical reactions leading to glycation end-product formation. In spite of the first encouraging results, clinical trials of aminoguanidine in patients with type 2 diabetes mellitus have been suspended due to adverse effects. See, for example, Brownlee M., "Negative consequences of glycation," *Metabolism* 49 (suppl 1): 9-13 (2000); Singh R, Barden A, Mori T, Beilin L., "Advanced glycation end-products: a review," *Diabetologia* 44:129-146 (2001); Vlassara H, Bucala R, Striker L., "Pathogenic effects of AGEs: Biochemical, biologic, and clinical implications for diabetes and aging," *Lab Invest* 70:138-151 (1994); Lyons T, Jenkins A J., "Glycation, oxidation and lipoxidation in the development of the complications of diabetes mellitus: a 'carbonyl stress' hypothesis," *Diabetes Rev* 5:365-391 (1997).

As indicated herein, it is understood that diabetes mellitus is a major source of morbidity in developed countries. Among its co-morbid conditions, atherosclerosis is one of the most important. Since the availability of insulin, up to three-quarters of all deaths among diabetics can be directly attributed to CAD. In patients with type 1 diabetes, up to one third will die of CAD by the age of 50 years. A number of known risk factors for CAD, such as hypertension, central obesity and dyslipidemia, are more common in diabetics than in the general population. Thus diabetes represents a major contributing factor to the CAD burden in the developed world, and most of the excess attributed risk of CAD in diabetics cannot be readily quantified with the use of traditional risk factors analysis. As indicated, the relation between hyperglycemia and CAD is the subject of debate because serum glucose does not consistently predict the existence of CAD. However, recent prospective data have clearly established a link between a marker for chronic average glucose levels (HbA1c) and cardiovascular morbidity and mortality. There are established sequelae of hyperglycemia, such as cytotoxicity, increased extracellular matrix production and vascular dysfunction and all have been implicated in the pathogenesis of diabetes-induced vascular disease, and the formation of AGEs correlate directly with the vascular and renal complications of diabetes mellitus. As noted, patients with diabetes mellitus are particularly susceptible to morbidity and mortality resulting from cardiovascular diseases, especially atherosclerosis, the progression of which is characterized by infiltration of lipids into the vessel wall and the formation of fibrous tissue called the atheromatous plaque. Clinical symptoms of atherosclerosis do not usually occur until over half of the lumen becomes obstructed (occluded) by the plaque, typically in the fifth and sixth decades of life. Consequently, studies on the role of plasma lipids in health and in the genesis of CHD have dominated research on CHD over the past several decades. Current positive evidence documents the premise that the following are important risk factors: family history, a high plasma concentration of low-density lipoprotein (LDL) and a low concentration high density lipoprotein (HDL) cholesterol (separately as well as jointly), high plasma concentration of apoB (the major protein fraction of the LDL particle), high plasma lipoprotein (a) (Lp(a)) concentration, high plasma fibrinogen concentration, hypertension, diabetes, obesity, increased plasma concentration of homocysteine (all these themselves have genetic determinants), high dietary fat intake, lack of exercise, stress, and smoking.

The pathogenesis of the atherosclerosis in diabetes mellitus is not entirely clear and conventional risk factors such as smoking, obesity, blood pressure and serum lipids fail to explain fully this excess risk. As noted, important features in the pathogenesis of atherosclerosis appear to include vascular endothelial injury, platelet adhesion and activation, fibrin deposition, cellular proliferation, and low-density lipoprotein cholesterol accumulation. Fibrin deposition is an invariable feature in atherosclerotic lesions. Therefore, disturbances of haemostasis leading to accelerated fibrin formation (hypercoagulability) and delayed fibrin removal (impaired fibrinolysis) may contribute to the development of atherosclerosis. Hyperactive platelets, hypercoagulability and impaired fibrinolysis, as indicated above, also promote thrombosis formation at the site of ruptured atherosclerotic lesion and lead to final occlusion event in the progression of atherosclerosis. Although platelet counts are generally normal in patients with diabetes mellitus, multiple studies offer evidence of enhanced activation or increased platelet activity, and an increase in plasma levels of vWF, which is important for the adhesion of platelets to subendothelial structures, has been reported in diabetic patients.

In diabetes mellitus disturbances of haemostasis leading to hypercoagulability have been observed in numerous studies. Besides altered screening tests, alterations of several coagulation factors and inhibitors have been occasionally described. A problem encountered when studying the association between hypercoagulability and atherosclerosis is the number of laboratory tests proposed to detect hypercoagulability and the wide variability of such tests in a given subject. Results of cohort studies have shown that among different coagulation factors analyzed, increased concentration of fibrinogen, factor VII and vWF have predictive value for coronary atherosclerosis and can be considered as risk factors for cardiovascular events. Increase in these factors could participate in the pathogenesis of atherosclerosis, predominantly of coronary arteries. A relationship has been established between plasma concentration of fibrinogen, the quantity of fibrinogen and fibrin present in the vessel wall and the severity of atherosclerosis. These associations are more pronounced in diabetic patients.

Factor VII is a vitamin K dependent protein synthesized in the liver. It is the key enzyme in the initiation of blood coagulation. The Northwick Park Heart Study and the PROCAM study have shown that there is a positive correlation between increased factor VII and cardiovascular mortality. Plasma concentration of factor VII is closely related to several environmental factors, mainly triglycerides and cholesterol levels. These associations are highly dependent on dietary intake. An increase in factor VII has been described in diabetes mellitus and is more pronounced in those with microalbuminuria. Only limited data are available concerning the contributory role of insulin resistance to elevated factor VII. The relationship between factor VII and insulin and proinsulin have been described as very weak or present only in women. Factor VII which is influenced by the efficiency of the metabolism of triglyceride-rich lipoproteins could in this way be modified in insulin resistance.

Hypercoagulability can also be judged from increased levels of markers of coagulation system activation, which reflect enhanced thrombin generation. Prothrombin fragment 1+2 released when thrombin is formed from prothrombin is increased in diabetes. Once activated, thrombin is rapidly inactivated by antithrombin, forming thrombin-antithrombin complexes, which subsequently circulate and are removed by the liver. Multiple studies have documented elevated thrombin-antithrombin complexes in diabetes. Fibrinopeptide A is released when fibrinogen is converted to fibrin by thrombin. Thus, fibrinopeptide A levels are increased during coagulation. Measurement of fibrinopeptide A in diabetes has yielded a variety of results, from elevated to normal.

hyperinsulinemia has also been associated with cardiovascular disease in non-diabetic subjects. In those with type 2 diabetes the extent of hyperinsulinemia parallels plasma PAI-1 activity, and insulin has been implicated as a major physiological regulator of PAI-1. Despite population correlations of insulin and PAI-1, and the effect of insulin on PAI-1 production in vitro, a direct effect of insulin on PAI-1 levels in vivo in humans has not been shown, either with intravenous infusion of insulin or by an oral glucose load with the aim of producing portal hyperinsulinemia. Thus, in humans there is little evidence that interventions resulting in increased concentration of insulin in vivo increase PAM. On the other hand reducing insulin levels and insulin resistance by exercise, weight loss and the drug metformin has been shown to reduce PAI-1. In patients with type 2 diabetes approximately 30% of fasting immunoreactive insulin concentration consists of proinsulin-like molecules. The elevated levels of PAI-1 in these subjects may, therefore, be a consequence of precursor insulin rather than insulin itself.

Hyperglycemia is an additional risk factor for impaired fibrinolysis. Glucose can directly increase PAI-1 production in human endothelial cells. In patients with type 2 diabetes a significant correlation between glucose concentration and PAI-1 and has been observed. It has been proposed that insulin resistance or hyperinsulinemia could influence the synthesis of PAI-1 via effects on lipid metabolism. In patients with diabetes, dyslipidaemia, in particular high triglyceride and low high-density lipoprotein level, is common. Studies in vitro have reportedly demonstrated the effect of various lipoproteins on PAI-1 synthesis. VLDLs from hypertriglyceridemic patients increase endothelial cell production of PAI-1 to a greater degree than that from normo-triglyceridaemic subjects. Oxidized LSLs also stimulate endothelial cell PAI-1 synthesis as does lipoprotein(a). Lipoprotein(a), LDSs, and HDLs also suppress t-PA secretion from human endothelial cells in dose dependent manner.

In sum, there is significant laboratory evidence of chronic platelet activation, enhanced coagulation and impaired fibrinolysis in patients with diabetes mellitus. These disturbances of haemostasis favor development of atherosclerosis and thrombosis in particularly of coronary arteries.

Metals are present naturally in body and many are essential for cells (e.g., Cu, Fe, Mn, Ni, Zn). However, all metals are toxic at higher concentrations. One reason metals may become toxic is because they may cause oxidative stress, particularly redox active transition metals, which can take up or give off an electron (e.g., $Fe^{2+/3+}$, $Cu^{+/2+}$) can give rise to free radicals that cause damage (Jones et al., "Evidence for the generation of hydroxyl radicals from a chromium(V) intermediate isolated from the reaction of chromate with glutathione," *Biochim. Biophys. Acta* 286: 652-655 (1991); Li, Y. and Trush, M. A. 1993. DNA damage resulting from the oxidation of hydroquinone by copper: role for a Cu(II)/Cu(I) redox cycle and reactive oxygen generation," *Carcinogenes* 7: 1303-1311 (1993). Another reason why metals may be toxic is because they can replace other essential metals in or enzymes, disrupting the function of these molecules. Some metal ions (e.g., Hg+ and Cu+) are very reactive to thiol groups and can interfere with protein structure and function.

As noted herein, humans subject to type 2 diabetes or abnormalities of glucose mechanism are particularly at risk to the precursors of heart failure, heart failure itself and a miscellany of other diseases of the arterial tree. It has been reported that in Western countries, more than 50% of patients with type 2 diabetes die from the effects of cardiovascular disease. See, Stamler et al., *Diabetes Care* 16:434-44 (1993). It has also been reported that even lesser degrees of glucose intolerance defined by a glucose tolerance test (impaired glucose tolerance, or "IGT") still carry an increased risk of sudden death. See, Balkau et al., *Lancet* 354:1968-9 (1999). For a long time, it was assumed that this reflected an increased incidence of coronary atherosclerosis and myocardial infarction in diabetic subjects. However, evidence is mounting that diabetes can cause a specific heart failure or cardiomyopathy in the absence of atherosclerotic coronary artery disease.

Cardiac function is commonly assessed by measuring the ejection fraction. A normal left ventricle ejects at least 50% of its end-diastolic volume each beat. A patient with systolic heart failure commonly has a left ventricular ejection fraction less than 30% with a compensatory increase in end-diastolic volume. Hemodynamic studies conducted on diabetic subjects without overt congestive heart failure have observed normal left ventricular systolic function (LV ejection fraction) but abnormal diastolic function suggesting impaired left ventricular relaxation or filling. See, Regan et al., *J. Clin. Invest.* 60:885-99 (1977). In a recent study, 60% of men with type 2 diabetes without clinically detectable heart disease were reported to have abnormalities of diastolic filling as assessed by echocardiography. See, Poirier et al., *Diabetes Care* 24:5-10 (2001). Diagnosis may be made, for example, by noninvasive measurements. In the absence of mitral stenosis, mitral diastolic blood flow measured by Doppler echocardiography is a direct measure of left ventricular filling. The most commonly used measurement is the A/E ratio. Normal early diastolic filling is rapid and is characterized by an E-wave velocity of around 1 m/sec. Late diastolic filling due to atrial contraction is only a minor component, and the A-wave velocity is perhaps around 0.5 m/sec. This gives a normal A/E ratio of approximately 0.5. With diastolic dysfunction, early diastolic filling is impaired, atrial contraction increases to compensate, and the A/E ratio increases to more than 2.0.

Treatment of diabetic cardiomyopathy is difficult and the options are limited. Tight control of blood glucose levels might prevent or reverse myocardial failure, although this may be true only in the early stages of ventricular failure. Angiotensin converting enzyme inhibitors such as captopril improve survival in heart failure particularly in patients with severe systolic heart failure and the lowest ejection fractions. There are, however, various therapies for diabetic cardiomyopathy that are not recommended. For example, inotropic drugs are designed to improve the contraction of the failing heart. However, a heart with pure diastolic dysfunction is already contracting normally and it is believed that inotropic drugs will increase the risk of arrhythmias. Additionally, there appears to be no logical reason to use vasodilator drugs that reduce after-load and improve the emptying of the ventricle because ejection fraction and end-diastolic volume are already normal. After-load reduction may even worsen cardiac function by creating a degree of outflow obstruction.

Diuretics are the mainstay of therapy for heart failure by controlling salt and water retention and reducing filling pressures. However, they are contraindicated in diastolic dysfunction where compromised cardiac pump function is dependent on high filling pressures to maintain cardiac output. Venodilator drugs such as the nitrates, which are very effective in the management of systolic heart failure by reducing pre-load and filling pressures, are understood to be poorly tolerated by patients with diastolic heart failure. Ejection fraction and end-systolic volume are often normal and any reduction in pre-load leads to a marked fall in cardiac output. Finally, there is concern about the use of β-blockers in heart failure because of their potential to worsen pump function. There is also concern regarding the administration of β-blockers to patients with diabetes who are treated with sulphonylurea drugs and insulin due to a heightened risk of severe hypoglycaemia.

Thus, it will be understood that the mechanisms underlying various disorders of the heart, the macrovasculature, the microvasculature, and the long-term complications of diabetes, including associated heart diseases and conditions and long-term complications, are complex and have long been studied without the discovery of clear, safe and effective therapeutic interventions. There is a need for such therapies, which are described herein.

SUMMARY OF THE INVENTION

The heart is the most susceptible of all the body organs to premature ageing and free radical oxidative stress.

A high frequency of heart failure cardiomyopathy and macrovascular disease in severely diabetic animals, for example, has been confirmed. It has also been discovered as described and claimed herein that treatment with specific copper chelators and other agents (e.g., zinc which prevents copper absorption) that decrease copper values and, preferably, do not lead to depletion states of other transition metals (e.g., iron, zinc and manganese), or essential metals, will benefit a significant number and spectrum of the population, including for those diseases, disorders, and/or conditions described above, whether or not attributable to diabetes or to any particular form of diabetes.

Preferably, treatment is preceded by a determination of the absence of a copper deficiency state or undesirably low copper values. Without wishing to be bound be bound by any particular theory or mechanism, it is believed that that copper values, particularly, for example, copper (II), that not bound internally within cells is available to mediate together with available reducing substances the generation of damaging free radicals that have a role in both tissue damage and impairment of stem cell mediated repair of such tissue.

By way of example, in relation to the normal myocardium tissue, it is believed that damage as a result of the presence of free radicals leads to heart failure and/or cardiomyopathy in both diabetics and nondiabetics. The continued pressure of such free radicals is also believed to impair stem cell mediated repair of the myocardium back to its normal healthy state. In respect of such damage and repair impairment the present invention provides for a desired reduction in available free copper values as an appropriate preventive and/or treatment approach.

By reference to available copper values in mammals (including human beings), those mammalian patients with a copper level that is "elevated" beyond that of the general population of such mammals can be identified. Reference herein to "elevated" in relation to the presence of copper values will include humans having at least about 10 mcg free copper/dL of serum when measured as discussed herein. A measurement of free copper equal to total plasma copper minus ceruloplasmin-bound copper can be made using various procedures. A preferred procedure is disclosed in the Merck & Co datasheet (www.Merck.com) for SYPRINE® (trientine hydrochloride) capsules, a compound used for treatment of Wilson's Disease, in which a 24 hour urinary copper analysis in is undertaken to determine free cooper in the serum by calculating the difference between quantitatively determined total copper and ceruloplasmin-copper. Alternative names for trientine include N,N'-Bis(2-aminoethyl)-1,2-ethanedi-amine; triethylenetetramine; 1,8-diamino-3,6-diazaoetane; 3,6-diazaoctane-1,8-diamine; 1,4,7,10-tetraazadecane; trien; TETA; TECZA and triene.

Without wishing to be bound by any particular theory or mechanism, it is believed that reduction in available free copper helps to prevent macrovascular, microvascular and/or toxic/metabolic diseases of the kind hereinafter exemplified and in tissue repair processes. This is irrespective of the glucose metabolism of the patient and is thus applicable to diabetics and nondiabetics alike, as well as to those with and without impaired or abnormal glucose levels or metabolism.

Is also believed, again without wishing to be bound by any particular theory or mechanism, that cardiovascular accumulation of redox-active transition metal ions is responsible for many of the adverse outcomes and long term complications in diabetes. Under physiological conditions, injury to a target organ is sensed by distant stem cells, which migrate to the site of damage then undergo alternate stem cell differentiation. These events promote structural and functional repair. However, the accumulation of redox-active transition metals, particularly copper in cardiac or vascular tissues in subjects with diabetes is accompanied by a suppression of the normal tissue regeneration effected by the migration of stem cells. Elevated tissue levels of copper suppress these normal biological behaviors of such undifferentiated cells. Conditions occurring in the context of diabetes or impaired glucose tolerance, for example, in which the suppression of normal stem cell responses can cause impairment of normal tissue responses, include cardiac failure, acute myocardial infarction, wound healing and ulceration, tissue damage caused by infection, diabetic kidney damage, impaired cardiac regeneration, impaired vascular regeneration, and impaired regeneration of dependant organs.

Conditions in which therapy to lower copper values in diabetic patients (e.g., with IGT or type 2 diabetes mellitus) will prove beneficial include, for example, heart failure in the context of diabetes, myocardial infarction in the context of diabetes, wound healing and ulceration in the context of diabetes, soft tissue damage resulting from infection and occurring in the context of diabetes or impaired glucose tolerance, kidney damage occurring in the context of diabetes, impaired cardiac regeneration, impaired vascular regeneration, and impaired regeneration of dependant organs.

With regard to heart failure in the context of diabetes, significant regeneration of cardiac tissues can occur within a few days of cardiac transplantation. A likely mechanism is migration of stem cells from extra-cardiac sites to the heart, with subsequent differentiation of such cells into various specialized cardiac cells, including myocardial, endothelial and coronary vascular cells. Without wishing to be bound by any particular theory or mechanism, it is believed that copper accumulation in cardiac tissues is likely to severely impair these regenerative responses, and that there is a role for therapy, including acute intravenous therapy, with transition a copper chelator in the treatment of diabetic heart failure.

Regarding myocardial infarction (MI) in the context of diabetes, for example, it is understood that MI is accompanied by proliferation of cells in the ventricular myocardium. When MI occurs in the context of diabetes, the presence of elevated tissue levels of redox-active transition metals suppresses normal stem cell responses, resulting in impaired structural and functional repair of damaged tissues. It has been reported that up to 20% of cells in the heart may be replaced by stem cell migration from extra-ventricular sites, as soon as four days after cardiac transplantation. It is believed that treatment of AMI in the context of diabetes will be improved by, for example, acute (if necessary, parenteral) as well as by subsequent chronic administration of chelators. Without wishing to be bound by any particular theory or mechanism, it is also believed that impairment of cardiac function in diabetes is characterized at least in part by a toxic effect of accumulated transition metals on tissue dynamics, resulting in impaired tissue regeneration caused in turn by suppression of normal stem cell responses, which mediate physiological tissue regeneration by migration to damaged tissue from external sites.

With regard to wound healing and ulceration in the context of diabetes, the processes of normal tissue repair require intervention of mobilizing stem cells, which effect repair of the various layers of blood vessels, for example. Without wishing to be bound by any particular theory or mechanism, it is believed that an accumulation of transition metals (particularly copper) in vascular tissues causes the impaired tissue behaviour characteristic of diabetes, for example, including impaired wound repair following surgery or trauma, and the exaggerated tendency to ulceration and poor healing of established ulcers. Without wishing to be bound by any particular theory or mechanism, it is believed that the treatment of diabetics with copper chelators before they undergo surgery, for example, or in the context of traumatic tissue damage, will be of benefit. It is further believed that it is probable that surgery in diabetics, for example, would have a better outcome if excess transition metals in, for example, blood vessels, were removed or reduced prior to surgery. This may be accomplished, for example, on either an acute basis (with parenteral therapy for example) or on a more chronic basis (with oral therapy for example) prior to actual surgery.

Regarding soft tissue damage resulting from infection and occurring in the context of diabetes or impaired glucose tolerance, for example, and without wishing to be bound by any particular theory or mechanism, it is believed that the processes of normal tissue repair following infection require intervention of mobilized stem cells that migrate to sites of tissue damage to effect tissue regeneration and repair, for example, of the various layers of blood vessels, and that repair of such tissue damage will be impaired by suppressed stem cell responses, such as those caused by the build up of redox-active transition metals (particularly copper) in tissues, for examples the walls of blood vessels. Treatment with a copper chelator or other agent to remove copper will improve these conditions.

Regarding kidney damage occurring in the context of diabetes, again without wishing to be bound by any particular theory or mechanism, it is believed that impaired stem cell responses in the kidneys of diabetics contribute to diabetic nephropathy and renal failure. Treatment of diabetics having kidney failure by administration of a copper chelator will improve organ regeneration by restoring normal tissue healing by allowing stem cells to migrate and differentiate normally. Furthermore, a reduction in extra-cellular copper values is also proposed to be advantageous in the nondiabetic mammal and even in a mammal without a glucose mechanism abnormality, in that such lower levels will lead to one or both a reduction in copper-mediated tissue damage and improved tissue repair by restoration of normal tissue stem cell responses.

Regarding impaired cardiac regeneration, again without wishing to be bound by any particular theory or mechanism, it is believed that copper accumulation in cardiac tissues suppresses the normal tissue regeneration effected by the migration of stem cells from extra-cardiac sites to the heart, with subsequent differentiation of such cells into various specialised cardiac cells, including myocardial, endothelial, and coronary vascular cells. A reduction in extra-cellular copper values will reduce or ablate the impairment of tissue regeneration caused by the suppression of normal stem cell responses.

With regard to impaired vascular regeneration, the processes of vascular regeneration is believed to require the intervention of mobilising stem cells, which effect repair of the various layers of blood vessels. Without wishing to be bound by any particular theory or mechanism, it is believed that an accumulation of transition metals (particularly copper) in vascular tissues causes impaired tissue regeneration by suppressing the migration of undifferentiated stem cells and normal tissue stem cell responses. A reduction in extracellular copper values is advantageous in that such lower levels will lead to a reduction in the impairment of vascular regeneration by restoration of normal tissue stem cell responses.

As to impaired regeneration of dependant organs, it is believed, without wishing to be bound by any particular theory or mechanism, that an accumulation of transition metals (particular copper) in the tissues of the dependant organs of the cardiovascular tree (e.g., retina, kidney, nerves, etc.) causes impaired tissue regeneration by suppressing the migration of stem cells and thereby the normal biological behaviours of such stem cells. A reduction in extra cellular copper values is advantageous to reduce or ablate the impairment in tissue regeneration by restoration of normal tissue stem cell responses.

It is an object of the present invention to provide methods of treatment and related methods, uses and pharmaceutical compositions that ameliorate, prevent or treat any one or more disease states of the cardiovascular tree (including the heart) and dependent organs (e.g.; retina, kidney, nerves, etc.) exacerbated by elevated non-intracellular free copper values levels. Diseases of the cardiovascular tree and diseases of dependent organs include, for example, but are not limited to any one or more of:

disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy;

atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries;

toxic, drug-induced, and metabolic (including hypertensive and/or diabetic disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

The present invention also relates to any such ailments and their treatment irrespective (unless otherwise stated) of any diabetic and/or glucose abnormality state of the mammalian patient.

Accordingly included within the categories of disease of patients that are usefully be targeted by the procedures of the present invention are, for example, any one or more of the following non-exhaustive list: diabetic cardiomyopathy, diabetic acute coronary syndrome (e.g.; myocardial infarction—MI), diabetic hypertensive cardiomyopathy, acute coronary syndrome associated with impaired glucose tolerance (IGT), acute coronary syndrome associated with impaired fasting glucose (IFG), hypertensive cardiomyopathy associated with IGT, hypertensive cardiomyopathy associated with IFG, ischaemic cardiomyopathy associated with IGT, ischaemic cardiomyopathy associated with IFG, ischaemic cardiomyopathy associated with coronary heart disease (CHD), acute coronary syndrome not associated with any abnormality of the glucose metabolism, hypertensive cardiomyopathy not associated with any abnormality of the glucose metabolism, ischaemic cardiomyopathy not associated with any abnormality of the glucose metabolism (irrespective of whether or not such ischaemic cardiomyopathy is associated with coronary heart disease or not), and any one or more disease of the vascular tree including, by way of example, disease states of the aorta, carotid, cerebrovascular, coronary, renal, retinal, vasa nervorum, iliac, femoral, popliteal, arteriolar tree and capillary bed.

Without wishing to be bound by any particular theory or mechanism, it is believed that in the aforementioned diabetic states or glucose metabolism abnormal states that diabetic complications in the distal regions of the arterial tree can be mediated by the regimen of the present invention whilst at the same time improving more proximal conditions.

With a nondiabetic patient the complications arising from an elevated copper values content of the whole body may be more proximal than distal. Nonetheless mediation of and/or repair of such damage is possible (including of or to the aorta, carotid, cerebrovascular, coronary, renal, retinal, vasa nervorum, iliac, femoral, popliteal, arteriolar tree and capillary bed) and it is believed will be improved by the regimen of the present invention.

As used herein the term "diabetic" refers to a human being or other mammal suffering from type 2 diabetes or impaired glucose tolerance (IGT), or any other form of diabetes or impaired glucose metabolism in which removal of excess or undesired copper would be of value for treatment.

The term "cardiomyopathy" as used herein and where the context so allows includes both cardiomyopathy and associated heart failure.

As used herein the terms "subjecting the patient" or "administering to" includes any active or passive mode of ensuring the in vivo presence of the active compound(s) or metabolite(s) irrespective of whether one or more dosage to the mammal, patient or person is involved. Preferably the mode of administration is oral. However, all other modes of administration (particularly parenteral, e.g., intravenous, intra muscular, etc.) are also contemplated.

As used herein, "therapeutically effective amount" refers to a predetermined amount of an agent that will or is calculated to achieve a desired response, for example, a therapeutic or preventative or ameliorating response, for example, a biological or medical response of a tissue, system, animal or human that is sought, for example, by a researcher, veterinarian, medical doctor, or other clinician.

By "pharmaceutically acceptable" it is meant, for example, a carrier, diluent or excipient that is compatible with the other ingredients of the formulation and generally safe for administration to a recipient thereof or that does not cause an undesired adverse physical reaction upon administration.

As used herein, "mammal" has its usual meaning and includes primates (e.g.; humans and nonhumans primates), experimental animals (e.g.; rodents such as mice and rats), farm animals (such as cows, hogs, sheep and horses), and domestic animals (such as dogs and cats).

The term "elevated" has the meaning previously set forth whilst the term "normal" in respect of the copper values status of, for example, a human patient means, adopting the test referred to previously as having been disclosed by Merck & Co Inc. is a patient having less than 10 mcg free copper/dL of serum.

As used herein "copper deficient" means the diagnosis of copper deficiency is usually made on the basis of low serum levels of copper (<65 μg/dL) and low ceruloplasmin levels (<18 mg/dL). Serum levels of copper may be elevated in pregnancy or stress conditions since ceruloplasmin is an acute-phase reactant.

As used herein, the terms "treatment" or "treating" of a condition, disorder, and/or a disease in a mammal, means, where the context allows, (i) preventing the condition or disease, that is, avoiding one or more clinical symptoms of the disease; (ii) inhibiting the condition or disease, that is, arresting the development or progression of one or more clinical symptoms; and/or (iii) relieving the condition or disease, that is, causing the regression of one or more clinical symptoms.

As used herein "associated with" simply means both circumstances exist and should not be interpreted as meaning one necessarily is causally linked to the other.

The term "chelatable copper" includes copper in any of its chelatable forms including different oxygen states such as copper (II). Accordingly the term "copper values" (for example, elemental, salts, etc.) means copper in any appropriate form in the body available for such chelation (for example, in extracellular tissue and possibly bound to cell exteriors and/or collagen as opposed to intracellular tissue) and/or capable of being reduced by other means (for example, zinc administration).

Some preferred chelators of copper values appropriate for mammalian administration for treatment of one or more of the conditions, disorders and/or diseases herein include, for example (where appropriate as a salt such as, for example, a suitable calcium sodium salt to avoid hypocalcemia): trientine (triene), ethylenediaminetetraacetic acid (EDTA), diethylenetriaminetetraacetic acid (DPTA), 2,2,2 tetramine tetrahydrochloride (TETA), 2,3,2 tetramine tetrahydrochloride, D-penicillamine (DPA), 1,4,8,11 tetraazacyclotetradecane (Cyclam), 5,7,7',12,14,14' hexamethyl-1,4,8,11 tetraazacyclotetradecane (Cyclam S), Sodium 2,3 dimercaptopropane-1-sulfonate (DMPS), N-acetylpenicillamine (NAPA), D-Penicillamine (PA),' Desferroxamine, 2,3-dimercaptopropanol (BAL), 2,3-dimercaptosuccinic acid (DMSA), trithiomolybdate, 3-7-Diazanonan-1,9-diamin (BE 6184), 1,4,8,11-tetraazacyclotetradecane-1,4,8,11-tetraacetic acid, 1,4,8,11-tetraazabicyclo[6.6.2]hexadecane, 4,11-bis(N,N-diethylamidomethyl)-1,4,8,11-tetraazabicyclo[6.6.2]hexadecane, 4,11-bis(amidoethyl)-1,4,8,11-tetraazabicyclo[6.6.2]hexadecane, melatonin, clioquinol, cuprizone, N,N'-diethyldithiocarbamate, zinc acetate, zinc salts, bathocuproinedisulfonic acid, bathocuprinedisulfonate, neocuproine (2,9-dimethyl-1,10-phenanthroline), tetrathiomolybdate, trimetazidine, triethylene tetramine tetrahydrochloride, 2,3,2-tetraamine, pyridine-2,6-bis(thiocarboxylic acid) or pyrrolidine dithiocarbamate, tetraethylenepentamine, N,N,N',N-tetrakis(2-pyridylemethyl)ethylenediamine, 1,4,7,11-tetraazaundecane tetrahydrochloride, tetraethylenepentamine pentahydrochloride, D-Penicillamine (DPA), 1,10-orthophenanthroline, 3,4-Dihydroxybenzoic acid, 2,2'-bicinchonoic acid, diamsar, 3,4',5, trihydroxystilbene (resveratrol), mercaptodextran, o-phenanthroline, disulfiram (antabuse), sar, calcium trisodium diethylenetriaminepentaacetate (salt of cpd above), and methimazole (1-methyl-2-thiolimidazole).

In another aspect, one or more agents capable of decreasing the copper values content of the patient, if a chelator, has a preferential affinity for copper values over the values of other trace metals (such as iron, zinc and/or manganese).

In yet another aspect, the preferential affinity for copper values is such that copper excess of from 100% to 500% over that of a normal healthy mammal of the species can be controlled to such normal levels or approaching such normal levels without leading to depletion or excessive decreases in such other transition metals as iron, zinc and/or manganese. It is particularly desirable not to induce diseases of such transition metal deficiencies, for example, anemia.

Administration of any copper chelator (for example, trientine) can be by a variety of routes including parenteral and oral. With such agents a dose rate for oral administration may be about 10 times that for parenteral administration. This will overcome any lowered bioavailablity. With trientine a suitable parenteral dose is about 120 mg/day in man.

Accordingly where the chelator is trientine hydrochloride (and irrespective of excipients, diluents, carriers and vehicles), for example, the dosage or dosages in a human patient, if parenteral, is to provide about 120 mg/day, and if oral, about 1200 mg/day.

Alternatively (and/or additionally) the agent capable of reducing copper values is a zinc salt (preferably as a flavoured aqueous solution) or trithiomolybdate (also a chelator). Suitable zinc salts include, for example: zinc acetate; zinc chloride; zinc sulphate; zinc salts of intermediates of the citric acid cycle, such as citrate, isocitrate, ketoglutarate, succinate, malate; and, zinc glucoante.

With the preferred chelators herein referred to, or others, and suitable salts of zinc including those referenced herein, or others, it is possible to selectively decrease the copper values in the body as a whole (without reaching depletion states for other transition metals) even though it is believed that there is little decrease in copper values in the intra cellular tissue. It is believed that the decrease is primarily extra cellular (for example, interstites, on the exterior of cells and/or on collagen).

In one aspect the present invention is a method of improving tissue repair in a mammalian patient of damaged tissue selected from that of the myocardium, the vascular tree and organs dependent on the vascular tree, said method comprising or including the step of subjected the patient to, and/or administering to the patient, an agent or agents effective in lowering the copper values content of the patient's body sufficient to improve tissue repair.

In another aspect, the patient is not suffering from Wilson's Disease yet has an elevated copper values content. In yet another aspect, there is at least one copper values status determination.

In still another aspect, the agent is trientine or a trientine type copper chelation agent.

Trientine hydrochloride may be administered at dosages or a dosage to provide, if parenteral, at least about 120 mg/day in a human patient, and if oral, at least about 1200 mg/day in a human patient.

In one aspect, the patient is a human being suffering from type 2 diabetes mellitus.

It is believed the improvement of the tissue repair arises from a restoration of, or substantial restoration of, normal tissue stem cell responses, although there is no intent to be bound by this mechanism.

The agent(s) may be selected from, for example, trientine (triene), ethylenediaminetetraacetic acid (EDTA), diethylenetriaminetetraacetic acid (DPTA), 2,2,2 tetramine tetrahydrochloride (TETA), 2,3,2 tetramine tetrahydrochloride, D-penicillamine (DPA), 1,4,8,11 tetraazacyclotretradecane (Cyclam), 5,7,7',12,14,14' hexamethyl-1,4,8,11 tetraazacyclotretradecane (Cyclam S), Sodium 2,3 dimercaptopropane-1-sulfonate (DMPS), N-acetylpenicillamine (NAPA), D-Penicillamine (PA),' Desferroxamine, 2,3-dimercaptopropanol (BAL), 2,3-dimercaptosuccinic acid (DMSA), trithiomolybdate, 3-7-Diazanonan-1,9-diamin (BE 6184), 1,4,8,11-tetraazacyclotetradecane-1,4,8,11-tetraacetic acid, 1,4,8,11-tetraazabicyclo[6.6.2]hexadecane, 4,11-bis(N,N-diethyl-amidomethyl)-1,4,8,11-tetraazabicyclo[6.6.2]hexadecane, 4,11-bis(amidoethyl)-1,4,8,11-tetraazabicyclo[6.6.2]hexadecane, melatonin, clioquinol, cuprizone, N,N'-diethyldithiocarbamate, zinc acetate, zinc salts, bathocuproinedisulfonic acid, bathocuprinedisulfonate, neocuproine (2,9-dimethyl-1,10-phenanthroline), tetrathiomolybdate, trimetazidine, triethylene tetramine tetrahydrochloride, 2,3, 2-tetraamine, pyridine-2,6-bis(thiocarboxylic acid) or pyrrolidine dithiocarbamate, tetraethylenepentamine, N,N,N',N-tetrakis(2-pyridylemethyl)ethylenediamine, 1,4,7,11-tetraazaundecane tetrahydrochloride, tetraethylenepentamine pentahydrochloride, D-Penicillamine (DPA), 1,10-orthophenanthroline, 3,4-Dihydroxybenzoic acid, 2,2'-bicinchinonic acid, diamsar, 3,4',5, trihydroxystilbene (resveratrol), mercaptodextran, o-phenanthroline, disulfiram (antabuse), sar, calcium trisodium diethylenetriaminepentaacetate (salt of cpd above), and/or methimazole (1-methyl-2-thiolimidazole).

The agent (agents) may also be a zinc salt (zinc salts).

Damage to be ameliorated, treated, and/or prevented, may be, for example, damage that has arisen from any one or more of: (i) disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; (ii) atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; (iii) toxic, drug-induced, and metabolic (including hypertensive and/or diabetic disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; (iv) plaque rupture of atheromatous lesions of major blood vessels such as the aorta, the coronary arteries, the carotid arteries, the cerebrovascular arteries, the renal arteries, the iliac arteries, the fermoral arteries and the popliteal arteries.

The patient may be suffering from and/or be predisposed to heart failure.

The patient may be suffering from diabetes or impaired glucose metabolism, for example, type 2 diabetes mellitus.

In another aspect the invention is the use of a compound (a) which itself in vivo or (b) which has at least one metabolite in vivo which is (i) a copper chelator or (ii) otherwise reduces available copper values for the production of a pharmaceutical composition or dosage unit able to reduce the level of copper in a mammal thereby to elicit by a lowering of copper values in a mammalian patient an improvement of tissue repair of damaged tissue selected from that of the myocardium, the vascular tree and organs dependent on the vascular tree.

The damage may be that which has arisen from a disease selected, for example from the group: (i) disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; (ii) atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; (iii) toxic, drug-induced, and metabolic (including hypertensive and/or diabetic disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; (iv) plaque rupture of atheromatous lesions of major blood vessels such as the aorta, the coronary arteries, the carotid arteries, the cerebrovascular arteries, the renal arteries, the iliac arteries, the fermoral arteries and the popliteal arteries.

The compound is may be selected from, for example: trientine (triene), ethylenediaminetetraacetic acid (EDTA), diethylenetriaminetetraacetic acid (DPTA), 2,2,2 tetramine tetrahydrochloride (TETA), 2,3,2 tetramine tetrahydrochloride, D-penicillamine (DPA), 1,4,8,11 tetraazacyclotretradecane (Cyclam), 5,7,7',12,14,14' hexamethyl-1,4,8,11 tetraazacyclotretradecane (Cyclam S), Sodium 2,3 dimercaptopropane-1-sulfonate (DMPS), N-acetylpenicillamine (NAPA), D-Penicillamine (PA),' Desferroxamine, 2,3-dimercaptopropanol (BAL), 2,3-dimercaptosuccinic acid (DMSA), trithiomolybdate, 3-7-Diazanonan-1,9-diamin (BE 6184), 1,4,8,11-tetraazacyclotetradecane-1,4,8,11-tetraacetic acid, 1,4,8,11-tetraazabicyclo[6.6.2]hexadecane, 4,11-bis(N,N-diethyl-amidomethyl)-1,4,8,11-tetraazabicyclo[6.6.2]hexadecane, 4,11-bis(amidoethyl)-1,4,8,11-tetraazabicyclo[6.6.2]hexadecane, melatonin, clioquinol, cuprizone, N,N'-diethyldithiocarbamate, zinc acetate, zinc salts, bathocuproinedisulfonic acid, bathocuprinedisulfonate, neocuproine (2,9-dimethyl-1,10-phenanthroline), tetrathiomolybdate, trimetazidine, triethylene tetramine tetrahydrochloride, 2,3,2-tetraamine, pyridine-2,6-bis(thiocarboxylic acid) or pyrrolidine dithiocarbamate, tetraethylenepentamine, N,N,N',N-tetrakis(2-pyridylemethyl)ethylenediamine, 1,4,7,11-tetraazaundecane tetrahydrochloride, tetraethylenepentamine pentahydrochloride, D-Penicillamine (DPA), 1,10-orthophenanthroline, 3,4-Dihydroxybenzoic acid, 2,2'-bicinchinonic acid, diamsar, 3,4',5, trihydroxystilbene (resveratrol), mercaptodextran, o-phenanthroline, disulfiram (antabuse), sar, calcium trisodium. diethylenetriaminepentaacetate (salt of cpd above), and methimazole (1-methyl-2-thiolimidazole).

Preferably the compound is trientine or a trientine-type copper chelation agent.

Preferably the use involves pharmaceutically acceptable excipients, diluents and/or carriers.

The invention is also a dosage unit resulting from the use.

In another aspect the invention is a method of treating a mammalian patient (e.g.; a human being) at risk of developing, with suspected or with actual tissue damage to the myocardium, the vascular tree and/or organs dependent on the vascular tree, which method comprises or includes the step of subjecting the patient mammal to and/or administering to the patient mammal one or more agents capable of decreasing the copper values content of the patient thereby to better enable tissue repair. In a related aspect, the patient does not have Wilson's Disease yet has elevated copper values. Preferably the agent(s) is (are) a chelator (chelators) of copper. It is also preferred but not required that the agent(s) has (have) an affinity for copper over that of iron.

In still another aspect the invention is a method of treating a mammalian patient (for example, a human being) at risk of developing, with suspected or with actual tissue disease to the myocardium, the vascular tree and/or organs dependent on the vascular tree, which method comprises or includes the steps of determining the copper status of the patient, and if the copper status of a patient is elevated yet, for example, the patient is not suffering from Wilson's Disease, subjecting the patient to and/or administering to the patient one or more agents capable of decreasing the patient's copper values content thereby to better enable tissue repair.

The method may involve continual or periodic evaluating or monitoring of the copper status of the patient.

The determination of the copper status can be by reference to extra-cellular copper values.

The decreasing of the patient's copper values content may be, but is not necessarily, from an elevated status being that typical of the copper values status of a human patient suffering from type 2 diabetic mellitus or other disease, disorder or condition, for example, over that of a non sufferer.

The method may include the step of diagnosing and/or evaluating or monitoring glucose levels.

The method may include the step of diagnosing and/or evaluating or monitoring postprandial glycemia.

The method may include the step of diagnosing and/or evaluating or monitoring renal function.

The method may include the step of diagnosing and/or evaluating or monitoring hypertension.

The method may include the step of diagnosing and/or evaluating or monitoring insulin resistance.

The method may include the step of diagnosing and/or evaluating or monitoring impaired glucose tolerance.

The method may include the step of diagnosing and/or evaluating or monitoring obesity.

The method may include the step of diagnosing alcoholism.

The method may include the step of diagnosing and/or evaluating or monitoring a glucose mechanism abnormality of the patient.

In one aspect, the abnormality is type 2 diabetes mellitus, IGT and/or IFG.

The method may also include the step of diagnosing and/or evaluating or monitoring macrovascular, microvascular, toxic and/or metabolic damage in the patient.

Damage to be prevented, treated, or ameliorated can be damage resulting from or associated with any one or more of: (i) disorders of the heart muscle (for example, cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; (ii) atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; (iii) toxic, drug-induced, and metabolic (including hypertensive and/or diabetic disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; (iv) plaque rupture of atheromatous lesions of major blood vessels such as the aorta, the coronary arteries, the carotid arteries, the cerebrovascular arteries, the renal arteries, the iliac arteries, the fermoral arteries and the popliteal arteries.

In another aspect the present invention provides a method of treating a mammalian patient (for example, a human being) at risk of developing, with suspected or with actual disease to the myocardium, the vascular tree and/or organs dependent therefrom, which method comprises or includes the step of subjecting the patient to and/or administering to the patient one or more agents capable of decreasing the copper values content of the patient.

In another aspect the present invention provides a method of treating a mammalian patient (for example, a human being) at risk of developing, with suspected or with actual disease to the myocardium, the vascular tree and/or organs dependent on the vascular tree, which method comprises or includes the steps of determining the copper status of the patient, and if the copper status of a patient is undesirably elevated or above that of a normal patient yet, for example, the patient is not suffering from Wilson's Disease, subjecting the patient to and/or administering to the patient one or more agents capable of decreasing the patient's copper values content. The method may also involve periodic or continual evaluating or monitoring of the copper status of the patient. The determination of the copper status is desirably by reference to extra cellular copper values.

Preferably the subjection or administration is with any one or more of the agents as herein referenced defined, preferred and/or exemplified.

In another aspect the present invention is the use of a compound (a) which itself in vivo or (b) which has at least one metabolite in vivo which is a copper chelator or otherwise reduces available copper values for the production of a pharmaceutical composition able to reduce the level of copper in a mammal (for example, in heart tissue and/or in the walls of major blood vessels respectively) for the treatment (for example, by repair of tissue resulting) of a disease (other than, for example, Wilson's Disease) of any one or more of the kinds referred to herein.

In another aspect the invention is a method of improving tissue repair in a mammalian patient not suffering from Wilson's Disease yet having an elevated copper values body content, said method comprising or including the step of subjected the patient to, and/or administering to the patient, an agent effective in lowering the copper values content of the patient's body sufficient to improve tissue repair by restoration or substantially restoration of normal tissue stem cell responses. In still another aspect, there is at least one copper values status determination.

In another aspect the present invention provides a method of treating a mammal (for example, a human being) at risk of developing, with suspected or with actual diabetic cardiomyopathy which comprises or includes the step of subjecting the patient mammal to and/or administering to the patient mammal one or more agents capable of decreasing the copper values content of the patient.

Such agent(s) may comprise or include copper chelators and/or may include compounds or compositions otherwise capable of decreasing the copper values content of the patient (for example, zinc (for example, as a suitable salt such as the gluconate salt) or tri thiomolybdate (also a copper chelator) which tend to prevent copper absorption by a patient).

The method may include an additional step or steps of evaluating or monitoring the copper values of the patient prior to, simultaneously with and/or subsequent to the patient being subjected to or being administered with the agent(s).

The method may also include, for example, diagnosis of the patient as a diabetic.

In another aspect the present invention provides a method of treating a mammal (for example, a human being) at risk of developing, with suspected or with actual diabetic acute myocardial infarction which comprises or includes the step of subjecting the patient mammal to and/or administering to the patient mammal one or more agents capable of decreasing the copper values content of the patient. Such agent(s) may comprise or include copper chelators and/or may include compounds or compositions otherwise capable of decreasing the copper values content of the patient (for example; zinc (e.g.; as a suitable salt such as the gluconate) or trithiomolybdate (also a copper chelator) which tend to prevent copper absorption by a patient).

The method may include an additional step or steps of evaluating or monitoring the copper values of the patient prior to, simultaneously with and/or subsequent to the patient being subjected to or being administered with the agent(s). The method may also include, for example, diagnosis of the patient as a diabetic.

In still another aspect the present invention provides a method of treating a mammal (for example, a human being) at risk of developing, with suspected or with actual diabetic hypertensive cardiomyopathy which comprises or includes the step of subjecting the patient mammal to and/or administering to the patient one or more agents capable of decreasing the copper values content of the patient. Such agent(s) may comprise or include copper chelators and/or may include compounds or compositions otherwise capable of decreasing the copper values content of the patient (for example, zinc (for example, as a suitable salt such as the gluconate form) or trithiomolybdate (also a copper chelator) which tend to prevent copper absorption by a patient). The method may include an additional step or steps of evaluating or monitoring the copper values of the patient prior to, simultaneously with and/or subsequent to the patient being subjected to or being administered with the agent(s). The method may also include, for example, diagnosis of the patient as a diabetic.

In yet another aspect the present invention provides a method of treating a mammal (for example, a human being) at risk of developing, with suspected or with actual acute myocardial infarction (AMI) associated with impaired glucose tolerance (IGT) which comprises or includes the step of subjecting the patient mammal to and/or administering to the patient one or more agents capable of reducing the copper values content of the patient. Such agent(s) may comprise or include copper chelators and/or may include compounds or compositions otherwise capable of reducing the copper values content of the patient (for example, zinc (for example, as a suitable salt including the gluconate form) or trithiomolybdate (also a copper chelator) which tend to prevent copper absorption by a patient). The method may include an additional step or steps of evaluating or monitoring the copper values of the patient prior to, simultaneously with and/or subsequent to the patient being subjected to or being administered with the agent(s). The method may also include diagnosis of the patient, for example, as a diabetic. The method may also include one or both of the additional steps of diagnosis of the patient with myocardial infarction and/or impaired glucose tolerance.

In another aspect the present invention provides a method of treating a mammal (for example, a human being) at risk of developing, with suspected or with actual acute myocardial infarction associated with impaired fasting glucose (IFG) which comprises or includes the step of subjecting the patient mammal to and/or administering to the patient mammal one or more agents capable of reducing the copper values content of the patient. Such agent(s) may comprise or include copper chelators and/or may include compounds or compositions otherwise capable of reducing the copper values content of the patient (for example, zinc (for example, as a suitable salt including the gluconate form) or trithiomolybdate (also a copper chelator) which tend to prevent copper absorption by a patient). The method may include an additional step or steps of evaluating or monitoring the copper values of the patient prior to, simultaneously with and/or subsequent to the patient being subjected to or being administered with the agent(s). The method may also include diagnosis of the patient, for example, as a diabetic. The method can also include one or both of the additional steps of diagnosis of the patient with myocardial infarction and/or impaired fasting glucose.

In still another aspect the present invention provides a method of treating a mammal (for example, a human being) at risk of developing, with suspected or with actual hypertensive cardiomyopathy associated with IGT which comprises or includes the step of subjecting the patient mammal to and/or administering to the patient mammal one or more agents capable of reducing the copper values content of the patient. Such agent(s) may comprise or include copper chelators and/or may include compounds or compositions otherwise capable of reducing the copper values content of the patient (for example, zinc (for example, as a suitable salt such as the gluconate form) or trithiomolybdate (also a copper chelator) which tend to prevent copper absorption by a patient). The method may also include an additional step or steps of evaluating or monitoring the copper values of the patient prior to, simultaneously with and/or subsequent to the patient being subjected to or being administered with the agent(s). The method may also include diagnosis of the patient, for example, as a diabetic. The method may also include the additional step or steps of diagnosing the patient as a hypertensive and/or as being subjected to IGT and/or suffering from actual hypertensive cardiomyopathy.

In yet another aspect the present invention provides a method of treating a mammal (for example, a human being) at risk of developing, with suspected or with actual hypertensive cardiomyopathy associated with IFG which comprises or includes the step of subjecting the patient mammal to and/or administering to the patient mammal one or more agents capable of reducing the copper values content of the patient. Such agent(s) may comprise or include copper chelators and/or may include compounds or compositions otherwise capable of reducing the copper values content of the patient (for example; zinc (for example, as a suitable salt such as the gluconate) or trithiomolybdate (also a copper chelator) which tend to prevent copper absorption by a patient). The method may also include an additional step or steps of evaluating or monitoring the copper values of the patient prior to, simultaneously with and/or subsequent to the patient being subjected to or being administered with the agent(s). The method may also include diagnosis of the patient, for example, as a diabetic. The method may further include the additional step or steps of diagnosing the patient, for example, as a hypertensive and/or having IFG and/or having hypertensive cardiomyopathy.

In another aspect the present invention provides a method of treating a mammal (for example, a human being) at risk of developing, with suspected or with actual ischaemic cardiomyopathy associated with IGT which comprises or includes the step of subjecting the patient mammal to and/or administering to the patient mammal one or more agents capable of reducing the copper values content of the patient. Such agent(s) may comprise or include copper chelators and/or may include compounds or compositions otherwise capable of decreasing the copper values content of the patient (for example, zinc (for example, as a suitable salt such as the gluconate form) or trithiomolybdate (also a copper chelator) which tend to prevent copper absorption by a patient). The method may also include an additional step or steps of evaluating or monitoring the copper values of the patient prior to, simultaneously with and/or subsequent to the patient being subjected to or being administered with the agent(s). The method may further include diagnosis of the patient, for example, as a diabetic. The method may also include the additional step of determining the patient is subject to ischemic disease and/or is subject to IGT and/or is suffering from ischemic cardiomyopathy.

In yet another aspect the present invention provides a method of treating a mammal (for example, a human being) at risk of developing, with suspected or with actual ischemic cardiomyopathy associated with IFG which comprises or includes the step of subjecting the patient mammal to and/or administering to the patient mammal one or more agents capable of decreasing the copper values content of the patient. Such agent(s) may comprise or include copper chelators and/or may include compounds or compositions otherwise capable of decreasing the copper values content of the patient (for example, zinc (for example, as a suitable salt such as the gluconate form) or trithiomolybdate (also a copper chelator) which tend to prevent copper absorption by a patient). The method may include an additional step or steps of evaluating or monitoring the copper values of the patient prior to, simultaneously with and/or subsequent to the patient being subjected to or being administered with the agent(s). The method may also include diagnosis of the patient, for example, as a diabetic. The method may include the additional step or steps of diagnosing the patient as ischaemic and/or having IFG and/or suffering from ischemic cardiomyopathy. The method may include the additional step or steps of diagnosing the patient as subject to ischaemic disease and/or suffering from coronary heart disease (CHD) and/or suffering from ischaemic cardiomyopathy.

In another aspect the present invention provides a method of treating a mammal (for example, a human being) at risk of developing, with suspected or with actual ischaemic cardiomyopathy associated with coronary heart disease (CHD) which comprises or includes the step of subjecting the patient mammal to and/or administering to the patient mammal one or more agents capable of decreasing the copper values content of the patient. Such agent(s) may comprise or include copper chelators and/or may include compounds or compositions otherwise capable of decreasing the copper values content of the patient (for example, zinc (for example, as a suitable salt such as the gluconate from) or trithiomolybdate (also a copper chelator) which tend to prevent copper absorption by a patient). The method may include an additional step or steps of evaluating or monitoring the copper values of the patient prior to, simultaneously with and/or subsequent to the patient being subjected to or being administered with the agent(s). The method may also include diagnosis of the patient, for example, as a diabetic. The method may include the additional step or steps of diagnosing the patient as suffering from acute myocardial infarction.

In another aspect the present invention provides a method of treating a mammal (for example, a human being) at risk of developing, with suspected or with actual acute myocardial infarction not associated with any abnormality of the glucose metabolism which comprises or includes the step of subjecting the patient mammal to and/or administering to the patient mammal one or more agents capable of decreasing the copper values content of the patient. Such agent(s) may comprise or include copper chelators and/or may include compounds or compositions otherwise capable of decreasing the copper values content of the patient (for example, zinc (for example, as a suitable salt such as the gluconate) or trithiomolybdate (also a copper chelator) which tend to prevent copper absorption by a patient). The method may include an additional step or steps of evaluating or monitoring the copper values of the patient prior to, simultaneously with and/or subsequent to the patient being subjected to or being administered with the agent(s). The method may include the additional step or steps of diagnosing the patient, for example, as hypertensive and/or suffering from hypertensive cardiomyopathy.

In another aspect the present invention provides a method of treating a mammal (for example, a human being) at risk of developing, with suspected or with actual hypertensive cardiomyopathy not associated with any abnormality of the glucose metabolism which comprises or includes the step of subjecting the patient mammal to and/or administering to the patient one or more agents capable of decreasing the copper values content of the patient. Such agent(s) may comprise or include copper chelators and/or may include compounds or compositions otherwise capable of decreasing the copper values content of the patient (for example, zinc (for example, as a suitable salt such as the gluconate form) or trithiomolybdate (also a copper chelator) which tend to prevent copper absorption by a patient). The method may include an additional step or steps of evaluating or monitoring the copper values of the patient prior to, simultaneously with and/or subsequent to the patient being subjected to or being administered with the agent(s). The method may also include diagnosis of the patient, for example, as a diabetic. The method may also include the additional step or steps of diagnosing the patient, for example, as hypertensive and/or suffering from hypertensive cardiomyopathy.

In yet a further aspect the present invention provides a method of treating a mammal (for example, a human being) at risk of developing, with suspected or with actual ischemic cardiomyopathy not associated with any abnormality of the glucose metabolism (irrespective of whether or not such ischemic cardiomyopathy is associated with coronary heart disease or not) which comprises or includes the step of subjecting the patient mammal to and/or administering to the patient one or more agents capable of decreasing the copper values content of the patient. Such agent(s) may comprise or include copper chelators and/or may include compounds or compositions otherwise capable of decreasing the copper values content of the patient (for example, zinc (for example, as a suitable salt such as the gluconate form) or trithiomolybdate (also a copper chelator) which tend to prevent copper absorption by a patient). The method may include an additional step or steps of evaluating or monitoring the copper values of the patient prior to, simultaneously with and/or subsequent to the patient being subjected to or being administered with the agent(s). The method may also include diagnosis of the patient, for example, as a diabetic. The method may include the additional step or steps of diagnosing the patient as suffering from, for example, ischemic disease and/or ischemic cardiomyopathy.

In a further aspect the present invention provides a method of treating a human at risk of developing, with suspected or with actual cardiomyopathy which comprises or includes the steps of categorizing the human by reference to (a) whether suffering from one or more of type 2 diabetes, impaired glucose tolerance (IGT) and impaired fasting glucose (IFG), and/or (b) copper status, and (provided the patient (a) is suffering from type 2 diabetes and/or (IGT) and/or IFG, and/or (b) is not biochemically or clinically or undesirably copper deficient) subjecting the patient to a regimen with a view to decreasing the presence of copper values. There may also be a step of ensuring by reference to heart function that the patient is benefiting from the copper decreasing regimen.

In a further aspect the present invention provides a method of treating a human at risk to developing, with suspected or with actual acute myocardial infarction which comprises or includes the steps of categorizing the human by reference to (a) whether suffering from one or more Type 2 diabetes, impaired glucose tolerance (IGT) and impaired fasting glucose (IFG), and/or (b) copper status, and (provided the patient (a) is suffering from Type 2 diabetes and/or IGT and/or IGF, and/or (b) is not biochemically or clinically or undesirably copper deficient) subjecting the patient to an copper chelation and/or other copper values decreasing regimen with a view to decreasing the presence of copper. Step (i) may also includes reference to (c) heart function. Alternatively and/or additionally benefit to patient is assessed by reference to heart function.

In another aspect the present invention provides a method of treating a human at risk of developing, with suspected or with actual hypertensive cardiomyopathy which comprises or includes the steps of categorizing the human by reference to (a) whether hypertensive, and/or (b) copper status; and subjecting the patient to an copper chelation and/or other copper values decreasing regimen with a view to decreasing the presence of copper whilst preferably ensuring patient does not have or does not develop a copper deficiency. Step (i) may also include one or both references to (b) copper status and/or (c) heart function. There may also be a step of ensuring by reference to heart function that the patient is benefiting from the copper chelation regimen.

In a further aspect the present invention provides a method of treating a human at risk to developing, with suspected or with actual ischemic cardiomyopathy which comprises or includes the steps of categorizing the human by reference to (a) whether suffering from ischaemia, and/or (b) copper status; and subjecting the patient to a copper chelation and/or other copper values decreasing regimen with a view to decreasing the presence of copper whilst preferably ensuring patient does not have or does not develop any copper deficiency.

In still another aspect the present invention provides a method of treating a human at risk of developing, with suspected or with actual cardiomyopathy which comprises or includes the steps of categorizing the human as a candidate patient by reference to at least (a) whether suffering from Type 2 diabetes, (IGT), impaired fasting glucose (IFG) and/or hypertensive impaired glucose tolerance, and (b) heart function, and subjecting the patient to an copper chelation and/or other copper values decreasing regimen with a view to decreasing the presence of copper whilst preferably ensuring patient does not have or does not develop any copper deficiency. There may also be a step of ensuring by reference to heart function that the patient is benefiting from the copper chelation regimen.

In a further aspect the present invention provides a method of treating a human or other mammal at risk to developing, with suspected or with actual (I) arterial, (II) arterial and coronary and/or other organ, and/or (III) heart muscle disease which comprises or includes the steps of categorizing the human or other mammal as a candidate patient and subjecting the patient to an copper chelation and/or other copper values decreasing regimen with a view to decreasing the presence of copper. Step (i) may also include a determination of the copper status of the human or other mammal. There may also be a step of ensuring by reference to heart and/or arterial function that the patient is benefiting from the copper chelation and/or other copper values decreasing regimen.

In another aspect, the one or more agents capable of decreasing the copper values content of the patient, if a chelator, has a preferential affinity for copper values over the values of other trace metals (such as iron, zinc and/or manganese). Preferably the preferential affinity for copper values is such that copper excess of from about 100% to about 500% over that of a normal healthy mammal of the species can be controlled to such normal levels or approaching such normal levels without leading to depletion or excessive decreases in iron, zinc and/or manganese. With the chelators such as those herein referred to and the suitable salts of zinc it is possible to selectively decrease the copper values in the body as a whole even though it is believed there is little decrease in copper values in the intra cellular tissue. Without being bound by this mechanism, it is believed that the decrease is primarily extracellular (for example, interstitial, on the exterior of cells and/or on collagen).

In another aspect the present invention provides a method of treatment, for example, that includes the methodology of either FIG. 3 or 4 of the accompanying drawings.

In a further aspect the present invention provides a method of treating a human having type 2 diabetes or impaired glucose intolerance at risk of developing, with suspected or with actual cardiomyopathy which comprises or includes subjecting the patient to an copper chelation regimen with a view to decreasing the presence of chelatable copper to heart tissue whilst at least on occasions having monitored and/or evaluating or monitoring the patient to avoid a copper deficit. The patient may also be or have been categorized to ensure that the regimen is not commenced and/or does not continue should the patient be copper deficient.

In a further aspect the present invention provides a method of treating a human having type 2 diabetes or impaired glucose intolerance at risk of developing, with suspected or with actual macrovascular disease which comprises or includes subjecting the patient to a total body copper content decreasing regimen. The patient may also be or have been categorized to ensure that the regimen is not commenced and/or does not continue should the patient be copper deficient.

In still a further aspect or as one preferment the present invention provides a method of treating a human at risk of developing, with suspected or with actual cardiomyopathy related heart failure which comprises or includes decreasing the levels of chelatable and/or other copper values of such patient preferably without taking the patient into undesirable copper values or copper deficit.

In yet a further aspect the present invention provides a method of treating a human at risk of developing, with suspected or with actual macrovascular disease of the arterial tree which comprises or includes decreasing the levels of chelatable copper in the walls of major blood vessels of such patient without taking the patient into undesirable copper values or copper deficit.

In yet another aspect the present invention provides a method of treating a human at risk of developing, with suspected or with actual cardiomyopathy which comprises or includes the steps of categorizing the human as being at risk of developing, with suspected or with actual cardiomyopathy, and subjecting the patient to an copper chelation regimen with a view to decreasing the presence of copper. The copper chelation regimen may include or be subject to evaluating or monitoring to ensure the patient does not have or does not develop undesirable copper values or a copper deficiency. The categorization may rely on an initial check of heart function and the patient being categorized for the copper chelation regimen when that heart function is below normal. The heart function evaluating or monitoring may also continue into or beyond the copper chelation regimen. The categorization may include a determination of the patient suffering from type 2 diabetes or impaired glucose tolerance. The categorization may also involve a reference to copper status of the patient prior to any commencement or substantial duration of the copper chelation regimen to ensure the patient does no have or does not develop undesirable copper values or a copper deficiency.

In any of the foregoing procedures the following (any one, some or all) arise or be involved. The compound may be a copper chelator which in the mammal is substantially without an ability to generate free radicals in significant qualities and which also in the mammal at the dosage regimen to be given will not chelate copper down to a depletion state in the mammal. The administration is at a dosage regimen less than that which for a patient suffering from classical copper overload would have the effect of decreasing the copper levels of that patient to normal. The administration is at a dosage regimen (whether dependent upon dosage unit(s) and/or frequency) that does not or will not reduce a patient of normal copper levels to a deficiency state. The regimen is in concert (serial, simultaneous or otherwise) with a regimen to antagonize fructosamine oxidase. The dosage unit(s) is (are) the dosage unit(s) of a copper decreasing regimen. The regimen may run in concert with any of the regimens disclosed in WO 00/18392. The use involves pharmaceutically acceptable diluents and/or carriers. The composition is for use in a method referenced, suggested or identified herein.

The present invention also provides a dosage unit resulting from or for any such use.

BRIEF DESCRIPTION OF THE DRAWINGS

FIG. 2 is a hypothesis of the mechanisms involved applicable to cardiomyopathy and macrovascular disease in a patient with type 2 diabetes or impaired glucose tolerance, for example, such a hypothesis showing reliance on a possible fructosamine oxidase/superoxide dismutase generation of a precursor to an copper catalyzed reaction (the Haber-Weiss Reaction) which generates the harmful free radicals.

FIG. 27 is a table comparing the copper and iron excretion in the animals receiving trientine or saline, which is a statistical analysis using a mixed linear model.

DETAILED DESCRIPTION OF THE INVENTION

Figure 1:
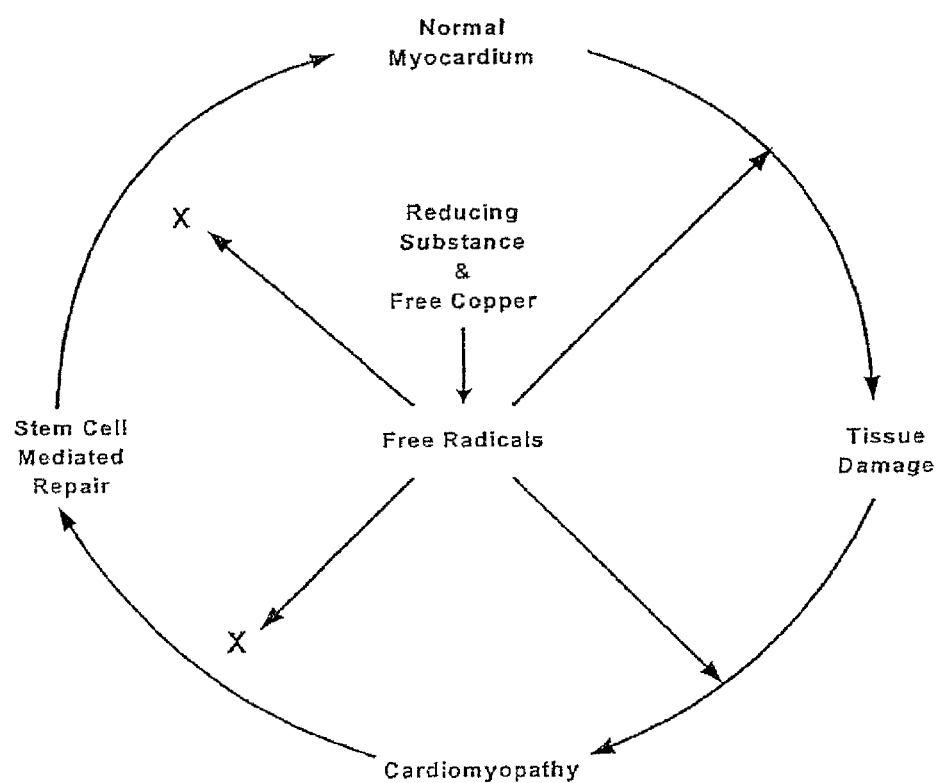
FIG. 1 is a diagram showing various pathways addressed by the present invention.
Figure 3:
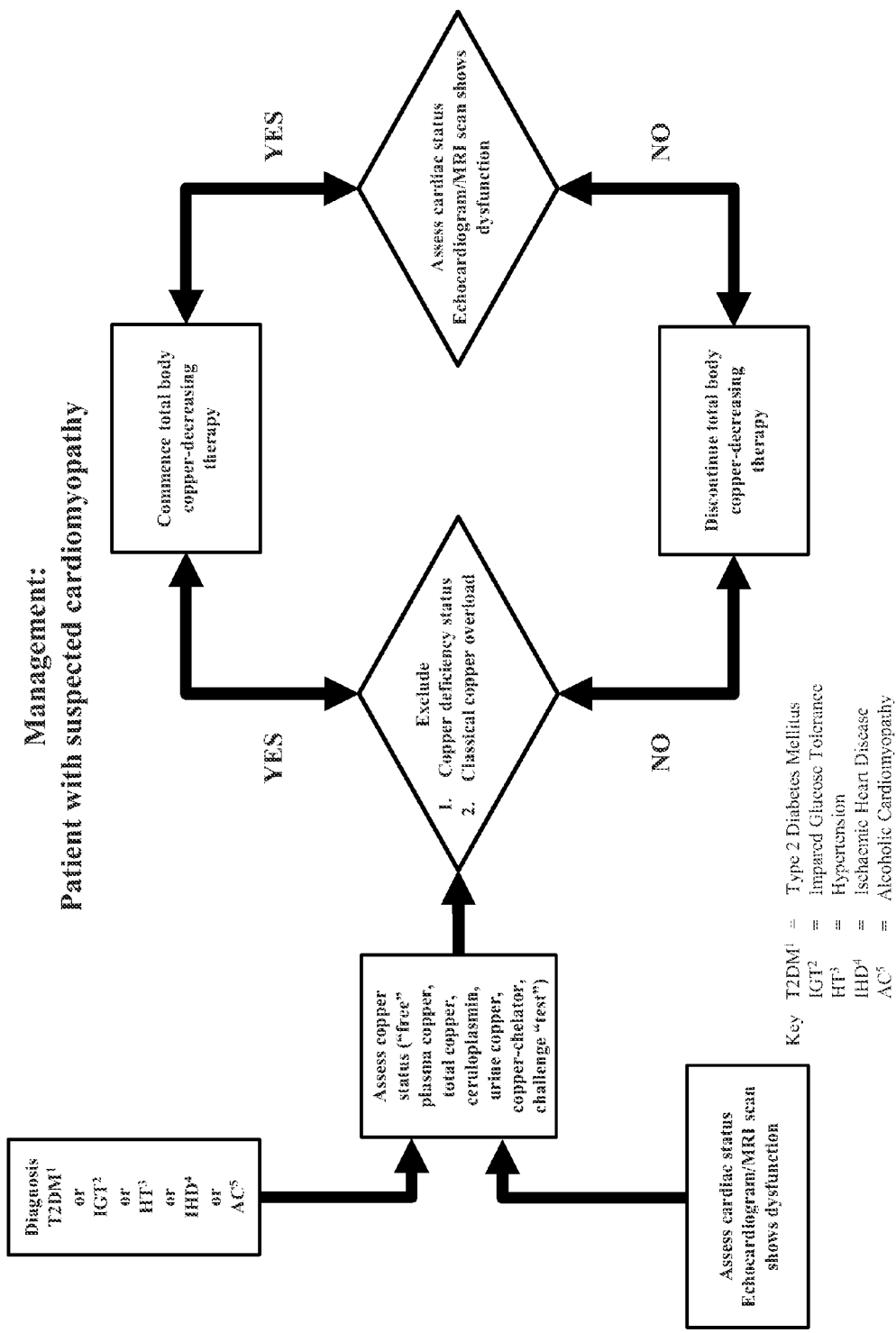
FIG. 3 is the methodology for a human patient with suspected cardiomyopathy under the present invention.
Figure 4:
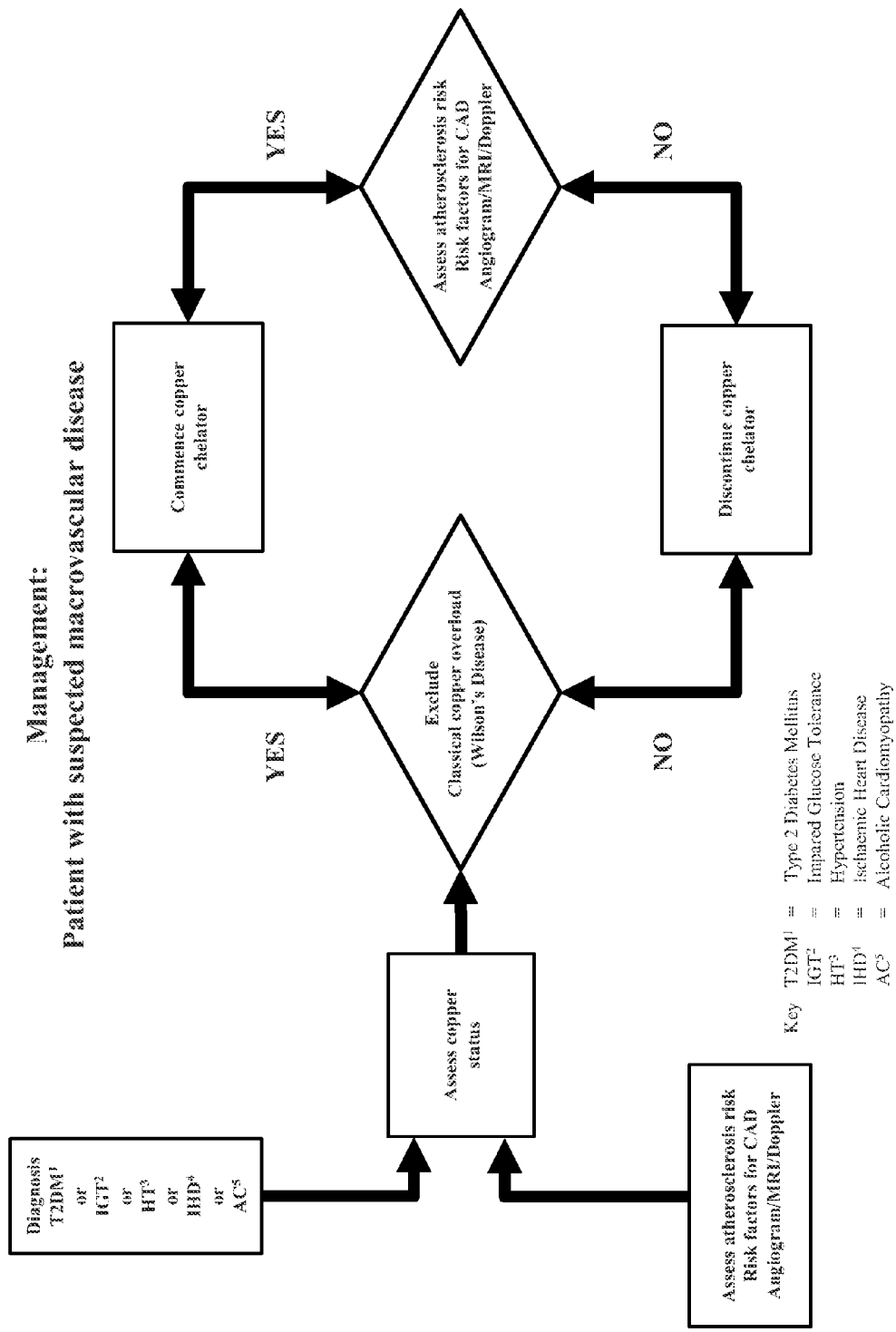
FIG. 4 is a similar diagram to that of FIG. 3 but in respect of a patient with suspected macrovascular disease.

The invention is related to and describes the methods relating to discoveries surrounding increased tissue copper and mechanisms leading to tissue damage, including nerve and vascular damage, for example, diabetic nerve and/or vascular damage. It is believed, without wishing to be bound by any particular mechanism or theory of operation or effectiveness, that tissue accumulation of trace metals plays a role in the mechanisms of tissue damage in diabetes as well as in other disorders, diseases, and conditions as set forth or referenced or suggested herein.

Histological evidence from experiments showed that six months of treatment with trientine appears to protect the hearts of diabetic Wistar rats from development of diabetic damage (cardiomyopathy) as judged by histology. The doses of trientine required for copper and iron to be excreted in the urine have also been investigated, for example, as well as possible differences between the excretion of these metals in diabetic and nondiabetic animals. For example, the excretion profiles of copper and iron in the urine of normal and diabetic rats were compared after acute intravenous administration of increasing doses of trientine. Additionally, it was ascertained whether acute intravenous administration of trientine has acute adverse cardiovascular side effects. Methods used in the experimentals were as follows.

Male Wistar rats (n=28, 303±2.9 g) were divided randomly into diabetic and nondiabetic groups. Following induction of anesthesia (5% halothane and 2 l·min$^{-1}$ O$_2$), animals in the diabetic group received a single intravenous dose of streptozotocin (STZ, 55 mg·kg$^{-1}$ body weight, Sigma; St. Louis, Mo.) in 0.5 ml saline administered via the tail vein. Nondiabetic animals received an equivalent volume of saline. Following injection, both diabetic and nondiabetic rats were housed in like-pairs and provided with access to normal rat chow (Diet 86 pellets; New Zealand Stock Feeds, Auckland, NZ) and deionized water ad libitum. Blood glucose and body weight were measure at day 3 following STZ/saline injection and then weekly throughout the study. Diabetes was identified by polydipsia, polyuria and hyperglycemia (>11 mmol·l$^{-1}$, Advantage II, Roche Diagnostics, NZ Ltd).

Six to seven weeks (mean=44±1 days) after administration of STZ, animals underwent either a control or drug experimental protocol. All animals were fasted overnight prior to surgery but continued to have ad libitum access to deionized water. Induction and maintenance of surgical anesthesia was by 3-5% halothane and 2 l·min$^{-1}$ O$_2$. The femoral artery and vein were cannulated with a solid-state blood pressure transducer (Mikrotip™ 1.4F, Millar Instruments, Texas, USA) and a saline filled PE 50 catheter respectively. The ureters were exposed via a midline abdominal incision, cannulated using polyethylene catheters (external diameter 0.9 mm, internal diameter 0.5 mm) and the wound sutured closed. The trachea was cannulated and the animal ventilated at 70-80 breaths·min$^{-1}$ with air supplemented with O$_2$ (Pressure Controlled Ventilator, Kent Scientific, Connecticut, USA). The respiratory rate and end-tidal pressure (10-15 cmH$_2$O) were adjusted to maintain end-tidal CO$_2$ at 35-40 mm Hg (SC-300 CO$_2$ Monitor, Pryon Corporation, Wisconsin, USA). Body temperature was maintained at 37° C. throughout surgery and the experiment by a heating pad. Estimated fluid loss was replaced with intravenous administration of 154 mmol·l$^{-1}$ NaCl solution at a rate of 5 ml·kg$^{-1}$·h$^{-1}$.

Following surgery and a 20 min stabilization period, the experimental protocol was started. Trientine was administered intravenously over 60 s in hourly doses of increasing concentration (0.1, 1.0, 10 and 100 mg·kg$^{-1}$ in 75 μl saline followed by 125 μl saline flush). Control animals received an equivalent volume of saline. Urine was collected in 15 min aliquots throughout the experiment in pre-weighed polyethylene epindorph tubes. At the end of the experiment a terminal blood sample was taken by cardiac puncture and the separated serum stored at −80° C. until future analysis. Hearts were removed through a rapid mid-sternal thoracotomy and processed as described below.

Mean arterial pressure (MAP), heart rate (HR, derived from the MAP waveform) oxygen saturation (Nonin 8600V Pulse Oximeter, Nonin Medical Inc., Minnesota, USA) and core body temperature, were all continuously monitored throughout the experiment using a PowerLab/16 s data acquisition module (AD Instruments, Australia). Calibrated signals were displayed on screen and saved to disc as 2 s averages of each variable.

Instrumentation: A Perkin Elmer (PE) Model 3100 Atomic Absorption Spectrophotometer equipped with a PE HGA-600 Graphite Furnace and PE AS-60 Furnace Autosampler was used for Cu and Fe determinations in urine. Deuterium background correction was employed. A Cu or Fe hollow-cathode lamp (Perkin Elmer Corporation) was used and operated at either 10 W (Cu) or 15 W (Fe). The 324.8 nm atomic line was used for Cu and the 248.3 nm atomic line for Fe. The slit width for both Cu and Fe was 0.7 nm. Pyrolytically coated graphite tubes were used for all analyses. The injection volume was 20 μL. A typical graphite furnace temperature program is shown below.

GF-AAS Temperature Program

| Procedure | Temp/° C. | Ramp/s | Hold/s | Int. Flow/mL min$^{-1}$ |
|---|---|---|---|---|
| Drying | 90 | 1 | 5 | 300 |
|  | 120 | 60 | 5 | 300 |
| Pre-treatment | 1250* | 20 | 10 | 300 |
|  | 20 | 1 | 10 | 300 |
| Atomization - Cu/Fe | 2300/2500 | 1 | 8 | 0 |
| Post-treatment | 2600 | 1 | 5 | 300 |

*A pre-treatment temperature of 1050° C. was used for tissue digest analyses

Cu, Fe and Zn in tissue digests were also determined at Hill Laboratories (Hamilton, New Zealand) using either a PE Sciex Elan-6000 or PE Sciex Elan-6100 DRC ICP-MS. The operating parameters are summarized in the table below.

Instrumental Operating Parameters for ICP-MS

| Parameter | Value |
|---|---|
| Inductively coupled plasma | |
| Radiofrequency power | 1500 W |
| Argon plasma gas flow rate | 15 l·min$^{-1}$ |
| Argon auxiliary gas flow rate | 1.2 l·min$^{-1}$ |
| Argon nebuliser gas flow rate | 0.89 l·min$^{-1}$ |
| Interface | |
| Sampler cone and orifice diameter | Ni/1.1 mm |
| Skimmer cone and orifice diameter | Ni/0.9 mm |
| Data acquisition parameters | |
| Scanning mode | Peak hopping |
| Dwell time | 30 ms (Cu, Zn)/100 ms (Fe) |
| Sweeps/replicate | 20 |
| Replicates | 3 |
| Sample uptake rate | 1 ml·min$^{-1}$ |

Reagents: All reagents used were of the highest purity available and at least of analytical grade. GF-AAS standard working solutions of Cu and Fe were prepared by stepwise dilution of 1000 mg·l$^{-1}$ (Spectrosol standard solutions; BDH). Water was purified by a Millipore Milli-Q ultra-pure water system to a resistivity of 18 MΩ. Standard Reference Material 1577b Bovine Liver was obtained from the National Institute of Standards and Technology and used to evaluate the efficiency of tissue digestion. The results obtained are reported below.

| GF-AAS and ICP-MS results for NIST SRM 1577b bovine liver* | | | |
|---|---|---|---|
| Element | Certified value | GF-AAS | ICP-MS |
| Cu | 160 ± 8 | 142 ± 12 | 164 ± 12 |
| Fe | 184 ± 15 | 182 ± 21 | 166 ± 14 |
| Zn | 127 ± 16 | — | 155 ± 42 |

*Measured in μg·g$^{-1}$ of dry matter.

Samples were pretreated as follows:

Urine:

Urine was collected in pre-weighed 1.5 ml micro test tubes (eppendorf). After reweighing, the urine specimens were centrifuged and the supernatant diluted 25:1 with 0.02 M 69% Aristar grade HNO$_3$. The sample was stored at 4° C. prior to GF-AAS analysis. If it was necessary to store a sample for a period in excess of 2 weeks, it was frozen and kept at −20° C.

Heart:

Following removal from the animal, the heart was cleaned of excess tissue, rinsed in buffer to remove excess blood, blotted dry and a wet ventricular weight recorded. Using titanium instruments a segment of left ventricular muscle was dissected and placed in a pre-weighed 5.0 ml polystyrene tube. The sample was freeze-dried overnight to constant weight before 0.45 ml of 69% Aristar grade HNO$_3$ was added. The sample tube was heated in a water bath at 65° C. for 60 minutes. The sample was brought to 4.5 ml with Milli-Q H$_2$O. The resulting solution was diluted 2:1 in order to reduce the HNO$_3$ concentration below the maximum permitted for ICP-MS analysis.

Serum:

Terminal blood samples were centrifuged and serum treated and stored as per urine until analysis. From the trace metal content of serum from the terminal blood sample and urine collected over the final hour of the experiment, renal clearance was calculated using the following equation: renal clearance of trace metal=(a) the concentration of metal in urine (μg·μl$^{-1}$) times (b) the rate of urine flow (μl·min$^{-1}$), divided by (c) the concentration of metal in serum (μg·μl$^{-1}$)

Statistical analyses were as follows: All values are expressed as mean±SEM and P values <0.05 were considered statistically significant. Student's unpaired t-test was initially used to test for weight and glucose differences between the diabetic and control groups. For comparison of responses during drug exposure, statistical analyses were performed using analysis of variance (Statistica for Windows v.6.1, SAS Institute Inc., California, USA). Subsequent statistical analysis was performed using a mixed model repeated measures ANOVA design.

Statistical analysis using a mixed linear model: Data for each dose level were analyzed using a mixed linear model (PROC MIXED; SAS, Version 8). The model included diabetes, drug and their interaction as fixed effects, time as a repeated measure, and rats as the subjects in the dataset. Complete independence is assumed across subjects. The full model was fitted to each dataset using a maximum likelihood estimation method (REML) fits mixed linear models (i.e., fixed and random effects models). A mixed model is a generalization of the standard linear model, the generalization being that you can analyse data generated from several sources of variation instead of just one. A level of significance of 0.05 was used for all tests. The results were as follows.

Effects of STZ on blood glucose and body weight (Table 1): Blood glucose increased to 25±2 mmol·l$^{-1}$ three days following STZ injection. Despite a greater daily food intake, diabetic animals lost weight whilst nondiabetic animals continued to gain weight during the 44 days following STZ/saline injection. On the day of the experiment blood glucose levels were 24±1 and 5±0 mmol·l$^{-1}$ and body weight 264±7 g and 434±9 g for diabetic and nondiabetic animals respectively.

TABLE 1

Blood glucose, body weight and food consumption in diabetic versus nondiabetic animals

|  | I. DIABETIC | II. NONDIABETIC |
|---|---|---|
| Body weight prior to STZ/saline | 303 ± 3 g | 303 ± 3 g |
| Blood glucose 3 days following STZ/saline | *25 ± 2 mmol · l$^{-1}$ | 5 ± 0.2 mmol · l$^{-1}$ |
| Daily food consumption | *58 ± 1 g | 28 ± 1 g |
| Blood glucose on experimental day | *24 ± 1 mmol · l$^{-1}$ | 5 ± 0.2 mmol · l$^{-1}$ |
| Body weight on experimental day | *264 ± 7 g | 434 ± 9 g |

Diabetic animals n = 14, nondiabetic animals n = 14. Values shown as mean ± SEM. Asterisk indicates a significant difference (P < 0.05).

Cardiovascular variables during infusion: Baseline levels of MAP during the control period prior to infusion were not significantly different between nondiabetic and diabetic animals (99±4 mm Hg). HR was significantly lower in diabetic than nondiabetic animals (287±11 and 364±9 bpm respectively, P<0.001). Infusion of trientine or saline had no effect on these variables except at the highest dose where MAP decreased by a maximum of 19±4 mm Hg for the 2 min following administration and returned to pre-dose levels within 10 min. Body temperature and oxygen saturation remained stable in all animals throughout the experiment.

Figure 16:
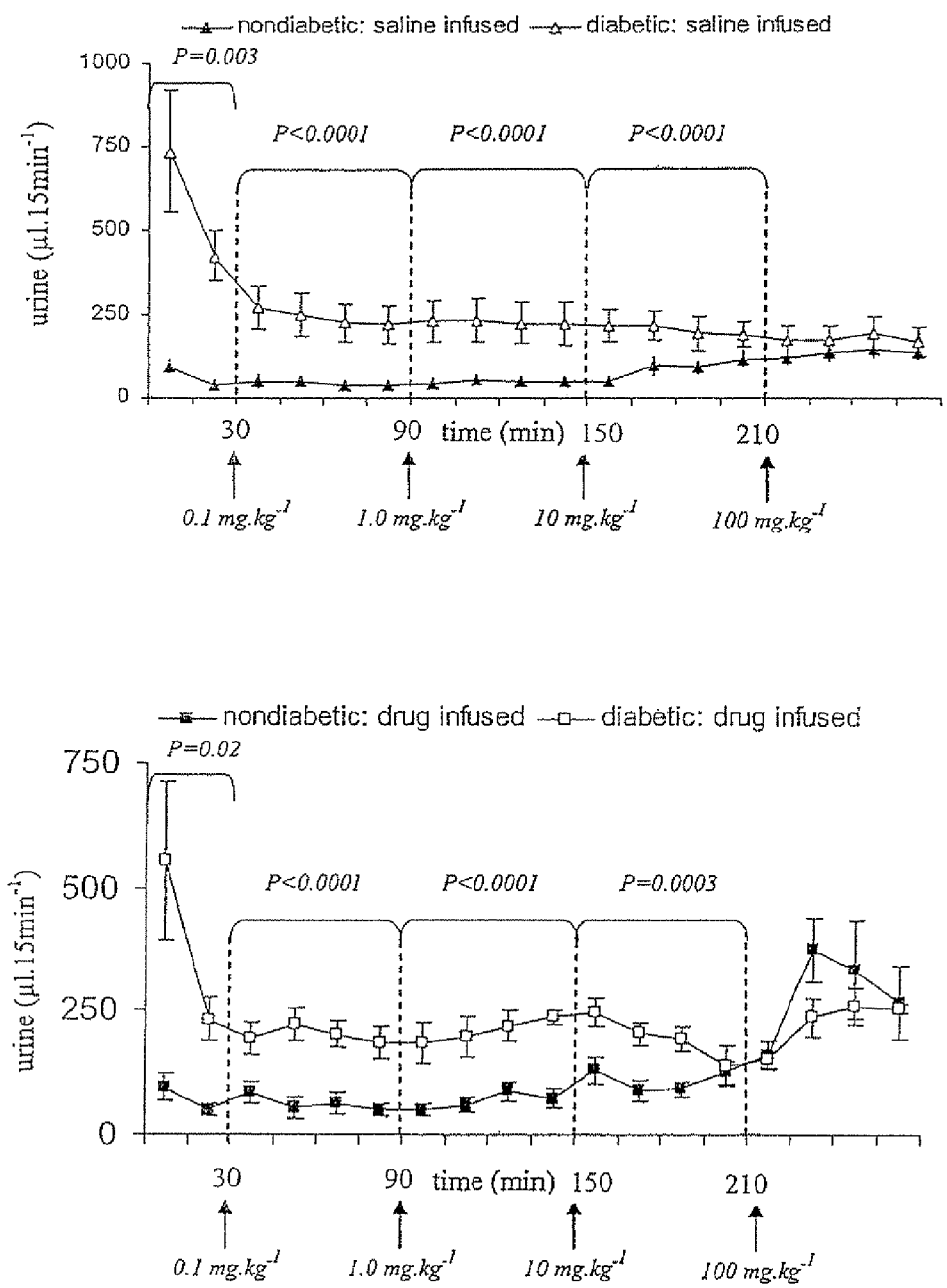
FIG. 16 shows the urine excretion in diabetic and non diabetic animals in response to increasing doses of trientine or equivalent volume of saline, wherein urine excretion in diabetic and nondiabetic animals in response to increasing doses of trientine (bottom; 0.1, 1.0, 10, 100 mg·kg$^{-1}$ in 75 µl saline followed by 125 µl saline flush injected at time shown by arrow) or an equivalent volume of saline (top), and each point represents a 15 min urine collection period (see Methods for details); error bars show SEM and P values are stated if significant ($P<0.05$).
Figure 17:
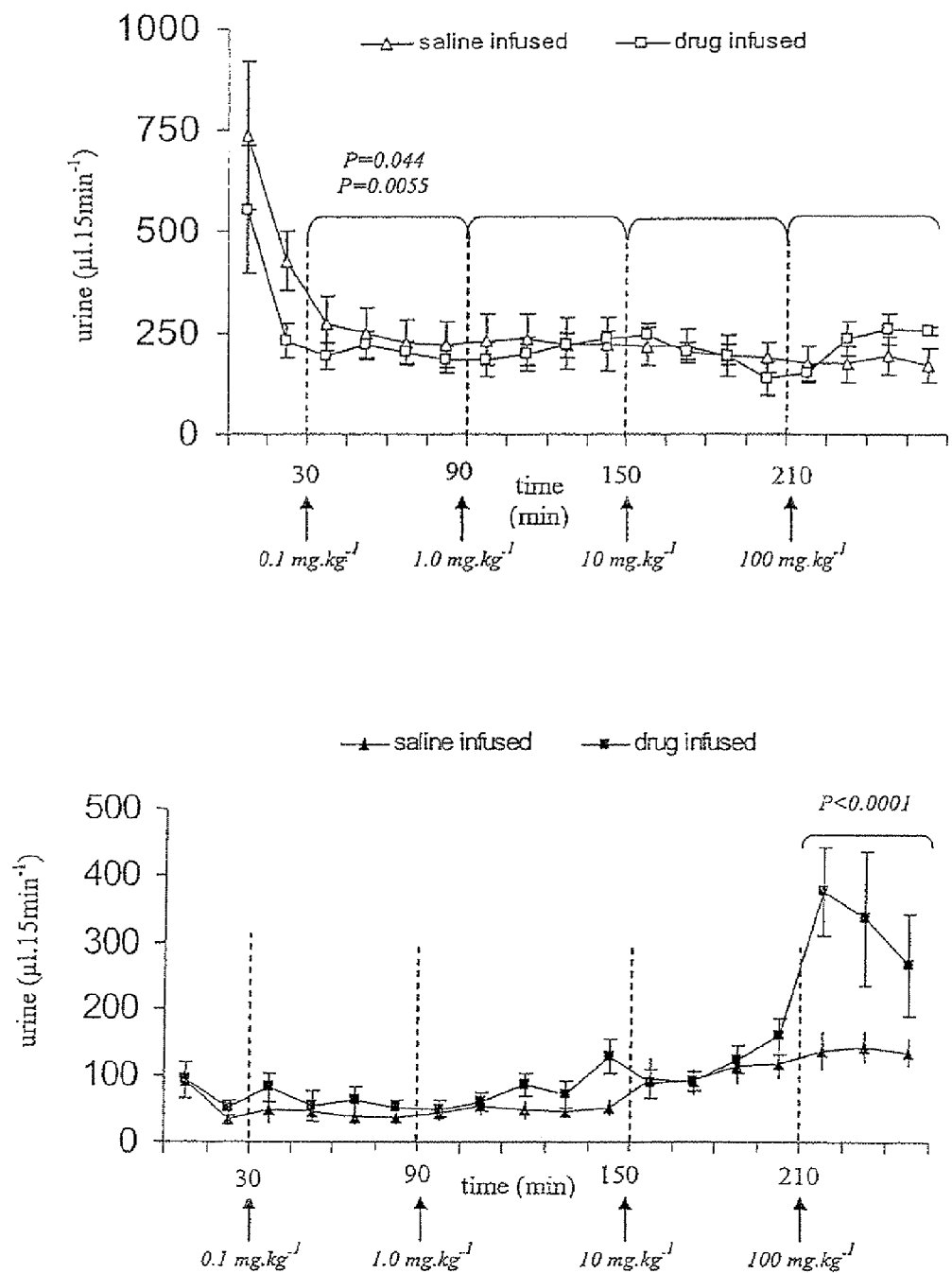
FIG. 17 shows urine excretion in non diabetic and diabetic animals receiving increasing doses of trientine or an equivalent volume of saline, wherein urine excretion in diabetic (top) and nondiabetic (bottom) rats receiving increasing doses of trientine (0.1, 1.0, 10, 100 mg·kg$^{-1}$ in 75 µl saline followed by 125 µl saline flush injected at time shown by arrow) or an equivalent volume of saline, and each point represents a 15 ruin urine collection period (see Methods for details); error bars show SEM and P values are stated if significant ($P<0.05$).

Urine excretion: Diabetic animals consistently excreted significantly more urine than nondiabetic animals except in response to the highest dose of drug (100 mg·kg$^{-1}$) or equivalent volume of saline (FIG. 16). Administration of the 100 mg·kg$^{-1}$ dose of trientine also increased urine excretion in nondiabetic animals to greater than that of nondiabetic animals receiving the equivalent volume of saline (FIG. 17). This effect was not seen in diabetic animals.

Figure 18:
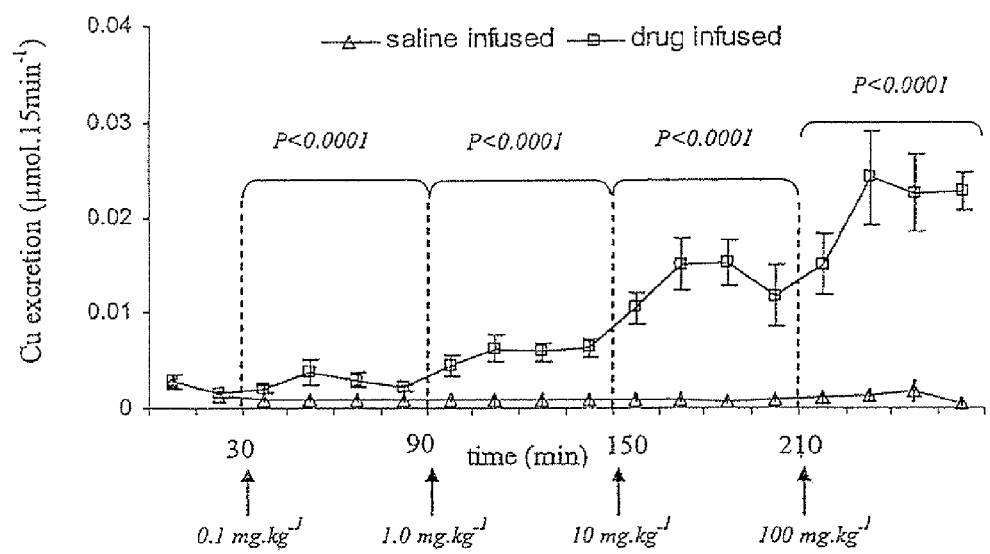
FIG. 18 shows copper excretion in the urine of diabetic and non diabetic animals receiving increasing doses of trientine or an equivalent volume of saline, wherein copper excretion in urine of diabetic (top) and nondiabetic (bottom) rats receiving increasing doses of trientine (0.1, 1.0, 10, 100 mg·kg$^{-1}$ in 75 µl saline followed by 125 µl saline flush injected at time shown by arrow) or an equivalent volume of saline, and each point represents a 15 min urine collection period (see Methods for details); error bars show SEM and P values are stated if significant ($P<0.05$).
Figure 18:
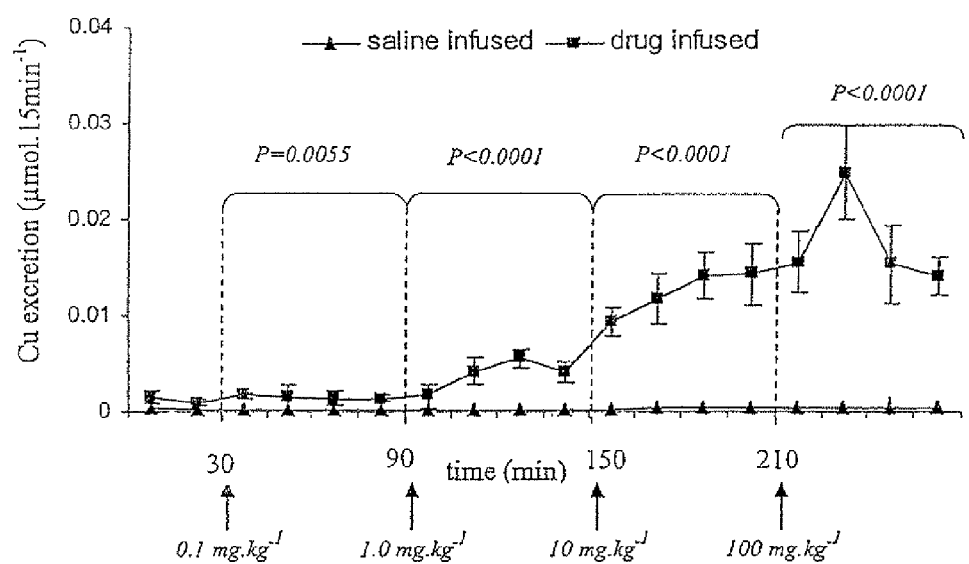
Figure 19:
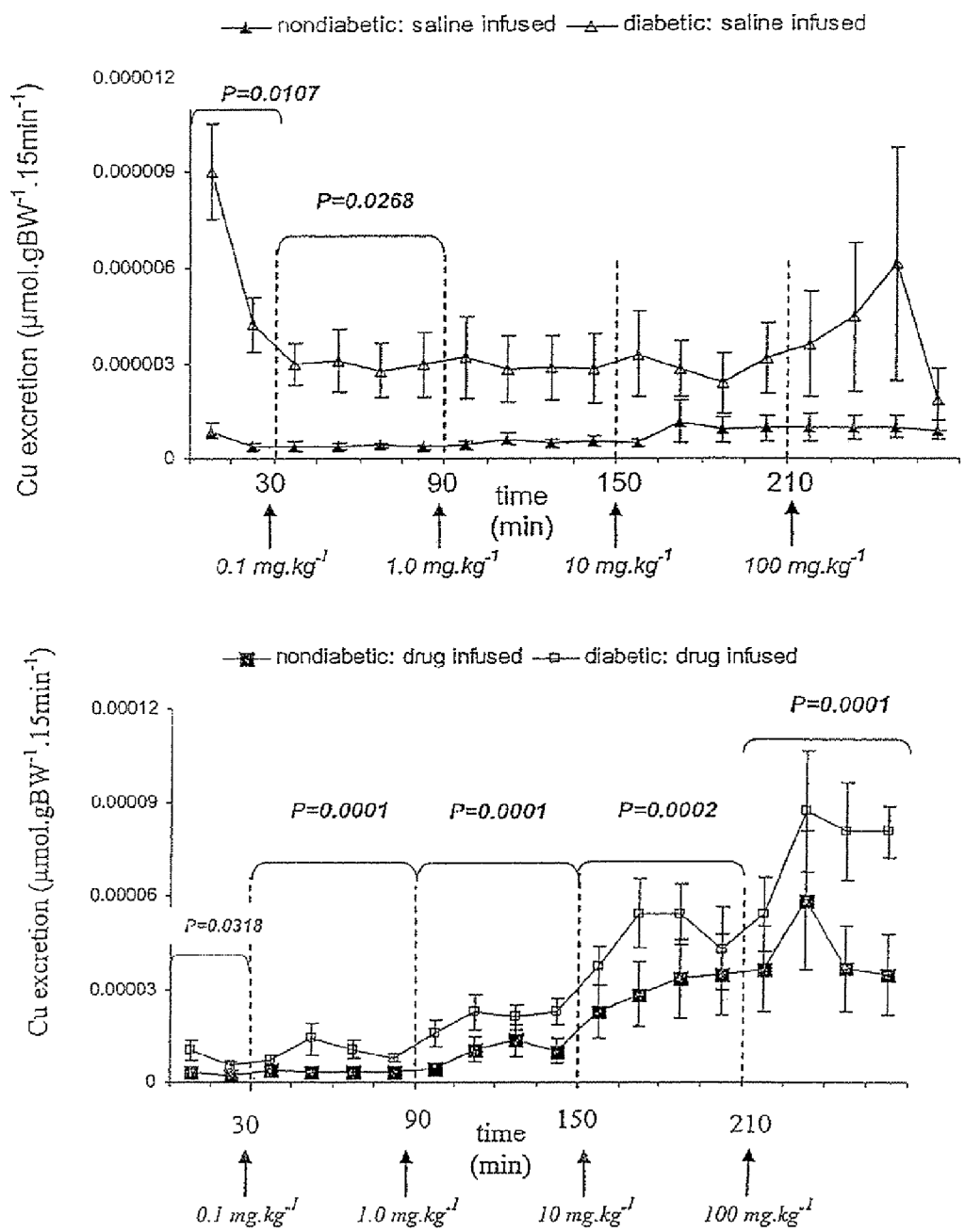
FIG. 19 shows the same information in FIG. 18 with presentation of urinary copper excretion per gram of body-weight, wherein urinary copper excretion per gram of body-weight in diabetic and nondiabetic animals in response to increasing doses of trientine (bottom; 0.1, 1.0, 10, 100 mg·kg$^{-1}$ in 75 μl saline followed by 125 μl saline flush injected at time shown by arrow) or an equivalent volume of saline (top), and each point represents a 15 min urine collection period (see Methods for details); error bars show SEM and P values are stated if significant (P<0.05).
Figure 20:
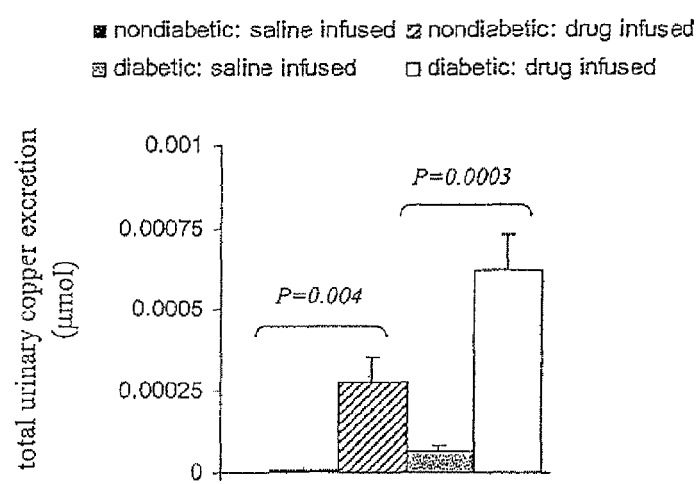
FIG. 20 shows the total amount of copper excreted in non diabetic and diabetic animals administered saline or drug, wherein total urinary copper excretion (mmol) in nondiabetic animals administered saline (black bar, n=7) or trientine (hatched bar, n=7) and in diabetic animals administered saline (grey bar, n=7) or trientine (white bar, n=7); error bars show SEM and P values are stated if significant (P<0.05).
Figure 21:
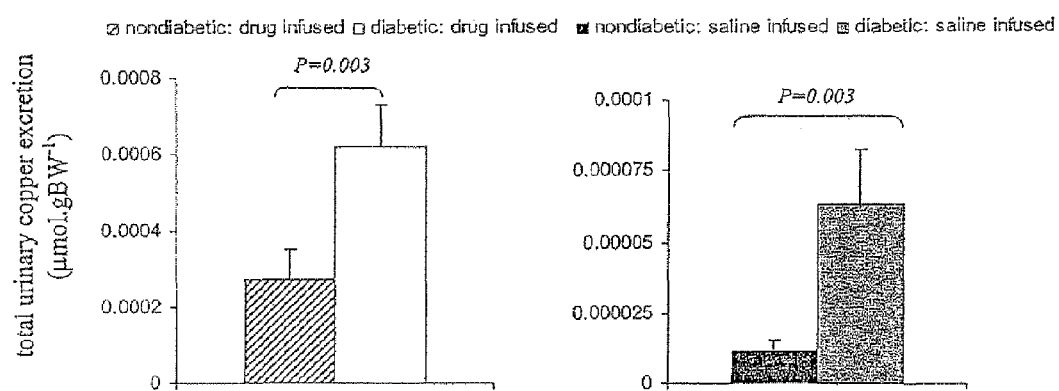
FIG. 21 shows the total amount of copper excreted per gram of bodyweight in animals receiving trientine or saline, wherein total urinary copper excretion per gram of bodyweight (μg·gBW$^{-1}$) in animals receiving trientine (nondiabetic: hatched bar, n=7; diabetic: white bar, n=7) or saline (nondiabetic: black bar, n=7; diabetic: grey bar, n=7); error bars show SEM and P values are stated if significant (P<0.05).

Urinary excretion of Cu and Fe: Analysis of the dose response curves shows that, at all doses, diabetic and nondiabetic animals receiving drug excreted more Cu than animals receiving an equivalent volume of saline (FIG. 18). To provide some correction for the effects of lesser total body growth of the diabetic animals, and thus to allow more appropriate comparison between diabetic and nondiabetic animals, excretion rates of trace elements were also calculated per gram of body weight. FIG. 19 shows that diabetic animals had significantly greater copper excretion per gram of body weight in response to each dose of drug than did nondiabetic animals. The same pattern was seen in response to saline, however the effect was not always significant. Total copper excreted over the entire duration of the experiment was significantly increased in both nondiabetic and diabetic animals administered trientine compared with their respective saline controls (FIG. 20). Diabetic animals receiving drug also excreted more total copper per gram of body weight than nondiabetic animals receiving drug. The same significant trend was seen in response to saline administration (FIG. 21).

Figure 22:
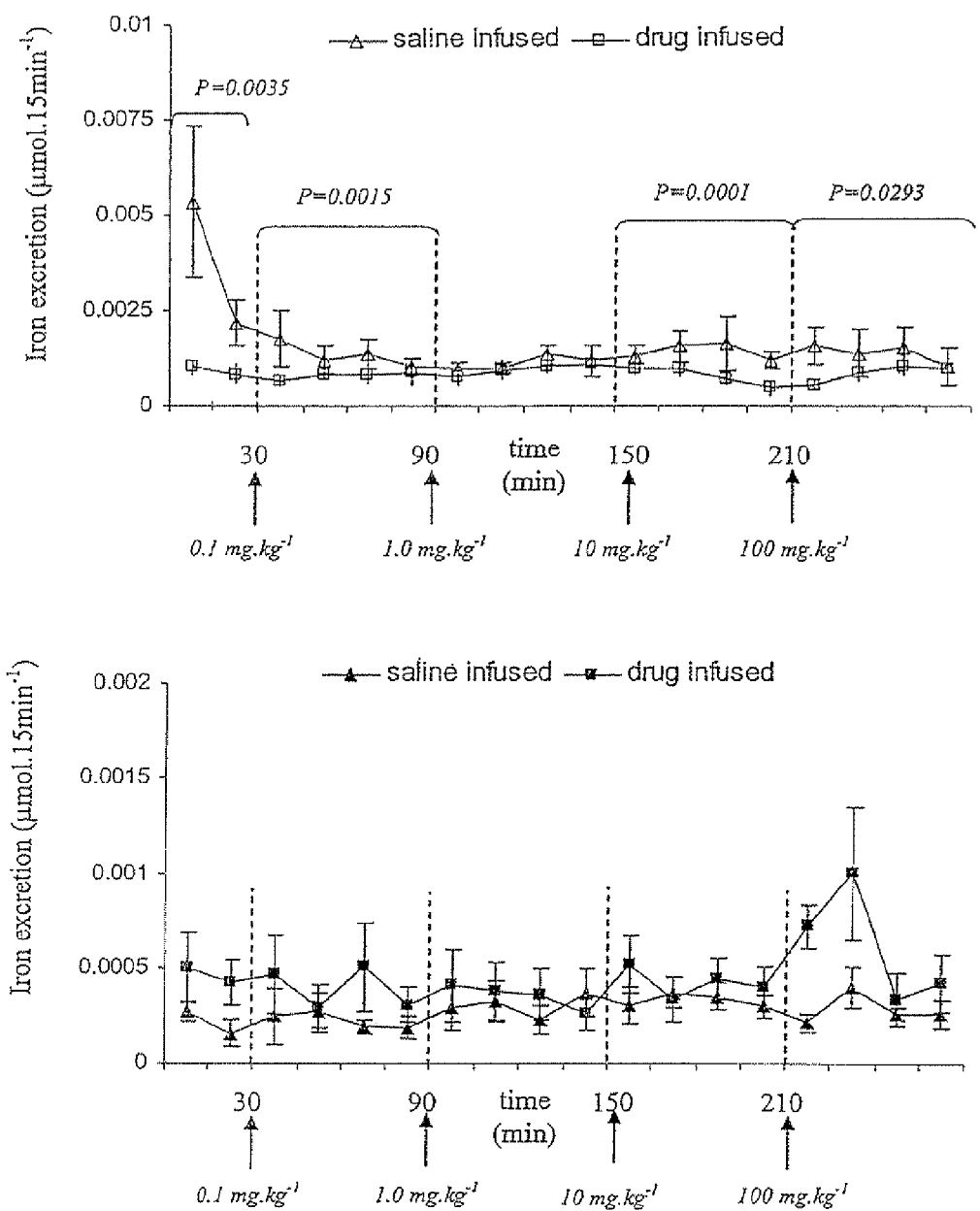
FIG. 22 shows the iron excretion in urine of diabetic and non diabetic animals receiving increasing doses of trientine or an equivalent volume of saline, wherein iron excretion in urine of diabetic (top) and nondiabetic (bottom) rats receiving increasing doses of trientine (0.1, 1.0, 10, 100 mg·kg$^{-1}$ in 75 μl saline followed by 125 μl saline flush injected at time shown by arrow) or an equivalent volume of saline, and each point represents a 15 min urine collection period (see Methods for details); error bars show SEM and P values are stated if significant (P<0.05).
Figure 23:
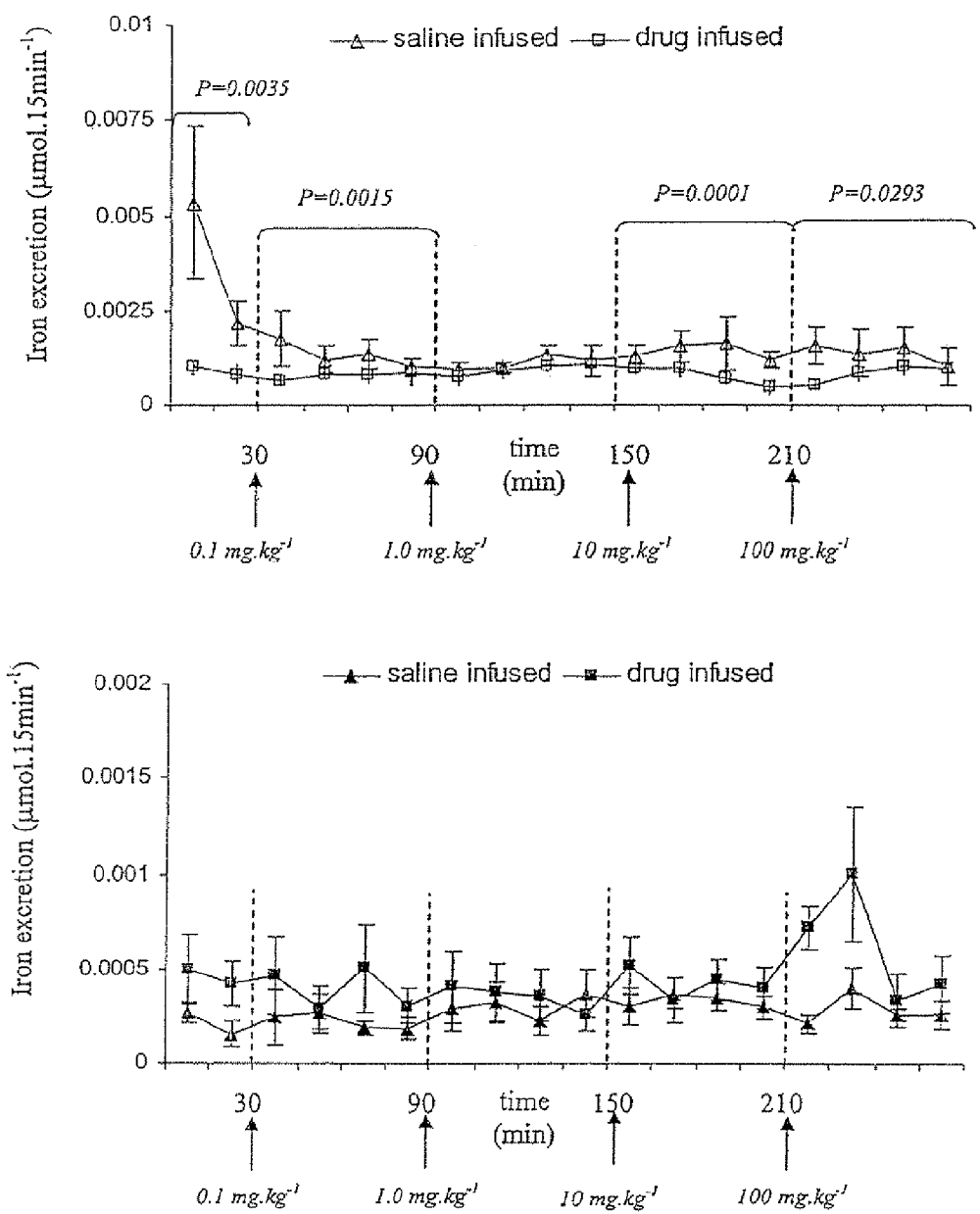
FIG. 23 shows the urinary iron excretion per gram of bodyweight in diabetic and non diabetic animals receiving trientine or saline, wherein urinary iron excretion per gram of bodyweight in diabetic and nondiabetic animals in response to increasing doses of trientine (bottom; 0.1, 1.0, 10, 100 mg·kg$^{-1}$ in 75 μl saline followed by 125 μl saline flush injected at time shown by arrow) or an equivalent volume of saline (top), and each point represents a 15 min urine collection period (see Methods for details); error bars show SEM and P values are stated if significant (P<0.05).
Figure 24:
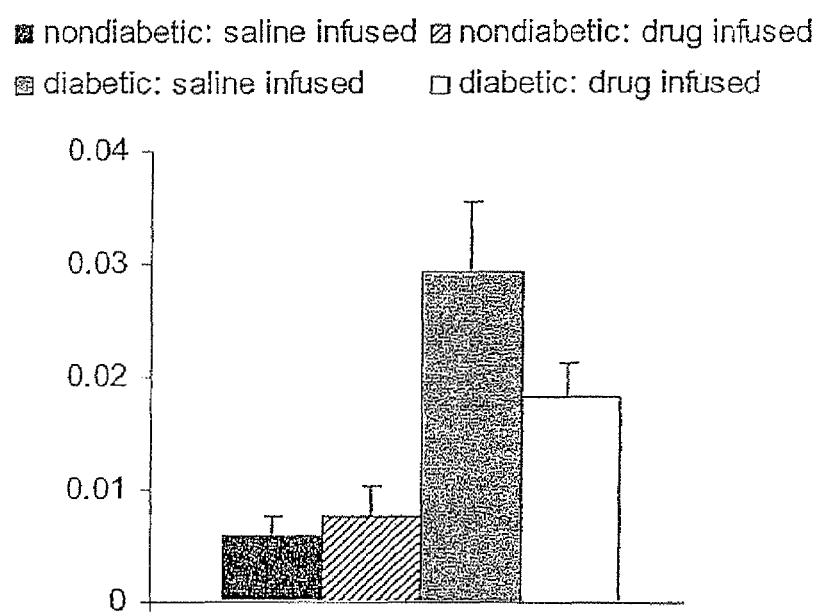
FIG. 24 shows the total urinary iron excretion in non diabetic and diabetic animals administered saline or drug, wherein total urinary iron excretion (μmol) in nondiabetic animals administered saline (black bar, n=7) or trientine (hatched bar, n=7) and in diabetic animals administered saline (grey bar, n=7) or trientine (white bar, n=7); error bars show SEM and P values are stated if significant (P<0.05).
Figure 25:
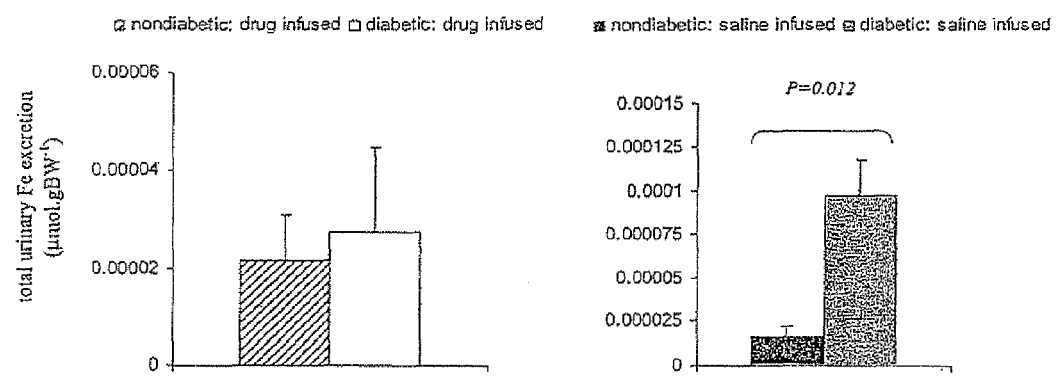
FIG. 25 shows the total urinary iron excretion per gram of bodyweight in animals receiving trientine or saline, wherein Total urinary iron excretion per gram of bodyweight (μg·gBW$^{-1}$) in animals receiving trientine (nondiabetic: hatched bar, n=7; diabetic: white bar, n=7) or saline (nondiabetic: black bar, n=7; diabetic: grey bar, n=7); error bars show SEM and P values are stated if significant (P≤0.05).
Figure 26:
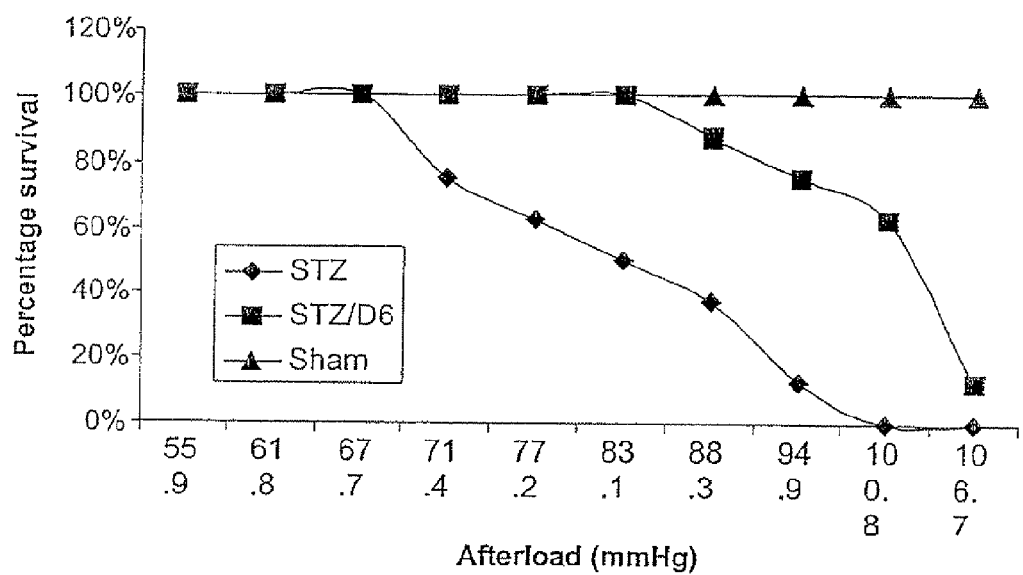
FIG. 26 shows the percentage of surviving hearts at each after-load pressure.

In comparison, iron excretion in both diabetic and nondiabetic animals receiving trientine was not greater than animals receiving an equivalent volume of saline (FIG. 22). Analysis per gram of body weight shows diabetic animals receiving saline excrete significantly more iron than nondiabetic animals, however this trend was not evident between diabetic and nondiabetic animals receiving trientine (FIG. 23). Total iron excretion in both diabetic and nondiabetic animals receiving drug was not different from animals receiving saline (FIG. 24). In agreement with analysis of dose response curves, total iron excretion per gram of body weight was significantly greater in diabetic animals receiving saline than nondiabetic animals but this difference was not seen in response to trientine (FIG. 25).

Serum content and renal clearance of Cu and Fe (Table 2): While there was no significant difference in serum copper content, there was a significant increase in renal clearance of copper in diabetic animals receiving drug compared with diabetic animals receiving saline. The same pattern was seen in nondiabetic animals, although the trend was not statistically significant (P=0.056). There was no effect of drug or state (diabetic versus nondiabetic) on serum content or renal clearance of iron.

TABLE 2

Serum content and renal clearance of Cu and Fe in diabetic and nondiabetic animals receiving drug or saline.

|  | 1.1.a.a.1 diabetic trientine n = 6 | 1.1.a.a.1 diabetic Saline n = 7 | 1.1.a.a.2 nondiabetic trientine n = 4 | 1.1.a.a.2 nondiabetic Saline n = 7 |
|---|---|---|---|---|
| Serum Cu (µg · µl$^{-1}$ × 10$^{-4}$) | 7.56 ± 0.06 | 9.07 ± 1.74 | 7.11 ± 0.41 | 7.56 ± 0.62 |
| Serum Fe (µg · µl$^{-1}$ × 10$^{-4}$) | 35.7 ± 7.98 | 63.2 ± 16.4 | 33.6 ± 1.62 | 31.4 ± 8.17 |
| Renal clearance Cu (µl · min$^{-1}$) | *28.5 ± 4.8 | 1.66 ± 0.82 | 19.9 ± 6.4 | 0.58 ± 0.28 |
| Renal clearance Fe (µl · min$^{-1}$) | 0.25 ± 0.07 | 0.38 ± 0.15 | 0.46 ± 0.22 | 0.11 ± 0.03 |

Values shown as mean ± SEM. Asterick indicates a significant difference (P < 0.05) between diabetic animals receiving trientine and diabetic animals receiving an equivalent volume of saline.

Metal content of cardiac tissue (Table 3): Wet heart weights in diabetic animals were significantly less than those in non-diabetic animals while heart/body weight ratios were increased. In some animals cardiac tissue was also analyzed for Cu and Fe content. There was no significant difference in content of copper between diabetic and nondiabetic animals receiving saline or trientine. Iron content of the non-diabetic animals administered saline was significantly greater than that of the diabetic animals administered saline.

TABLE 3

Heart weight, heart weight/body weight ratios and trace metal content of heart tissue in diabetic versus nondiabetic animals.

|  | DIABETIC | NONDIABETIC |
|---|---|---|
| Wet heart weight | *0.78 ± 0.02 g | 1.00 ± 0.02 g |
| Heart weight/body weight | *2.93 ± 0.05 mg · g$^{-1}$ | 2.30 ± 0.03 mg · g$^{-1}$ |
| Cu content µg · g$^{-1}$ dry tissue |  |  |
| Trientine treated | 24.7 ± 1.5 | 27.1 ± 1.0 |
| Saline treated | 21.3 ± 0.9 | 27.2 ± 0.7 |
| Fe content µg · g$^{-1}$ dry tissue |  |  |
| Trientine treated | 186 ± 46 | 235 ± 39 |
| Saline treated | †180 ± 35 | 274 ± 30 |

Diabetic animals: n = 5; nondiabetic animals: n = 10. Values shown as mean ± SEM. Asterisk indicates a significant difference (P < 0.05) between diabetic and nondiabetic animals.
†indicates a significant difference (P < 0.05) between diabetic and non-diabetic animals receiving saline.

Results from application of a mixed linear model to the experimental analysis (FIG. 35).

Copper: Diabetic rats excreted significantly higher levels of copper across all dose levels. Baseline copper excretion was also significantly higher in diabetic rats compared to and prior to drug administration. The drug resulted in a significantly higher excretion of copper compared to saline at all dose levels. There was no difference at baseline levels between the drug and saline groups. The interaction effect for the model was significant at dose levels of 1.0 mg·kg$^{-1}$ and above. The presence of a significant interaction term means that the influence of one effect varies with the level of the other effect. Therefore, the outcome of a significant interaction between the diabetes and drug factors is increased copper excretion above the predicted additive effects of these two factors.

Iron: Diabetic rats in the saline only group excreted significantly higher levels of iron at all dose levels. This resulted in all factors in the model being significant across all dose levels.

In sum, the acute effect of intravenous trientine administration on the cardiovascular system and urinary excretion of copper and iron was studied in anesthetized, diabetic (6 weeks of diabetes, Streptozotocin induced) and nondiabetic rats. Animals were assigned to one of four groups: diabetic+ trientine, diabetic+saline, nondiabetic+trientine, nondiabetic+saline, Drug, or an equivalent volume of saline, was administered hourly in doses of increasing strength (0.1, 1.0, 10, 100 mg·kg$^{-1}$) and urine was collected throughout the experiment in 15 min aliquots. A terminal blood sample was taken and cardiac tissue harvested. Analysis of urine samples showed the following main points:

- At all drug doses, diabetic and nondiabetic animals receiving drug excreted more Cu (μg) than animals receiving an equivalent volume of saline.
- When analyzed per gram of bodyweight, diabetic animals excreted significantly more copper (μg·gBW$^{-1}$) at each dose of trientine than did nondiabetic animals. The same pattern was seen in response to saline but the effect was not significant at every dose.
- At most doses, in diabetic animals iron excretion (μg) was greater in animals administered saline than in those administered drug. In nondiabetic animals there was no difference between iron excretion in response to saline or trientine administration.
- Analysis per gram of body weight shows no difference between iron excretion in nondiabetic and diabetic animals receiving trientine. Diabetic animals receiving saline excrete more iron per gram of bodyweight than nondiabetic animals receiving saline.
- Analysis of heart tissue showed no significant difference in total copper content between diabetic and nondiabetic animals, nor any effect of drug on cardiac content of iron and copper.
- Renal clearance calculations showed a significant increase in clearance of copper in diabetic animals receiving trientine compared with diabetic animals receiving saline. The same trend was seen in nondiabetic animals but the affect was not significant. There was no affect of trientine on renal clearance of iron.

Thus, there were no adverse cardiovascular effects were observed after acute administration of trientine. Trientine treatment effectively increases copper excretion in both diabetic and nondiabetic animals. The excretion of copper in urine following trientine administration is greater per gram of bodyweight in diabetic than in nondiabetic animals. Iron excretion was not increased by trientine treatment in either diabetic or nondiabetic animals.

Experiments relating to the efficacy of trientine to restore cardiac function in STZ diabetic rats were also carried out. As noted above, histological evidence from earlier studies showed that treatment with trientine appears to protect the hearts of diabetic Wistar rats from development of cardiac damage (diabetic cardiomyopathy), as judged by histology. However, it was unknown whether this histological improvement translates into an improvement in cardiac function. One aim of this study was to use an isolated-working-rodent heart model to compare cardiac function in trientine-treated and non-treated, STZ diabetic and normal rats.

Male albino Wistar rats weighing 330-430 g were assigned to four experimental groups as follows:

| Experimental groups | | | |
|---|---|---|---|
| Group | Code | N | Treatment |
| Group A | STZ | 8 | Diabetes for 13 weeks |
| Group B | STZ/D6 | 8 | Diabetes for 13 weeks (Drug therapy week 7-13) |
| Group C | Sham | 9 | Non-diabetic controls |
| Group D | Sham/D7 | 11 | Non-diabetic controls (Drug therapy week 7-13) |

STZ = Streptozotocin; D7 = trientine treatment for 7 consecutive weeks commencing 6 weeks after the start of the experiment.

Diabetes was induced by intravenous streptozotocin (STZ; Sigma; St. Louis, Mo.). All rats were given a short inhalational anaesthetic (Induction: 5% halothane and 2 L/min oxygen, maintained on 2% halothane and 2 L/min oxygen). Those in the two diabetic groups then received a single intravenous bolus dose of STZ (57 mg/kg body weight) in 0.5 ml of 0.9% saline administered via a tail vein. Non-diabetic sham-treated animals received an equivalent volume of 0.9% saline. Diabetic and non-diabetic rats were housed in like-pairs and provided with free access to normal rat chow (Diet 86 pellets; New Zealand Stock Feeds, Auckland, NZ) and deionized water ad libitum. Each cage had two water bottles on it to ensure equal access to water or drug for each animal. Animals were housed at 21 degrees and 60% humidity in standard rat cages with a sawdust floor that was changed daily.

Blood glucose was measured in tail-tip capillary blood samples (Advantage II, Roche Diagnostics, NZ Ltd). Sampling was performed on all groups at the same time of the day. Blood glucose and body weight were measured on day 3 following STZ/saline injection and then weekly throughout the study. Diabetes was confirmed by presence of polydipsia, polyuria and hyperglycemia (>11 mmol·L$^{-1}$).

In the drug treated diabetic group, trientine was prepared in the drinking water for each cage at a concentration of 50 mg/L. Each animal consumed about 260 ml water per day once diabetes was established, to yield a total drug dose per animal per day of ~13 mg/kg. The trientine-containing drinking water was administered continuously from the start of week 7 until the animal was sacrificed at the end of week 13. In the case of the Sham/D7 non-diabetic group that drank less water per day than diabetic animals, the drug concentration in their drinking water was adjusted each week so that they consumed approximately the same dose as the corresponding STZ/D7 group. At the time the drug started in the diabetic group the diabetic animals were expected to have to have established cardiomyopathy, as shown by preliminary studies (data not shown) and confirmed in the literature. See Rodrigues B, et al., *Diabetes* 37(10):1358-64 (1988).

On the last day of the experiment, animals were anesthetized (5% halothane and 2 L·min$^{-1}$ O$_2$), and heparin (500 IU·kg$^{-1}$) (Weddel Pharmaceutical Ltd., London) administered intravenously via tail vein. A 2 ml blood sample was then taken from the inferior vena cava and the heart was then rapidly excised and immersed in ice-cold Krebs-Henseleit bicarbonate buffer to arrest contractile activity. Hearts were then placed in the isolated perfused working heart apparatus.

The aortic root of the heart was immediately ligated to the aortic cannula of the perfusion apparatus. Retrograde (Langendorff) perfusion at a hydrostatic pressure of 100 cm $H_2O$ and at 37° C. was established and continued for 5 min while cannulation of the left atrium via the pulmonary vein was completed. The non-working (Langendorff) preparation was then converted to the working heart model by switching the supply of perfusate buffer from the aorta to the left atrium at a filling pressure of 10 cm $H_2O$. The left ventricle spontaneously ejected into the aortic cannula against a hydrostatic pressure (after-load) of 76 cm$H_2O$ (55.9 mmHg). The perfusion solution was Krebs-Henseleit bicarbonate buffer (mM: KCl 4.7, $CaCl_2$ 2.3, $KH_2PO_4$ 1.2, $MgSO_4$ 1.2, NaCl 118, and $NaHCO_3$ 25), pH 7.4 containing 11 mM glucose and it was continuously gassed with 95% $O_2$:5% $CO_2$. The buffer was also continuously filtered in-line (initial 8 µm, following 0.4 µm cellulose acetate filters; Sartorius, Germany). The temperature of the entire perfusion apparatus was maintained by water jackets and buffer temperature was continuously monitored and adjusted to maintain hearts at 37° C. throughout perfusion.

A modified 24 g plastic intravenous cannula (Becton Dickson, Utah, USA) was inserted into the left ventricle via the apex of the heart using the normal introducer-needle. This cannula was subsequently attached to a SP844 piezo-electric pressure transducer (AD Instruments) to continuously monitor left ventricular pressure. Aortic pressure was continuously monitored through a side arm of the aortic cannula with a pressure transducer (Statham Model P23XL, Gould Inc., CA, USA). The heart was paced (Digitimer Ltd, Herefordshire, England) at a rate of 300 bpm by means of electrodes attached to the aortic and pulmonary vein cannulae using supra-threshold voltages with pulses of 5-ms duration from the square wave generator.

Aortic flow was recorded by an in-line flow meter (Transonic T206, Ithaca, N.Y., USA) and coronary flow was measured by timed 30 sec collection of the coronary vein effluent at each time point step of the protocol.

Figure 14:
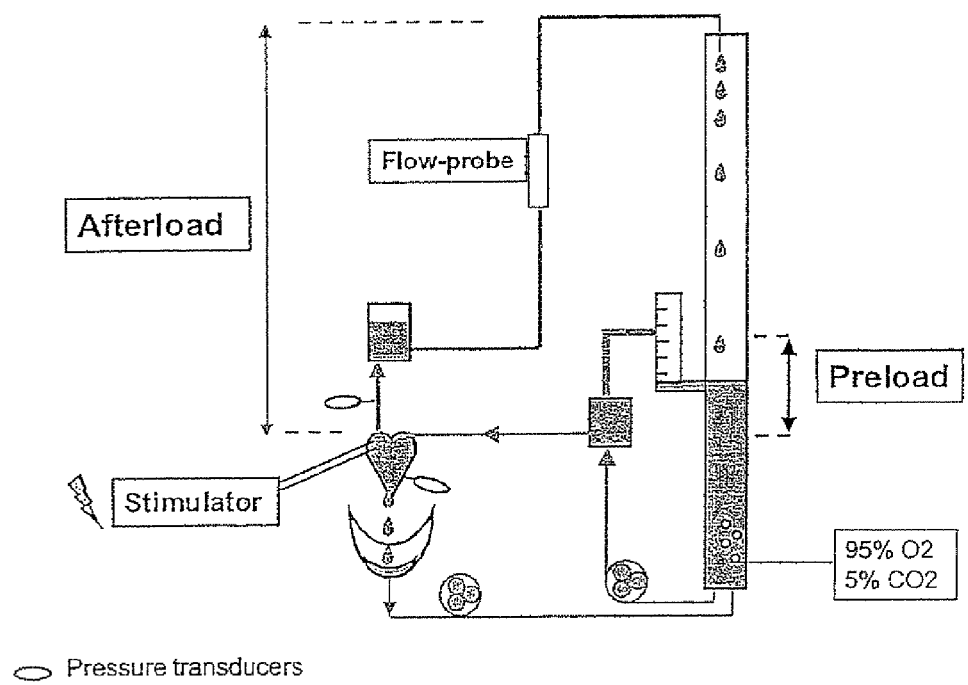
FIG. 14 shows diagrammatically how the extracted heart was attached to the modified apparatus.
Figure 15:
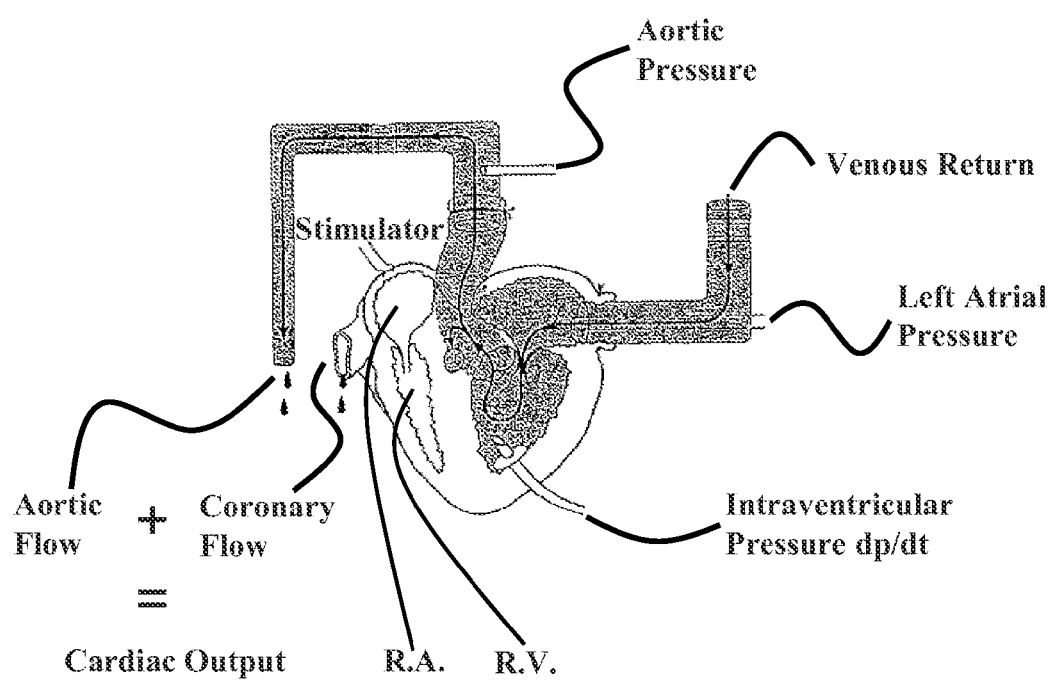
FIG. 15 shows diagrammatically the heart depicted in FIG. 14 in more detail (picture adapted from Grupp I et al., *Am J Physiol* 34:H1401-1410 (1993)).

The working heart apparatus used was a variant of that originally described by Neely, J R, et al., *Am J Physiol* 212: 804-14 (1967). The modified apparatus allowed measurements of cardiac function at different pre-load pressures (FIG. 14 and FIG. 15). This was achieved by constructing the apparatus so that the inflow height of the buffer coming to the heart could be altered through a series of graduated steps in a reproducible manner. As in the case of the pre-load, the outflow tubing from the aorta could also be increased in height to provide a series of defined after-load pressures. The after-load heights have been converted to mm Hg for presentation in the results which is in keeping with published convention.

All data from the pressure transducers and flow probe were collected (Powerlab 16 s data acquisition machine; AD Instruments, Australia). The data processing functions of this device were used to calculate the first derivative of the two pressure waves (ventricular and aortic). The final cardiac function data available comprised:

Cardiac output*; aortic flow; coronary flow; peak left ventricular/aortic pressure developed; maximum rate of ventricular pressure development (+dP/dt); maximum rate of ventricular pressure relaxation (−dP/dt); maximum rate of aortic pressure development (aortic +dP/dt); maximum rate of aortic relaxation (aortic −dP/dt).

[*Cardiac output (CO) is the amount of buffer pumped per unit time by the heart and is comprised of buffer that is pumped out the aorta as well as the buffer pumped into the coronary vessels. This is an overall indicator of cardiac function. **+dP/dt is the rate of change of ventricular (or aortic pressure) and correlates well with the strength of the contraction of the ventricle (contractility). It can be used to compare contractility abilities of different hearts when at the same pre-load (Textbook of Medical Physiology, Ed. A. Guyton. Saunders company 1986). −dP/dt is an accepted measurement of the rate of relaxation of the ventricle].

The experiment was divided into two parts, the first with fixed after-load and variable pre-load the second, which immediately followed on from the first, with fixed pre-load and variable after-load.

Fixed After-load and changing Pre-load: After the initial cannulation was completed, the heart was initially allowed to equilibrate for 6 min at 10 cm $H_2O$ atrial filling pressure and 76 cm $H_2O$ after-load. During this period the left ventricular pressure transducer cannula was inserted and the pacing unit started. Once the heart was stable, the atrial filling pressure was then reduced to 5 cm $H_2O$ of water and then progressively increased in steps of 2.5 cm$H_2O$ over a series of 7 steps to a maximum of 20 cm$H_2O$. The pre-load was kept at each filling pressure for 2 min, during which time the pressure trace could be observed to stabilize and the coronary flow was measured. On completion of the variable pre-load experiment, the variable after-load portion of the experiment was immediately commenced.

Fixed Pre-load and changing After-load: During this part of the experiment the filling pressure (pre-load) was set at 10 cm $H_2O$ and the after-load was then increased from 76 cm $H_2O$ (55.9 mm Hg) in steps of 8 cm $H_2O$ (5.88 mmHg); again each step was of 2 min duration. The maximum height (after-load) to which each individual heart was ultimately exposed, was determined either by attainment of the maximal available after-load height of 145 cm $H_2O$ (106.66 mm Hg), or the height at which measured aortic flow became 0 ml/min. In the later situation, the heart was considered to have "functionally failed." To ensure that this failure was indeed functional and not due to other causes (e.g., permanent ischaemic or valvular damage) all hearts were then returned to the initial perfusion conditions (pre-load 10 cm H2O; after-load 75 cm H2O) for 4 minutes to confirm that pump function could be restored. At the end of this period the hearts were arrested with a retrograde infusion of 0.4 ml of cold KCL (24 mM). The atria and vascular remnants were then excised, the heart blotted dry and weighed. The ventricles were incised midway between the apex and atrioventricular sulcus. Measurements of the ventricular wall thickness were then made using a micro-caliper (Absolute Digimatic, Mitutoyo Corp, Japan).

Data from the Powerlab was extracted by averaging 1 min intervals from the stable part of the electronic trace generated from each step in the protocol. The results from each group were then combined and analyzed for differences between the groups for the various cardiac function parameters (aortic flow, cardiac flow, MLVDP, LV or aortic +/−dP/dt). Differences between repeated observations at different pre-load conditions were explored and contrasted between study group using a mixed models approach to repeated measures (SAS v8.1, SAS Institute Inc, Cary N.C.). Missing random data were imputed using a maximum likelihood approach. Significant mean and interaction effects were further examined using the method of Tukey to maintain a pairwise 5% error rate for post hoc tests. All tests were two-tailed. Survival analysis was done using Proc Liftest (SAS V8.2). A one-way analysis of variance was used to test for difference between groups in various weight parameters. Tukey's tests were used to compare each group with each other. In each graph unless otherwise stated. * indicates p<0.05=STZ v STZ/D7, #.p<0.05=STZ/D7 v Sham/D7.

Figure 5:
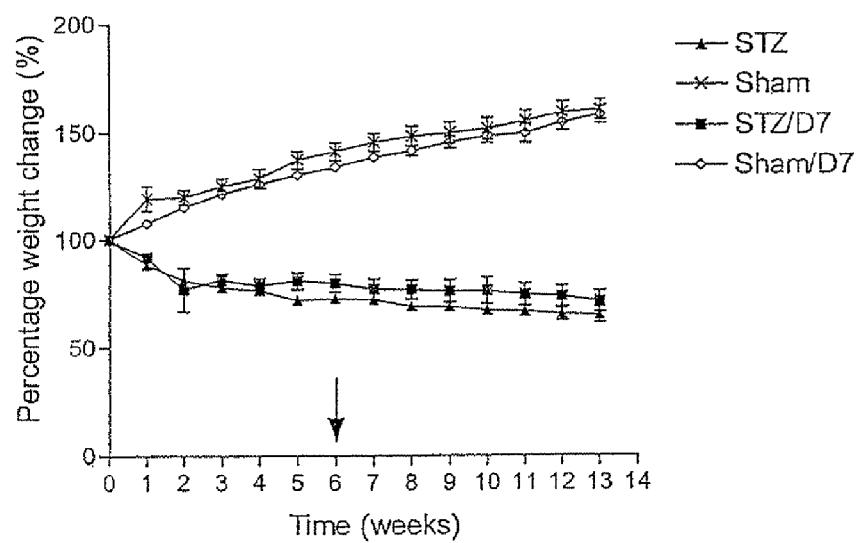
FIG. 5 is a diagram showing the body weight of animals changing over the time period of experiment.

Results showing that the weights of the animals at the end of the experimental period are found in Table 4. Diabetic animals were about 50% smaller than their corresponding age matched normals. A graph of the percentage change in weight for each experimental group is found in FIG. 5, wherein the arrow indicates the start of trientine treatment.

TABLE 4

Initial and final animal body weights (mean ± SD)

| | Number (n) | Treatment | Initial weight (g) | Final weight (g) |
|---|---|---|---|---|
| * Group A | 9 | STZ | 361 ± 12 | 221 ± 27 |
| * Group B | 8 | STZ/D7 | 401 ± 33 | 290 ± 56 |
| * Group C | 8 | Sham | 361 ± 16 | 574 ± 50 |
| Group F | 11 | Sham/D7 | 357 ± 7 | 563 ± 17 |

* P < 0.05

Figure 6:
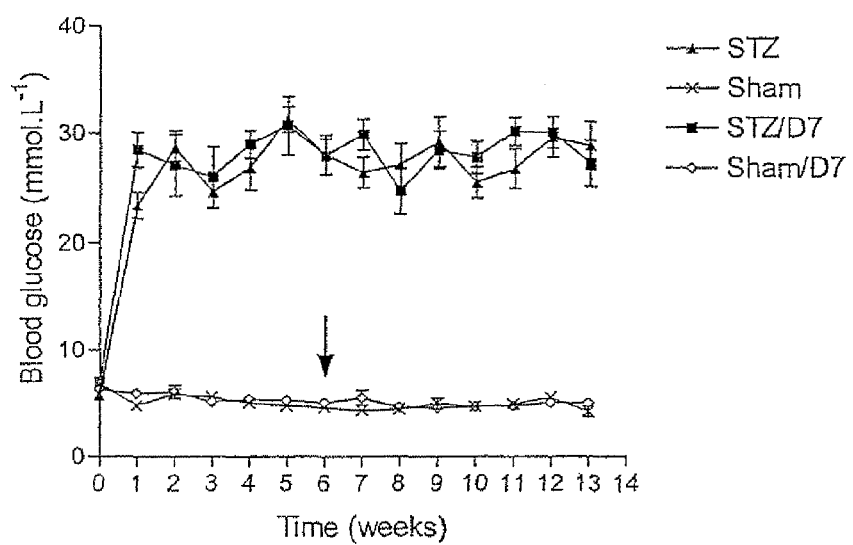
FIG. 6 shows the glucose levels of the animals changing over the time period of the experiment.

Blood glucose values for the three groups of rats are presented in FIG. 6. Generally, the presence of diabetes was established and confirmed within 3-5 days following the STZ injection. The Sham and Sham/D7 control group remained normoglycemic throughout the experiment. Treatment with the drug made no difference to the blood glucose profile (p=ns) in either treated group compared to their respective appropriate untreated comparison group.

Final heart weight and ventricular wall thickness measurements are presented in Table 5. There was a small but significant improvement in the "heart:body weight" ratio with treatment in the diabetic animals. There was a trend toward improved "ventricular wall thickness:bodyweight" ratio in treated diabetics compared to non-treated but this did not reach significance.

diabetic; STZ diabetic+drug; and sham-treated controls) while undergoing increasing atrial filling pressure (5-20 cmH$_2$O, pre-load) with a constant after-load of 75 cm H$_2$O. All results are mean±sem. In each graph for clarity unless otherwise stated, only significant differences related to the STZ/D7 the other groups are shown:* indicates p<0.05 for STZ v STZ/D7, # p<0.05 for STZ/D7 v Sham/D7. Unless stated, STZ/D7 v Sham or Sham/D7 was not significant.

Figure 7:
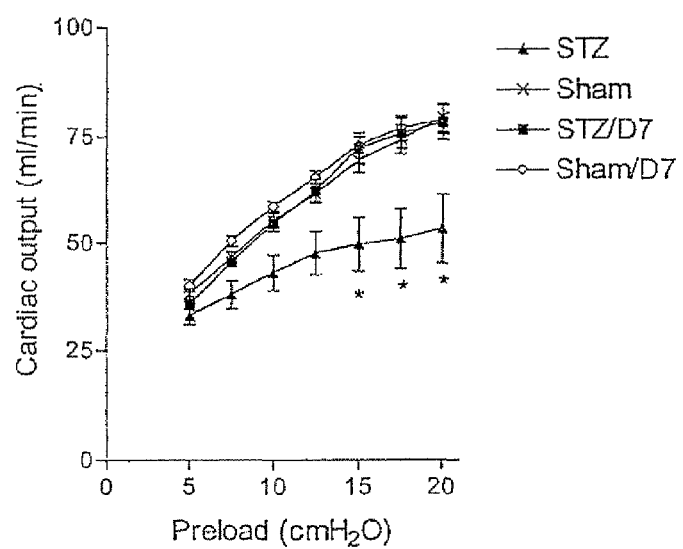
FIG. 7 is a diagram showing cardiac output.
Figure 8:
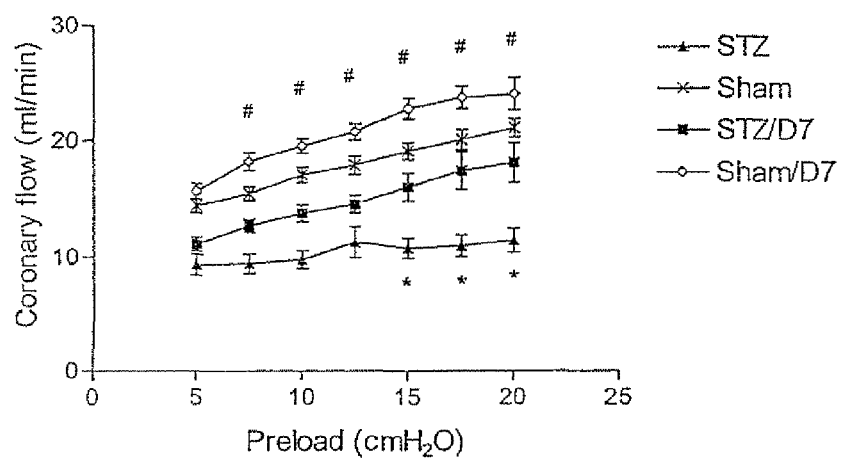
FIG. 8 is a diagram showing coronary flow.
Figure 9:
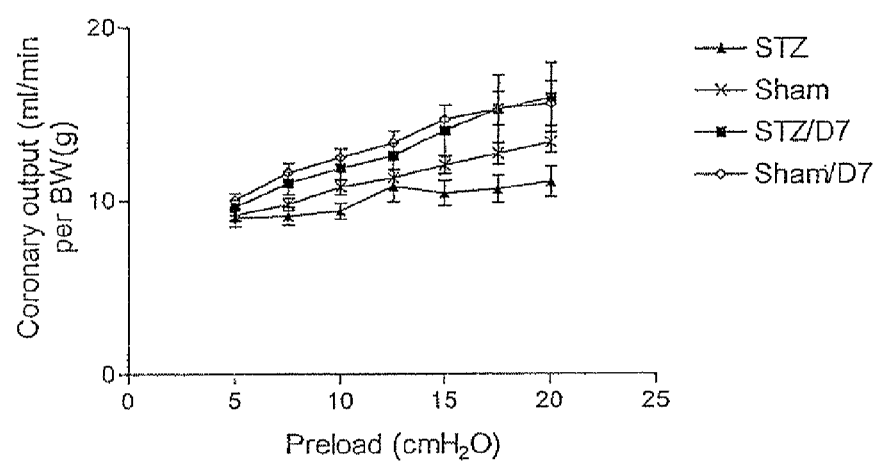
FIG. 9 is a diagram showing coronary flow normalized to final cardiac weight.
Figure 10:
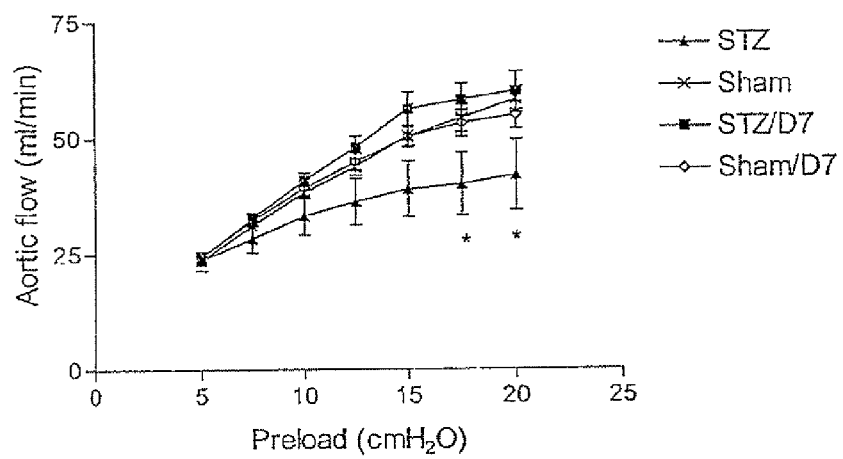
FIG. 10 is a diagram showing aortic flow.

Cardiac output (FIG. 7) is the sum to the aortic flow (FIG. 10) and the coronary flow as displayed in FIG. 8. Since the control hearts and experimental groups have significantly different final weights, the coronary flow is also presented (FIG. 9) as the flow normalized to heart weight (note that coronary flow is generally proportional to cardiac muscle mass, and therefore to cardiac weight)

Figure 11:
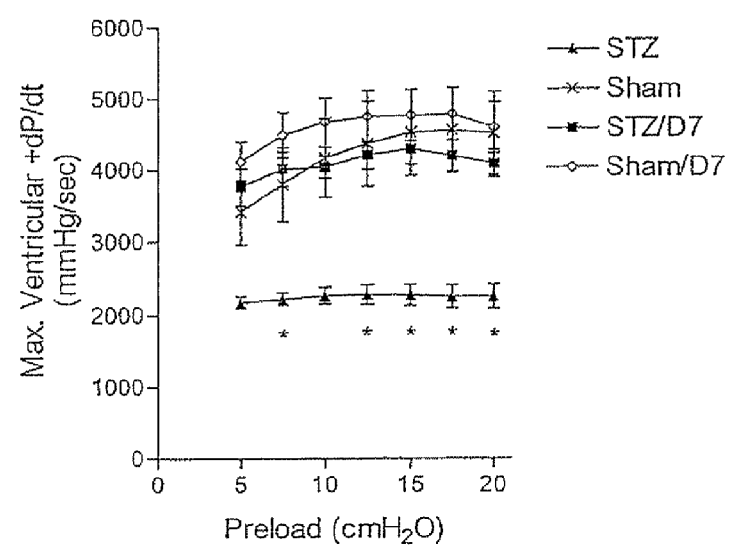
FIG. 11 is a diagram showing the maximum rate of positive change in pressure development in the ventricle with each cardiac cycle (contraction).
Figure 12:
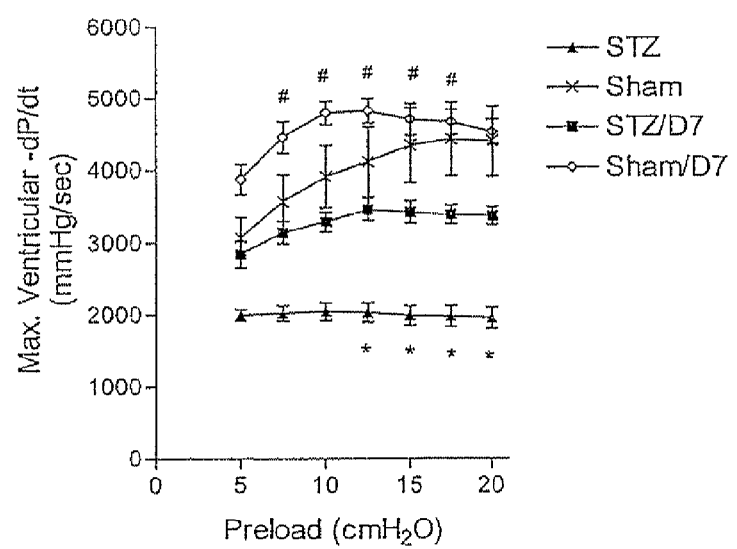
FIG. 12 is a diagram showing the maximum rate of decrease in pressure in the ventricle with each cardiac cycle (relaxation).

The first derivative of the pressure curve gives the rate of change in pressure development in the ventricle with each cardiac cycle and the maximum positive rate of change (+dP/dt) value is plotted in FIG. 11. The corresponding maximum rate of relaxation (−dP/dt) is in FIG. 12. Similar results showing improvement in cardiac function were found from the data derived from the aortic pressure cannula (results not shown).

Figure 13:
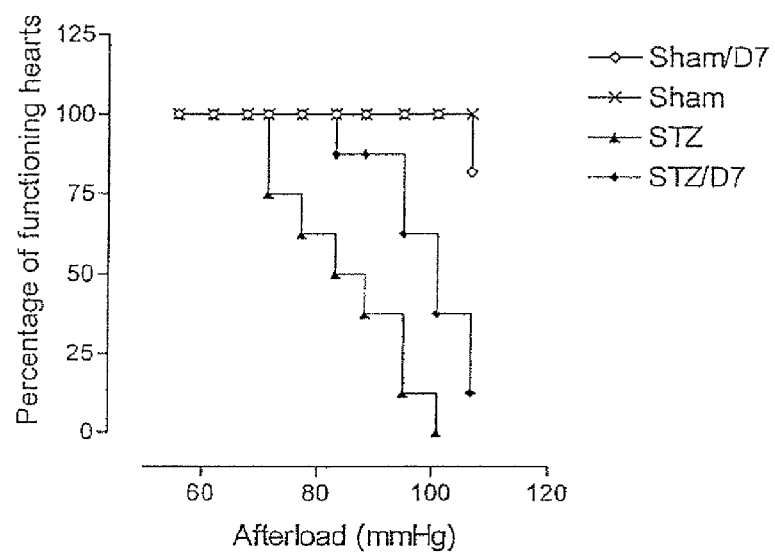
FIG. 13 shows the percentage of functional surviving hearts at each after-load.

Part II Results:

Under conditions for constant pre-load and increasing after-load the ability of the hearts to cope with additional after-load work was assessed. The plot of functional survival, that is the remaining number of hearts at each after-load that still had an aortic output of greater than 0 ml/min is found in FIG. 13 and Table 6.

TABLE 5

Final heart weights (g) and per g of animal body Weight (BW) (mean ± SD)

| Group | Heart weight (g) | Heart weight (g)/BW (g) | Left Ventricular wall thickness (mm) | Left Ventricular wall thickness per BW (mm)/(g) |
|---|---|---|---|---|
| Sham | 1.58 ± 0.13§ | 0.0028 ± 0.0002§ | 3.89 ± 0.38§ | 0.0068 ± 0.0009§ |
| STZ/D7* | 1.18 ± 0.24 | 0.0041 ± 0.0005 | 3.79 ± 0.52 | 0.0127 ± 0.0027 |
| STZ* | 1.03 ± 0.17 | 0.0047 ± 0.0004 | 3.31 ± 0.39 | 0.0152 ± 0.0026 |
| Sham/D7 | 1.58 ± 0.05§ | 0.0028 ± 0.0001§ | 4.03 ± 0.1§ | 0.0072 ± 0.0003§ |

*P < 0.05
§= significant with the STZ and STZ/D7 groups p < 0.05

Part I results: The following graphs of FIGS. 7 to 12 represent cardiac performance parameters of the animals (STZ

TABLE 6

Cardiac survival at each after-load pressure

| Afterload (mmHg) | Number surviving (aortic flow > 0 mls/min) | | | | Percentage functioning at each afterload | | | |
|---|---|---|---|---|---|---|---|---|
| | STZ | STZ/D7 | Sham | Sham/D7 | STZ | STZ/D7 | Sham | Sham/D7 |
| 55.9 | 8 | 8 | 9 | 11 | 100% | 100% | 100% | 100% |
| 61.8 | 8 | 8 | 9 | 11 | 100% | 100% | 100% | 100% |
| 67.7 | 8 | 8 | 9 | 11 | 100% | 100% | 100% | 100% |

TABLE 6-continued

Cardiac survival at each after-load pressure

| Afterload (mmHg) | Number surviving (aortic flow > 0 mls/min) | | | | Percentage functioning at each afterload | | | |
|---|---|---|---|---|---|---|---|---|
| | STZ | STZ/D7 | Sham | Sham/D7 | STZ | STZ/D7 | Sham | Sham/D7 |
| 71.4 | 6 | 8 | 9 | 11 | 75% | 100% | 100% | 100% |
| 77.2 | 5 | 8 | 9 | 11 | 63% | 100% | 100% | 100% |
| 83.1 | 4 | 8 | 9 | 11 | 50% | 100% | 100% | 100% |
| 88.3 | 3 | 7 | 9 | 11 | 38% | 88% | 100% | 100% |
| 94.9 | 1 | 6 | 9 | 11 | 13% | 75% | 100% | 100% |
| 100.8 | 0 | 5 | 9 | 11 | 0% | 63% | 100% | 100% |
| 106.7 | 0 | 1 | 9 | 9 | 0% | 13% | 100% | 82% |

In sum, for example,

Treatment with trientine had no obvious effect on blood glucose concentrations in the two diabetic groups (as expected).

There was a small but significant improvement in the (heart weight)/(body weight) ratio in the trientine-treated diabetic group compared to that of the untreated diabetic group.

When the Pre-load was increased with the After-load held constant, cardiac output was restored to Sham values. Both the aortic and absolute coronary flows improved in the drug treated group.

Indicators for ventricular contraction and relaxation were both significantly improved in the drug treated group compared to equivalent values in the untreated diabetic group. The improvement restored function to such an extent that there was no significant difference between the drug treated and the sham-treated control groups.

The aortic transducer measures of pressure change also showed improved function in the drug treated diabetic group compared to the untreated diabetics (data not shown).

When after-load was increased in the presence of constant pre-load, it was observed that the heart's ability to function at higher after-loads was greatly improved in the drug treated diabetic group compared to the untreated diabetic group. When 50% of the untreated diabetic hearts had failed, about 90% of the trientine treated diabetic hearts were still functioning.

Compared to the untreated diabetic hearts, the response of the drug treated diabetic hearts showed significant improvements in several variables: cardiac output, aortic flow, coronary flow, as well as improved ventricular contraction and relaxation indices.

Drug treatment of normal animals had no adverse effects on cardiac performance.

It is concluded that treatment of STZ diabetic rats with trientine dramatically improves several measures of cardiac function. It is also concluded that administration of oral trientine for 7 weeks in Wistar rats with previously established diabetes of 6 weeks duration resulted in a global improvement in cardiac function. This improvement was demonstrated by improved contractile function (; +dP/dT) and a reduction in ventricular stiffness (−dP/dT). The overall ability of the Trientine treated diabetic heart to tolerate increasing after-load was also substantially improved.

Therapeutic formulations for use in the methods and preparation of the compositions of the present invention can be prepared by any methods well known in the art of pharmacy. See, for example, Gilman et al. (eds.) GOODMAN AND GILMAN'S: THE PHARMACOLOGICAL BASES OF THERAPEUTICS (8th ed.) Pergamon Press (1990); and Remington, THE SCIENCE OF PRACTICE AND PHARMACY, 20th Edition. (2001) Mack Publishing Co., Easton, Pa.; Avis et al. (eds.) (1993) PHARMACEUTICAL DOSAGE FORMS: PARENTERAL MEDICATIONS Dekker, N.Y.; Lieberman et al. (eds.) (1990) PHARMACEUTICAL DOSAGE FORMS: TABLETS Dekker, N.Y.; and Lieberman et al. (eds.) (1990) PHARMACEUTICAL DOSAGE FORMS: DISPERSE SYSTEMS Dekker, N.Y. Dosage forms useful herein include any appropriate dosage form well known in the art to be suitable for pharmaceutical formulation of compounds suitable for administration to mammals particularly humans, particularly (although not solely) those suitable for stabilization in solution of therapeutic compounds for administration to mammals preferably humans. The dosage forms of the invention thus include any appropriate dosage form now known or later discovered in the art to be suitable for pharmaceutical formulation of compounds suitable for administration to mammals particularly humans, particularly (although not solely) those suitable for stabilization in solution of compounds for administration to mammals preferably humans. One example is oral delivery forms of tablet, capsule, lozenge, or the like form, or any liquid form such as syrups, aqueous solutions, emulsion and the like, capable of protecting the compound from degradation prior to eliciting an effect, for example, in the alimentary canal if an oral dosage form. Examples of dosage forms for transdermal delivery include transdermal patches, transdermal bandages, and the like. Included within the topical dosage forms are any lotion, stick, spray, ointment, paste, cream, gel, etc., whether applied directly to the skin or via an intermediary such as a pad, patch or the like. Examples of dosage forms for suppository delivery include any solid or other dosage form to be inserted into a bodily orifice (particularly those inserted rectally, vaginally and urethrally). Examples of dosage units for transmucosal delivery include depositories, solutions for enemas, pessaries, tampons, creams, gels, pastes, foams, nebulised solutions, powders and similar formulations containing in addition to the active ingredients such carriers as are known in the art to be appropriate. Examples of dosage units for depot administration include pellets or small cylinders of active agent or solid forms wherein the active agent is entrapped in a matrix of biodegradable polymers, microemulsions, liposomes or is microencapsulated. Examples of implantable infusion devices include any solid form in which the active agent is encapsulated within or dispersed throughout a biodegradable polymer or synthetic, polymer such as silicone, silicone rubber, silastic or similar polymer. Alternatively dosage forms for infusion devices may employ liposome delivery systems.

Depending on the disease to be treated and the subject's condition, the compounds of the present invention may be administered by oral, parenteral (for example, intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The pharmaceutical composition and method of the present invention may further comprise other therapeutically active compounds as noted herein which are usually applied in the treatment of the above mentioned conditions.

In the treatment or prevention of conditions which require copper modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be about 0.005 to about 0.05, 0.05 to 0.5 or 0.5 to 5 mg/kg per day. For oral administration, the compositions are preferably provided in the form of tablets containing about 1 to 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be combined with other compounds having related utilities to prevent and treat tissue damage or excess tissue copper.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. As used herein the term "and/or" means both "and" and "or". As used herein the addition of "(s)" as part of a word embraced both the singular and plural of that word. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

We claim:

1. A method of treating heart failure in a non-diabetic human subject, comprising administering to the subject a composition comprising a therapeutically effective amount of 2,3,2 tetramine.

2. The method of claim 1, wherein heart failure in the non-diabetic subject is associated with elevated copper levels.

3. The method of claim 1 wherein the 2,3,2 tetramine is a 2,3,2 tetramine hydrochloride salt.

4. The method of any of claims 1, 2 or 3, wherein the amount of the agent administered is about 0.1 mg/kg, about 1.0 mg/kg, about 10 mg/kg, or about 100 mg/kg.

5. The method of any of claims 1, 2 or 3, wherein the agent is administered in an amount ranging from about 0.001 to about 100 mg/kg/day, from about 0.01 to about 25 mg/kg/day, or from about 0.05 to about 10 mg/kg/day, from about 0.1 to about 5 mg/kg/day, or from about 0.5 to about 5 mg/kg/day.

6. The method of any of claims 1, 2 or 3, wherein the agent is administered in an amount ranging from about 0.005 to about 0.05 mg/kg/day, from about 0.05 to about 0.5 mg/kg/day, or from about 0.001 to about 1 mg/kg/day.

7. The method of any of claims 1, 2 or 3, wherein the agent is administered in an amount ranging from about 1 to about 1000 milligrams from one to four times per day.

8. The method of any of claims 1, 2 or 3, wherein the composition comprises about 1, 5, 10, 15, 20, 25, 50, 75, 100, 150, 200, 250, 300, 400, 500, 600, 750, 800, 900, or 1000 milligrams of the agent, and is administered from one to four times per day.

9. The method of any of claims 1, 2 or 3, wherein the composition is administered orally.

10. The method of claim 9, wherein the composition is in the form of a tablet or capsule.

11. The method of claim 9, wherein the composition is in the form of a long-acting tablet or capsule.

12. The method of any one of claims 1, 2 or 3, wherein the agent is administered parenterally.

13. The method of claim 12, wherein the amount of agent administered is from about 0.001 to about 100 mg/kg/day.

14. The method of any of claims 1, 2 or 3, wherein the composition is administered intravenously, subcutaneously, transdermally, transmucosally, sublingually, or by an implantable delivery system.

15. The method of claim 1, wherein the composition further comprises one or more zinc salts.

16. The method of claim 15, wherein the zinc salt is selected from the group consisting of zinc acetate, zinc chloride and zinc sulfate, zinc citrate, zinc isocitrate, zinc ketoglutarate, zinc succinate, zinc malate, and zinc glucoante.

17. The method of claim 1, further comprising evaluating the copper values status of the subject.

18. The method of claim 17, wherein copper (II) values status is evaluated.

19. The method of claim 1, further comprising monitoring the copper values status of the subject.

20. The method of claim 19, wherein copper (II) values status is monitored.

21. The method of claim 1 wherein the therapeutically effective amount of 2,3,2 tetramine is capable of reducing copper (II) levels in the subject.

22. The method of claim 1 wherein the 2,3,2 tetramine is 2,3,2 tetramine tetrahydrochloride.

* * * * *